US007132525B2

(12) United States Patent
Laby et al.

(10) Patent No.: US 7,132,525 B2

(45) Date of Patent: Nov. 7, 2006

(54) HYPERSENSITIVE RESPONSE ELICITOR FRAGMENTS ELICITING A HYPERSENSITIVE RESPONSE AND USES THEREOF

(75) Inventors: Ron J. Laby, Houston, TX (US); Zhong-Min Wei, Kirkland, WA (US); Steven V. Beer, Ithaca, NY (US)

(73) Assignees: Cornell Research Foundation, Inc., Ithaca, NY (US); Eden BioScience Corporation, Bothell, WA (US)

(*) Notice: Subject to any disclaimer, the term of this patent is extended or adjusted under 35 U.S.C. 154(b) by 207 days.

(21) Appl. No.: 10/387,806

(22) Filed: Mar. 12, 2003

(65) Prior Publication Data

US 2003/0182683 A1 Sep. 25, 2003

Related U.S. Application Data

(62) Division of application No. 09/086,118, filed on May 28, 1998, now Pat. No. 6,583,107.

(60) Provisional application No. 60/048,109, filed on May 30, 1997.

(51) Int. Cl.
*C07H 21/04* (2006.01)
*C12N 15/09* (2006.01)

(52) U.S. Cl. .................. 536/23.7; 435/320.1; 435/410; 435/69.1; 530/300; 530/350; 800/298

(58) Field of Classification Search .................... 514/2, 514/12; 530/350, 300; 536/23.7; 435/411, 435/69.1, 320.1, 410; 800/298
See application file for complete search history.

(56) References Cited

U.S. PATENT DOCUMENTS

| | | | |
|---|---|---|---|
| 4,569,841 | A | 2/1986 | Liu |
| 4,597,972 | A | 7/1986 | Taylor |
| 4,601,842 | A | 7/1986 | Caple et al. |
| 4,740,593 | A | 4/1988 | Gonzalez et al. |
| 4,851,223 | A | 7/1989 | Sampson |
| 4,886,825 | A | 12/1989 | Ruess et al. |
| 4,931,581 | A | 6/1990 | Schurter et al. |
| 5,057,422 | A | 10/1991 | Bol et al. |
| 5,061,490 | A | 10/1991 | Paau et al. |
| 5,135,910 | A | 8/1992 | Blackburn et al. |
| 5,173,403 | A | 12/1992 | Tang et al. |
| 5,217,950 | A | 6/1993 | Blackburn et al. |
| 5,243,038 | A | 9/1993 | Ferrari et al. |
| 5,244,658 | A | 9/1993 | Parke |
| 5,260,271 | A | 11/1993 | Blackburn et al. |
| 5,348,743 | A | 9/1994 | Ryals et al. |
| 5,494,684 | A | 2/1996 | Cohen |
| 5,523,311 | A | 6/1996 | Schurter et al. |
| 5,550,228 | A | 8/1996 | Godiard et al. |
| 5,552,527 | A | 9/1996 | Godiard et al. |
| 5,708,139 | A | 1/1998 | Collmer et al. |
| 5,977,060 | A | 11/1999 | Zitter et al. |
| 6,235,974 | B1 | 5/2001 | Qiu et al. |
| 6,277,814 | B1 | 8/2001 | Qiu et al. |

FOREIGN PATENT DOCUMENTS

| | | |
|---|---|---|
| EP | 0 612 848 A3 | 8/1994 |
| WO | WO 93/23532 | 11/1993 |
| WO | WO 94/01546 | 1/1994 |
| WO | WO 94/26782 | 11/1994 |
| WO | WO 95/19443 | 7/1995 |
| WO | WO 96/39802 | 12/1996 |
| WO | WO 98/24297 | 6/1998 |
| WO | WO 98/32844 | 7/1998 |
| WO | WO 98/37752 | 9/1998 |

OTHER PUBLICATIONS

Collmer et al., "*Erwinia chyrsanthemi* and *Pseudomonas syringae:* Plant Pathogens Trafficking in Extracellular Virulence Proteins," *Current Topics in Microbiology and Immunology*, 192:43-78 (1994).

Frederick et al., "The WTS Water-Soaking Genes of *Erwinia stewartii* are Related to *hrp* Genes," Seventh International Symposium on Molecular Plant Microbe Interactions, Abstract No. 191 (Jun. 1994).

Wei et al., "Proteinaceous Elicitors of the Hypersensitive Response from *Xanthomonas campestris* pv. *glycines,"* Seventh International Symposium on Molecular Plant Microbe Interactions, Abstract No. 244 (Jun. 1994).

Preston et al., "The HrpZ Proteins of *Pseudomonas syringae* pvs. *syringae, glycinea,* and *tomato* are Encoded by and Operon Containing *Yersinia ysc* Homologs and Elicit the Hypersensitive Response in Tomato but not Soybean," *Mol. Plant-Microbe Interact.*, 8(5):717-32 (1995).

Bauer et al., "*Erwinia chrysanthemi hrp* Genes and their Involvement in Elicitation of the Hypersensitive Response in Tobacco," Sixth International Symposium on Molecular Plant Microbe Interactions, Abstract No. 146 (July 1992).

(Continued)

*Primary Examiner*—Kathleen M. Kerr
*Assistant Examiner*—Chih-Min Kam
(74) *Attorney, Agent, or Firm*—Nixon Peabody LLP

(57) ABSTRACT

Isolated fragments of an *Erwinia* hypersensitive response elicitor protein or polypeptide that elicit a hypersensitive response in plants and isolated DNA molecules that encode those fragments are disclosed. Isolated fragments of hypersensitive response elicitor proteins or polypeptides, which elicit a hypersensitive response, and the isolated DNA molecules that encode them can be used to impart disease resistance to plants, to enhance plant growth, and/or to control insects on plants, either by applying the hypersensitive response eliciting fragments to plants or plant seeds or by providing transgenic plants or plant seeds transformed with a DNA molecule encoding a hypersensitive response eliciting fragment.

9 Claims, 13 Drawing Sheets

OTHER PUBLICATIONS

Stryer, L., "Enzymes are Highly Specific," *Biochemistry*, San Francisco: W.H. Freeman and Company, p. 116 (1975).

Keen et al., "Inhibition of the Hypersensitive Reaction of Soybean Leaves to Incompatible *Pseudomonas* spp. by Blasticidin S, Streptomycin or Elevated Temperature," *Physiological Plant Pathology*, 18:325-37 (1981).

Lerner, R.A., "Tapping the Immunological Repertoire to Produce Antibodies of Predetermined Specificity," *Nature*, 299:592-96 (1982).

Staskawicz et al., "Cloned Avirulence Gene of *Pseudomonas Syringae* pv. *glycinea* Determines Race-specific Incompatibility on *Glycine max* (L.) Merr.," *Proc. Natl. Acad. Sci. USA*, 81:6024-28 (1984).

Bauer et al., "*Erwinia chrysanthemi* $Harpin_{Ech}$ : An Elicitor of the Hypersensitive Response that Contributes to Soft-Rot Pathogenesis," *MPMI*, 8(4):484-91 (1995).

Huang et al., "Characterization of the *hrp* Cluster from *Pseudomonas syringae* pv. *syringae* 61 and Tn*phoA* Tagging of Genes Encoding Exported or Membrane-Spanning Hrp Proteins," *Molec. Plant-Microbe Interact.*, 4(5):469-76 (1991).

Huang et al., "The *Pseudomonas syringae* pv. *syringae* 61 *hrpH* Product, an Envelope Protein Required for Elicitation of the Hypersensitive Response in Plants," *J. Bacteriol.*, 174(21):6878-85 (1992).

Bonas, U., "*hrp* Genes of Phytopathogenic Bacteria," *Current Topics in Microbio.*, 192:79-98 (1994).

Arlat et al., "PopA1, A Protein Which Induces a Hypersensitivity-Like Response on Specific Protein *Petunia* Genotypes, is Secreted via the Hrp Pathway of *Pseudomonas solanacearum," The EMBO J.*, 13(3):543-53 (1994).

Kessmann et al., "Induction of Systemic Acquired Disease Resistance in Plants By Chemicals," *Ann. Rev. Phytopathol.*, 32:439-59 (1994).

Kelman, A., "The Relationship of Pathogenicity in *Pseudomonas solanacearum* To Colony Appearance on a Tetrazolium Medium," *Phytopathology*, 44:693-95 (1954).

Winstead et al., "Inoculation Techniques For Evaluating Resistance to *Pseudomonas solanacearum," Phytopathology*, 42:628-34 (1952).

Ahl et al., "Iron Bound-Siderophores, Cyanic Acid, and Antibiotics Involved in Suppression of *Thielaviopsis basiocola* by a *Pseudomonas fluorescens* Strain," *J. Phytopathology*, 116:121-34 (1986).

Anderson et al., "Responses of Bean to Root Colonization with *Pseudomonas putida* in a Hydroponic System," *Phytopathology*, 75(9):992-95 (1985).

Gardner et al., "Growth Promotion and Inhibition by Antibiotic-Producing Fluorescent Pseudomonads on Citrus Roots," *Plant and Soil*, 77:103-13 (1984).

Kloepper, J.W., "Effect of Seed Piece Inoculation with Plant Growth-Promoting Rhizobacteria on Populations of *Erwinia carotovora* on Potato Roots and In Daughter Tubers," *Phytopathology*, 73(2):217-19 (1983).

Atkinson et al., "The Hypersensitive Reaction of Tobacco to *Pseudomonas syringae* pv. *pisi," Plant Physiol.*, 79:843-47 (1985).

Huynh et al., "Bacterial Blight of Soybean: Regulation of a Pathogen Gene Determining Host Cultivar Specificity," *Science*, 245:1374-77 (1986).

Kloepper et al., "Plant Growth-Promoting Rhizobacteria on Canola (Rapeseed)," *Plant Disease*, 72(1):42-6 (1988).

Kloepper et al., "Enhanced Plant Growth by Siderophores Produced by Plant Growth-Promoting Rhizobacteria," *Nature*, 286:885-86 (1980).

Kloepper et al., "*Pseudomonas* Siderophores: A Mechanism Explaining Disease-Suppressive Soils," *Current Microbiology*, 4:317-20 (1980).

Kloepper et al., "Emergence-Promoting Rhizobacteria: Description and Implications for Agriculture," In:*Iron, Siderophores, and Plant Disease*, Swinborne (ed), Plenum, NY, 155-64 (1986).

Kloepper et al., "Relationships of *in vitro* Antibiosis of Plant Growth-Promoting Rhizobacteria to Plant Growth and the Displacement of Root Microflora," *Phytopathology*, 71(10):1020-24 (1981).

Kloepper et al., "Effects of Rhizosphere Colonization by Plant Growth-Promoting Rhizobacteria on Potato Plant Development and Yield," *Phytopathology*, 70(11):1078-82 (1980).

Kloepper et al., "Plant Growth Promotion Mediated by Rhizosphere Bacterial Colonizers," In: *The Rhizosphere and Plant Growth*, 315-32, Keister et al. (eds), pp. 315-26 (1991).

Lifshitz et al., "Growth Promotion of Canola (rapeseed) Seedlings by a Strain of *Pseudomonas putida* Under Gnotobiotic Conditions," Conditions, *Microbiol.* 33:390-95 (1987).

Liu et al., "Induction of Systemic Resistance in Cucumber Against Bacterial Angular Leaf Spot by Plant Growth-Promoting Rhizobacteria," *Phytopathology*, 85(8):843-47 (1995).

Loper et al., "Influence of Bacterial Sources of Indole-3-acetic Acid on Root Elongation of Sugar Beet," *Phytopathology*, 76(4):386-89 (1986).

Schroth et al., "Disease-Suppressive Soil and Root-Colonizing Bacteria," *Science*, 216:1376-81 (1982).

Stutz et al., "Naturally Occurring Fluorescent Pseudomonads Involved Suppression of Black Root Rot of Tobacco," *Phytopathology*, 76(2):181-85 (1986).

Lindgren et al., "Gene Cluster of *Pseudomonas syringae* pv. "*phaseolicola*" Controls Pathogenicity of Bean Plants and Hypersensitivity on Nonhost Plants," *J. Bacteriol.*, 168(2):512-22 (1986).

Bauer et al., "Cloning of a Gene from *Erwinia amylovora* Involved in Induction of Hypersensitivity and Pathogenicity," *Plant Pathogenic Bacteria*, Proceedings of the Sixth International Conference on Plant Pathogenic Bacteria, Maryland, pp. 425-29 (1987).

Wei et al., "Induction of Systemic Resistance of Cucumber to *Colletotrichum orbiculare* by Select Strains of Plant Growth-Promoting Rhizobacteria," *Phytopathology*, 81:1508-12 (1991).

Wei et al., "Induction of Systemic Resistance with Seed Treatment by PGPR Strains," *Bulletin of the International Organization for Biological and Integrated Control of Noxious Animals and Plants, Western Palearctic Section*, pp. 191-194 (1991).

Weller, D.M., "Biological Control of Soilborne Plant Pathogens in the Rhizosphere with Bacteria," *Ann. Rev. Phytopathol.*, 26:379-407 (1988).

Young et al., "PGPR: Is There a Relationship Between Plant Growth Regulators and the Stimulation of Plant Growth or Biological Activity?," In: Keel et al., eds., *The Second International Workshop on Plant Growth-Promoting Rhizobacteria. IOBC/WPRS Bulletin*, Interlaken, Switzerland, pp. 182-186 (Oct. 14-19, 1990).

Wei et al., "Induced Systemic Resistance by Select Plant Growth-Promoting Rhizobacteria Against Bacterial Wilt of Cucumber and the Beetle Vectors," *Phytopathology*, 86:1154, Abstract No. 313 (1995).

Wieringa-Brants et al., Induced Resistance in Hypersensitive Tobacco Against Tobacco Mosaic Virus by Injection of Intercellular Fluid from Tobacco Plants with Systemic Acquired Resistance, *Phytopathology*, 118:165-70 (1987).

Malamy et al., "Salicylic Acid: A Likely Endogenous Signal in the Resistance Response of Tobacco to Viral Infection," *Science*, 250:1002-04 (1990).

Dean et al., "Immunisation Against Disease: The Plant Fights Back," *British Mycological Society Symposium*, pp. 383-410 (1988).

Cameron et al., "Biologically Induced Systemic Acquired Resistance in *Arabidopsis thaliana," The Plant Journal*, 5(5):715-25 (1994).

Laby et al., "Structural and Functional Analysis of *Erwinia amylovora* Harpin, An Elicitor of the Plant Hypersensitive Response," *Phytopathology*, 84:345 (1994).

Van Gijsegem et al., "Conservation of Solution Pathways for Pathogenicity Determinants of Plant and Animal Pathogenic Bacteria," *Trends Micorbiol.*, 1:175-80 (1993).

Kamoun, et al., "Extracellular Protein Elicitors from *Phytophthora:* Host-Specificity and Induction of Resistance to Bacterial and Fungal Phytopathogens," *Molecular Plant-Microbe Interactions*, 6(1):15-25 (1993).

Baillieul, et al., "A New Elicitor of the Hypersensitive Response in Tobacco: A Fungal Glycoprotein Elicits Cell Death, Expression of Defense Genes, Production of Salicylic Acid, and Induction of Systemic Acquired Resistance," *The Plant Journal*, 8(4):551-60 (1995).

Collinge et al., "Plant Gene Expression in Response to Pathogens," *Plant Molecular Biology*, 9:389-410 (1987).

Shatzman et al., "Expression, Identification, and Characterization of Recombinant Gene Products in *Escherichia coli," Methods in Enzymology*, 152:661-73 (1987).

Tenhaken, et al., "Function of the Oxidative Burst in Hypersensitive Disease Resistance," *Proc. Natl. Acad. Sci. USA*, 92:4158-63 (1995).

Bonnet, et al., "Induction de nécroses foliaires, de protéines b et de résistance dans les interactions tabac *Phytophthora," Agronomie*, 6(9):829-37 (1986), English abstract only.

Gallitelli, et al., "Satellite-Mediated Protection of Tomato Against Cucumber Mosaic Virus: II. Field Test Under Natural Epidemic Conditions in Southern Italy," *Plant Disease*, 75(1):93-5 (1991).

Kang et al., "Control of Tomato Mosaic Disease by Interference of an Attenuated Virus," *Res. Rept. RDA* (*Hort.*), 27(1):17-26 (1985).

Montasser, et al., "Satellite-Mediated Protection of Tomato Against Cucumber Mosaic Virus: I. Greenhouse Experiments and Simulated Epidemic Conditions in the Field," *Plant Disease*, 75(1):86-92 (1991).

Marks, R.J., "Varietal Resistance to Potato Cyst Nematode," *Agricultural Entomology*, pp. 63-67 (1979).

Walton, et al., "Host-Selective Toxins and Disease Specificity: Perspectives and Progress," *Annu. Rev. Phytopathol.*, 31:275-303 (1993).

Atkinson, M.M., "Molecular Mechanisms of Pathogen Recognition by Plants," *Advances in Plant Pathology*, 10:36-64 (1993).

Godiard, et al., "Differential Regulation in Tobacco Cell Suspensions of Genes Involved in Plant-Bacteria Interactions by Pathogen-Related Signals," *Plant Molecular Biology*, 17:409-13 (1991).

Ricci, et al., "Structure and Activity of Proteins from Pathogenic Fungi *Phytophthora* Eliciting Necrosis and Acquired Resistance in Tobacco," *Eur. J. Biochem.*, 183:555-63 (1989).

Shields, R., "Towards Insect-Resistant Plants," *Nature*, 328:12-13 (1987).

Huang et al., "Molecular Cloning of a *Pseudomonas syringae* pv. *syringae* Gene Cluster That Enables *Pseudomonas fluorescens* To Elicit the Hypersensitive Response in Tobacco Plants," *J. Bacteriol.*, 170(10):4748-56 (1988).

Ricci, et al., "Differential Production of Parasiticein, an Elicitor of Necrosis and Resistance in Tobacco, by Isolates of *Phytophthora parasitica," Plant Pathology*, 41:298-307 (1992).

Honée, et al., "Molecular Characterization of the Interaction Between the Fungal Pathogen *Cladosporium fulvum* and Tomato," *Advances in Molecular Genetics of Plant-Microbe Interactions*, 3:199-206 (1994).

Keller, et al., "Responses to Tobacco to Elicitins, Proteins From *Phytophthora* Spp. Eliciting Acquired Resistance," *Advances in Molecular Genetics of Plant-Microbe Interactions*, 3:327-32 (1994).

Keen, et al., "Bacteria Expressing Avirulence Gene D Produce a Specific Elicitor of the Soybean Hypersensitive Reaction," *Molecular Plant-Microbe Interactions*, 3(2):112-21 (1990).

Bauer, et al., "*Erwinia chrysanthemi hrp* Genes and Their Involvement in Soft Rot Pathogenesis and Elicitation of the Hypersensitive Response," *MPMI*, 7(5):573-81 (1994).

Schottens-Toma et al., "Purification and Primary Structure of a Necrosis-inducing Peptide from the Apoplastic Fluids of Tomato Infected with *Cladosporium fulvum* (syn *Fulvia fulva*)," *Physiological and Molecular Plant Pathology*, 33:59-67 (1988).

Steinberger et al., "Creation and Complementation of Pathogenicity Mutants of *Erwinia amylovora," Molecular Plant-Microbe Interactions*, 1(3):135-44 (1988).

Beer et al., "The Hypersensitive Response is Elicited by *Escherichia coli* Containing a Cluster of Pathogenicity Genes from *Erwinia amylovora," Phytopathology*, 79(10):1156 (Abstract 169) (1989).

Hiatt et al., "Production of Antibodies in Transgenic Plants," *Nature*, 342:76-8 (1989).

Hippe et al., "*In Situ* Localization of a Foreign Protein in Transgenic Plants by Immunoelectron Microscopy Following High Pressure Freezing. Freeze Substitution and Low Temperature Embedding," *European Journal of Cell Biology*, 50:230-34(1989).

Huang et al., "Isolation and Purification of a Factor from *Pseudomonas solanacearum* That Induces a Hypersensitive-like Response in Potato Cells," *Molecular Plant-Microbe Interactions*, 2(3):132-38 (1989).

James et al., "Genetic Transformation of Apple (*Malus pumila* Mill.) Using a Disarmed Ti-binary Vector," *Plant Cell Reports*, 7:658-61 (1989).

Laby et al., "Cloning and Preliminary Characterization of an *hrp* Gene Cluster of *Erwinia amylovora," Phytopathology*, 79(10):1211 (Abstract 607) (1989).

Dow et al., "Extracellular Proteases from *Xanthomonas campestris* pv. Campestris, the Black Rot Pathogen," *Applied and Environmental Microbiology*, 56(10):2994-98 (1990).

Walters et al., "Gene for Pathogenicity and Ability to Cause the Hypersensitive Reaction Cloned from *Erwinia amylovora," Physiological and Molecular Plant Pathology*, 36:509-21 (1990).

Wu et al., "Cloning, Genetic Organization, and Characterization of a Structural Gene Encoding Bacillopeptidase F from *Bacillus subtilis," The Journal of Biological Chemistry*, 265(12):6845-50 (1990).

Bauer et al., "Further Characterization of an *hrp* Gene Cluster of *Erwinia amylovora," Molecular Plant-Microbe Interactions*, 4(5):493-99 (1991).

Beer et al., "The *hrp* Gene Cluster of *Erwinia amylovora," Advances in Molecular Genetics of Plant-Microbe Interactions*, 1:53-60 (1991).

Benvenuto et al., "'Phytoantibodies': A General Vector for the Expression of Immunoglobulin Domains in Transgenic Plants," *Plant Molecular Biology*, 17:865-74 (1991).

Milat et al., "Physiological and Structural Changes in Tobacco Leaves Treated with Cryptogein, a Proteinaceous Elicitor from *Phytophthora cryptogea," Phytopathology*, 81(11):1364-68 (1991).

Ruberti et al., "A Novel Class of Plant Proteins Containing a Homeodomain with a Closely Linked Leucine Zipper Motif," *The EMBO Journal*, 10(7):1787-91 (1991).

Quigley et al., "Nucleotide Sequence and Expression of a Novel Glycine-Rich Protein Gene from *Arabidopsis thaliana," Plant Molecular Biology*, 17:949-52 (1991).

van Kan et al., "Cloning and Characterization of cDNA of Avirulence Gene *avr9* of the Fungal Pathogen *Cladosporium fulvum*, Causal Agent of Tomato Leaf Mold," *Molecular Plant-Microbe Interactions*, 4(1):52-9 (1991).

Waldmann, T.A., "Monoclonal Antibodies in Diagnosis and Therapy," *Science*, 252:1657-62 (1991).

Willis et al., "*hrp* Genes of Phytopathogenic Bacteria," *Molecular Plant-Microbe Interactions*, 4:(2) 132-38 (1991).

Beer et al., "Are Harpins Universal Elicitors of the Hypersensitive Response of Phytopathogenic Bacteria?," *Advances in Molecular Genetics of Plant-Microbe Interactions*, 2:281-86 (1992).

Laby et al., "Hybridization and Functional Complementation of the *hrp* Gene Cluster from *Erwinia amylovora* Strain Ea321 with DNA of Other Bacteria," *Molecular Plant-Microbe Interactions*, 5(5):412-19 (1992).

Sandhu, "Protein Engineering of Antibodies," *Crit. Rev. in Biotech.*, 12(5/6):437-62 (1992).

Wei et al., "Harpin, Elicitor of the Hypersensitive Response Produced by the Plant Pathogen *Erwinia amylovora," Science*, 257:85-8 (1992).

He et al., "*Pseudomonas syringae* pv. *syringae* $Harpin_{Pss}$: A Protein that is Secreted via the Hrp Pathway and Elicits the Hypersensitive Response in Plants," *Cell*, 73:1255-66 (1993).

Bonas, U., "Bacterial Home Goal by Harpins," *Trends in Microbiology*, 2:1-2 (1994).

Boccara, et al., "Plant Defense Elicitor Protein Produced by *Erwinia chrysanthemi," Mechanisms of Plant Defense Responses*, p. 166 (1993).

Qui et al., "Treatment of Tomato Seed with Harpin Enhances Germination and Growth and Induces Resistance to *Ralstonia solanacearum,*" *Phytopathology*, 87:6, S80 (1997).
Burr et al., "Increased Potato Yields by Treatment of Seedpieces with Specific Strains of *Pseudomonas fluorescens* and *P. putida,*" *Phytopathology*, 68:1377-1383 (1978).
Ricci et al., "Proteinaceous Elicitors of Plant Defense Responses," B. Fritig eds., *Mechanisms of Plant Defense Responses*, Netherlands, pp. 121-130 (1993).
Keen et al., "Syringolide Elicitors Specified By Avirulence Gene D Alleles In *Pseudomonas syringae,*" *Advances in Molecular Genetics of Plant-Microbe Interactions*, 3:41-48 (1994).
Klessig et al., "The Salicylic Acid Signal In Plants," *Plant Molecular Biology*, 26:1439-1458 (1994).
Bogdanove et al., "Unified Nomenclature For Broadly Conserved *hrp* Genes of Phytopathogenic Bacteria," *Molecular Microbiology*, 20(3):681-683 (1996).
Bonnet et al., "Acquired Resistance Triggered By Elicitins In Tobacco and Other Plants," *European Journal of Plant Pathology*, 102:181-192 (1996).
Cui et al., "The RsmA$^{-}$ Mutants of *Erwinia carotovora* subsp. *carotovora* Strain Ecc71 Overexpress $hrpN_{Ecc}$ and Elicit a Hypersensitive Reaction-like Response in Tobacco Leaves," *Molecular Plant-Microbe Interactions*, 9(7):565-573 (1996).
Gopalan et al., "Bacterial Genes Involved in the Elicitation of Hypersensitive Response and Pathogenesis," *Plant Disease*, 80(6):604-610 (1996).
Hoffland et al., "Comparison of Systemic Resistance Induced by Avirulent and Nonpathogenic *Pseudomonas* Species," *Phytopathology*, 86(7):757-762 (1996).
Ryals et al., "Systemic Acquired Resistance," *The Plant Cell*, 8:1809-1819 (1996).
Wei et al., "Induced Systemic Resistance to Cucumber Dieseases and Increased Plant Growth by Plant Growth-Promoting Rhizobacteria Under Field Conditions," *Phytopathology*, 86:221-224 (1996).
Wengelnik et al., "Expression and Localization of HrpA1, a Protein of *Xanthomonas campestris* pv. vesicatoria Essential for Pathogenicity and Induction of the Hypersensitive Reaction," *Journal of Bacteriology*, 178:1061-1069 (1996).
Inbar et al., "Elicitors of Plant Defensive Systems Reduce Insect Densities and Disease Incidence," *Journal of Chemical Ecology*, 24(1):135-149 (1998).
Jin et al., "A Truncated Fragment of $Harpin_{Pes}$ Induces Systemic Resistance To *Xanthomonas campetris* pv. *oryzae* In Rice," *Physiological and Molecular Plant Pathology*, 51:243-257 (1997).
Linthorst et al., "Constitutive Expression of Pathogenesis Related Proteins PR-1, GRP, and PR-S in Tobacco Has No Effect on Virus Infection," *Plant Cell* 1:285-291 (1989).
Wei et al., "Harpin, Elicitor of the Hypersensitive Response Produced by the Plant Pathogen *Erwinia amylovora,*" *Science* 257:85-88 (1992).
Baillieul et al., "A New Elicitor of the Hypersensitive Response in Tobacco: A Fungal Glycoprotein elicits Cell Death, Expression of Defence Genes, Production of Salicylic Acid, and Induction of Systemic Acquired Resistance," *The Plant J.* 8:551-560 (1995).
McGrul et al., "Structure, Expression, and Antisense Inhibition of the Systemin Precursor Gene," *Science* 255:1570-1573 (1992).
Malamy et al., "Salicylic Acid and Plant Disease Resistance," *Plant J.* 2:643-654 (1992).
US 5,650,387, 07/1997, Wei et al. (withdrawn)

| | A | B | C | D |
|---|---|---|---|---|
| | wt | 403 | + | + |
| | C31 | 372 | + | + |
| | C82 | 321 | + | + |
| | C82Ω | 321 | - | NT |
| | C128Ω | 275 | - | NT |
| | C185 | 218 | + | + |
| | C281 | 122 | + | + |
| | C305 | 98 | + | + |
| | C368 | 35 | - | NT |
| | C375 | 28 | - | NT |
| | I175 | 228 | + | + |
| | I234 | 169 | - | NT |
| | N11 | 392 | - | NT |
| | N35 | 368 | - | NT |
| | P91 | 91 | + | |
| | P95 | 95 | + | + |
| | P64 | 64 | + | |
| | P68 | 68 | + | + |

1   98  137   204

FRAGMENTS SEPARATELY SUFFICIENT FOR HR-ELICITING ACTIVITY

| Gene | Organism[a] | N-terminal amino acid sequence |
|---|---|---|
| HrpN | Ech | MQITIKAHIGGDLGVSGLGAQGLKGLNSAA |
| HrpN | Ecc | M.LNSLGGGAS.LQITIK.AGGNGGLFPSQ |
| HrpN | Eam | MSLNTSGLGASTMQISTGGAGGNNGLLGTS |
| WtsN | Est | MSMNTSPLGTSALQVTL...GGNNGLMGTD |
| orf1B | Eam | MSILTLNNNTSS.SPGLFQSGGDNGLGGHA |

[a]Ech= *E. chrysanthemi*; Ecc= *E. carotovora* subsp. *carotovora*; Eam= *E. amylovora*; Est= *E. stewartii*.

FIG. 8

|       |                          |       |     |                       |
|-------|--------------------------|-------|-----|-----------------------|
| #1    | HARPIN                   |       | HR  |                       |
|       | 1 ─────────────── 403    |       | +   |                       |

3   C-TERMINAL FRAGMENTS         +
     105 ─────────────── 403
4       169 ─────────── 403      −
5           210 ─────── 403      −
6               267 ─── 403      −
7                   343 403      −

8   N-TERMINAL FRAGMENTS         −
     1 ── 75
9   1 ──── 104                   +/−
10  1 ─────── 168                +
11  1 ──────────── 266           +
12  1 ──────────────── 342       +

13  INTERNAL FRAGMENTS           +
     76 ────────── 209
14  76 ───── 168                 −
15      105 ──── 209             +
16          169 209              NA
17      105 ── 168               −

HR   SYNTHESIZED OLIGOPEPTIDES
18  99 ─────────── 209           +
19      137 ── 204               +    150 ── 179
20      137 ─ 180                +    137 ── 166
21  105 ────── 180               +    121 150
22          150 ── 209           NA   137 156
23          150 ─ 180            NA

N1; 5'-GGGAATTCATATGAGTCTGAATACAAGTGGG-3'
N76; 5'-GGGAATTCATATGGGCGGTGGCTTAGGCGGT-3'
N99; 5'-GGCATATGTCGAACGCGCTGAACGATATG-3'
N105; 5'-GGGAATTCATATGTTAGGCGGTTCGCTGAAC-3'
N110; 5'-GGCATATGCTGAACACGCTGGGCTCGAAA-3'
N137; 5'-GGCATATGTCAACGTCCCAAAACGACGAT-3'
N150; 5'-GGCATATGTCCACCTCAGACTCCAGCG-3'
N169; 5'-GGGAATTCATATGCAAAGCCTGTTTGGTGATGGG-3'
N210; 5'-GGGAATTCATATGGGTAATGGTCTGAGCAAG-3'
N267; 5'-GGGAATTCATATGAAAGCGGGCATTCAGGCG-3
N343; 5'-GGGAATTCATATGACACCAGCCAGTATGGAGCAG-3'
C75; 5'-GCAAGCTTAACAGCCCACCACCGCCCATCAT-3'
C104; 5'-GCAAGCTTAAATCGTTCAGCGCGTTCGACAG-3'
C168; 5'-GCAAGCTTAATATCTCGCTGAACATCTTCAGCAG-3'
C180; 5'-GCAAGCTTAAGGTGCCATCTTGCCCATCAC-3'
C204; 5'-GCAAGCTTAAATCAGTGACTCCTTTTTTATAGGC-3
C209; 5'-GCAAGCTTAACAGGCCCGACAGCGCATCAGT-3'
C266; 5'-GCAAGCTTAAACCGATACCGGTACCCACGGC-3'
C342; 5'-GCAAGCTTAATCCGTCGTCATCTGGCTTGCTCAG-3'
C403; 5'-GCAAGCTTAAGCCGCGCCCAGCTTG-3'

*FIG. 11*

SEQUENCE LISTING

<160> NUMBER OF SEQ ID NOS: 30

<210> SEQ ID NO 1
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 1
gggaattcat atgagtctga atacaagtgg g 31

<210> SEQ ID NO 2
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 2
gggaattcat atgggcggtg gcttaggcgg t 31

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 3
ggcatatgtc gaacgcgctg aacgatatg 29

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 4
gggaattcat atgttaggcg gttcgctgaa c 31

-continued

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 5
ggcatatgct gaacacgctg ggctcgaaa 29

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 6
ggcatatgtc aacgtcccaa aacgacgat 29

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 7
ggcatatgtc cacctcagac tccagcg 27

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 8
gggaattcat atgcaaagcc tgtttggtga tggg 34

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 9
gggaattcat atgggtaatg gtctgagcaa g 31

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 10
gggaattcat atgaaagcgg gcattcaggc g 31

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: Primer

```
<400> SEQUENCE: 11

gggaattcat atgacaccag ccagtatgga gcag                              34

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 12

gcaagcttaa cagcccacca ccgcccatca t                                 31

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 13

gcaagcttaa atcgttcagc gcgttcgaca g                                 31

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 14

gcaagcttaa tatctcgctg aacatcttca gcag                              34

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 15

gcaagcttaa ggtgccatct tgcccatcac                                   30

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 16

gcaagcttaa atcagtgact ccttttttat aggc                              34

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 17

gcaagcttaa caggcccgac agcgcatcag t                                 31

<210> SEQ ID NO 18
<211> LENGTH: 31
```

-continued

<212> TYPE: DNA
<213> ORGANISM: Artificial Sequence
<220> FEATURE:
<223> OTHER INFORMATION: Description of Artificial Sequence: Primer

<400> SEQUENCE: 18
gcaagcttaa accgataccg gtacccacgg c 31

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 19
gcaagcttaa tccgtcgtca tctggcttgc tcag 34

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 20
gcaagcttaa gccgcgccca gcttg 25

<210> SEQ ID NO 21
<211> LENGTH: 338
<212> TYPE: PRT
<213> ORGANISM: Erwinia chrysanthemi

<400> SEQUENCE: 21

```
Met Gln Ile Thr Ile Lys Ala His Ile Gly Gly Asp Leu Gly Val Ser
  1               5                  10                  15

Gly Leu Gly Ala Gln Gly Leu Lys Gly Leu Asn Ser Ala Ala Ser Ser
             20                  25                  30

Leu Gly Ser Ser Val Asp Lys Leu Ser Ser Thr Ile Asp Lys Leu Thr
         35                  40                  45

Ser Ala Leu Thr Ser Met Met Phe Gly Gly Ala Leu Ala Gln Gly Leu
     50                  55                  60

Gly Ala Ser Ser Lys Gly Leu Gly Met Ser Asn Gln Leu Gly Gln Ser
 65                  70                  75                  80

Phe Gly Asn Gly Ala Gln Gly Ala Ser Asn Leu Leu Ser Val Pro Lys
                 85                  90                  95

Ser Gly Gly Asp Ala Leu Ser Lys Met Phe Asp Lys Ala Leu Asp Asp
            100                 105                 110

Leu Leu Gly His Asp Thr Val Thr Lys Leu Thr Asn Gln Ser Asn Gln
        115                 120                 125

Leu Ala Asn Ser Met Leu Asn Ala Ser Gln Met Thr Gln Gly Asn Met
    130                 135                 140

Asn Ala Phe Gly Ser Gly Val Asn Asn Ala Leu Ser Ser Ile Leu Gly
145                 150                 155                 160

Asn Gly Leu Gly Gln Ser Met Ser Gly Phe Ser Gln Pro Ser Leu Gly
                165                 170                 175

Ala Gly Gly Leu Gln Gly Leu Ser Gly Ala Gly Ala Phe Asn Gln Leu
            180                 185                 190

Gly Asn Ala Ile Gly Met Gly Val Gly Gln Asn Ala Ala Leu Ser Ala
        195                 200                 205
```

-continued

Leu Ser Asn Val Ser Thr His Val Asp Gly Asn Asn Arg His Phe Val
    210                 215                 220

Asp Lys Glu Asp Arg Gly Met Ala Lys Glu Ile Gly Gln Phe Met Asp
225                 230                 235                 240

Gln Tyr Pro Glu Ile Phe Gly Lys Pro Glu Tyr Gln Lys Asp Gly Trp
                245                 250                 255

Ser Ser Pro Lys Thr Asp Asp Lys Ser Trp Ala Lys Ala Leu Ser Lys
            260                 265                 270

Pro Asp Asp Asp Gly Met Thr Gly Ala Ser Met Asp Lys Phe Arg Gln
        275                 280                 285

Ala Met Gly Met Ile Lys Ser Ala Val Ala Gly Asp Thr Gly Asn Thr
    290                 295                 300

Asn Leu Asn Leu Arg Gly Ala Gly Gly Ala Ser Leu Gly Ile Asp Ala
305                 310                 315                 320

Ala Val Val Gly Asp Lys Ile Ala Asn Met Ser Leu Gly Lys Leu Ala
                325                 330                 335

Asn Ala

<210> SEQ ID NO 22
<211> LENGTH: 2141
<212> TYPE: DNA
<213> ORGANISM: Erwinia chrysanthemi

<400> SEQUENCE: 22 cgatttacc cgggtgaacg tgctatgacc gacagcatca cggtattcga caccgttacg 60
gcgtttatgg ccgcgatgaa ccggcatcag gcggcgcgct ggtcgccgca atccggcgtc 120
gatctggtat ttcagtttgg ggacaccggg cgtgaactca tgatgcagat tcagccgggg 180
cagcaatatc ccggcatgtt gcgcacgctg ctcgctcgtc gttatcagca ggcggcagag 240
tgcgatggct gccatctgtg cctgaacggc agcgatgtat tgatcctctg gtggccgctg 300
ccgtcggatc ccggcagtta tccgcaggtg atcgaacgtt tgtttgaact ggcgggaatg 360
acgttgccgt cgctatccat agcaccgacg gcgcgtccgc agacagggaa cggacgcgcc 420
cgatcattaa gataaaggcg gctttttta ttgcaaaacg gtaacggtga ggaaccgttt 480
caccgtcggc gtcactcagt aacaagtatc catcatgatg cctacatcgg gatcggcgtg 540
ggcatccgtt gcagatactt ttgcgaacac ctgacatgaa tgaggaaacg aaattatgca 600
aattacgatc aaagcgcaca tcggcggtga tttgggcgtc tccggtctgg ggctgggtgc 660
tcagggactg aaaggactga attccgcggc ttcatcgctg ggttccagcg tggataaact 720
gagcagcacc atcgataagt tgacctccgc gctgacttcg atgatgtttg gcggcgcgct 780
ggcgcagggg ctgggcgcca gctcgaaggg gctggggatg agcaatcaac tgggccagtc 840
tttcggcaat ggcgcgcagg gtgcgagcaa cctgctatcc gtaccgaaat ccggcggcga 900
tgcgttgtca aaaatgtttg ataaagcgct ggacgatctg ctgggtcatg acaccgtgac 960
caagctgact aaccagagca accaactggc taattcaatg ctgaacgcca gccagatgac 1020
ccagggtaat atgaatgcgt tcggcagcgg tgtgaacaac gcactgtcgt ccattctcgg 1080
caacggtctc ggccagtcga tgagtggctt ctctcagcct tctctggggg caggcggctt 1140
gcagggcctg agcggcgcgg gtgcattcaa ccagttgggt aatgccatcg gcatgggcgt 1200
ggggcagaat gctgcgctga gtgcgttgag taacgtcagc acccacgtag acggtaacaa 1260
ccgccacttt gtagataaag aagatcgcgg catggcgaaa gagatcggcc agtttatgga 1320

-continued tcagtatccg gaaatattcg gtaaaccgga ataccagaaa gatggctgga gttcgccgaa 1380
gacggacgac aaatcctggg ctaaagcgct gagtaaaccg gatgatgacg gtatgaccgg 1440
cgccagcatg gacaaattcc gtcaggcgat gggtatgatc aaaagcgcgg tggcgggtga 1500
taccggcaat accaacctga acctgcgtgg cgcgggcggt gcatcgctgg gtatcgatgc 1560
ggctgtcgtc ggcgataaaa tagccaacat gtcgctgggt aagctggcca acgcctgata 1620
atctgtgctg gcctgataaa gcggaaacga aaaaagagac ggggaagcct gtctcttttc 1680
ttattatgcg gtttatgcgg ttacctggac cggttaatca tcgtcatcga tctggtacaa 1740
acgcacattt tcccgttcat tcgcgtcgtt acgcgccaca atcgcgatgg catcttcctc 1800
gtcgctcaga ttgcgcggct gatggggaac gccgggtgga atatagagaa actcgccggc 1860
cagatggaga cacgtctgcg ataaatctgt gccgtaacgt gtttctatcc gcccctttag 1920
cagatagatt gcggtttcgt aatcaacatg gtaatgcggt tccgcctgtg cgccggccgg 1980
gatcaccaca atattcatag aaagctgtct tgcacctacc gtatcgcggg agataccgac 2040
aaaatagggc agtttttgcg tggtatccgt ggggtgttcc ggcctgacaa tcttgagttg 2100
gttcgtcatc atctttctcc atctgggcga cctgatcggt t 2141

<210> SEQ ID NO 23
<211> LENGTH: 403
<212> TYPE: PRT
<213> ORGANISM: Erwinia amylovora

<400> SEQUENCE: 23

Met Ser Leu Asn Thr Ser Gly Leu Gly Ala Ser Thr Met Gln Ile Ser
1 5 10 15

Ile Gly Gly Ala Gly Gly Asn Asn Gly Leu Leu Gly Thr Ser Arg Gln
20 25 30

Asn Ala Gly Leu Gly Gly Asn Ser Ala Leu Gly Leu Gly Gly Gly Asn
35 40 45

Gln Asn Asp Thr Val Asn Gln Leu Ala Gly Leu Leu Thr Gly Met Met
50 55 60

Met Met Met Ser Met Met Gly Gly Gly Gly Leu Met Gly Gly Gly Leu
65 70 75 80

Gly Gly Gly Leu Gly Asn Gly Leu Gly Gly Ser Gly Gly Leu Gly Glu
85 90 95

Gly Leu Ser Asn Ala Leu Asn Asp Met Leu Gly Gly Ser Leu Asn Thr
100 105 110

Leu Gly Ser Lys Gly Gly Asn Asn Thr Thr Ser Thr Thr Asn Ser Pro
115 120 125

Leu Asp Gln Ala Leu Gly Ile Asn Ser Thr Ser Gln Asn Asp Asp Ser
130 135 140

Thr Ser Gly Thr Asp Ser Thr Ser Asp Ser Ser Asp Pro Met Gln Gln
145 150 155 160

Leu Leu Lys Met Phe Ser Glu Ile Met Gln Ser Leu Phe Gly Asp Gly
165 170 175

Gln Asp Gly Thr Gln Gly Ser Ser Ser Gly Gly Lys Gln Pro Thr Glu
180 185 190

Gly Glu Gln Asn Ala Tyr Lys Lys Gly Val Thr Asp Ala Leu Ser Gly
195 200 205

Leu Met Gly Asn Gly Leu Ser Gln Leu Leu Gly Asn Gly Gly Leu Gly
210 215 220

Gly Gly Gln Gly Gly Asn Ala Gly Thr Gly Leu Asp Gly Ser Ser Leu

-continued

```
225                 230                 235                 240

Gly Gly Lys Gly Leu Gln Asn Leu Ser Gly Pro Val Asp Tyr Gln Gln
                245                 250                 255

Leu Gly Asn Ala Val Gly Thr Gly Ile Gly Met Lys Ala Gly Ile Gln
            260                 265                 270

Ala Leu Asn Asp Ile Gly Thr His Arg His Ser Ser Thr Arg Ser Phe
        275                 280                 285

Val Asn Lys Gly Asp Arg Ala Met Ala Lys Glu Ile Gly Gln Phe Met
    290                 295                 300

Asp Gln Tyr Pro Glu Val Phe Gly Lys Pro Gln Tyr Gln Lys Gly Pro
305                 310                 315                 320

Gly Gln Glu Val Lys Thr Asp Asp Lys Ser Trp Ala Lys Ala Leu Ser
                325                 330                 335

Lys Pro Asp Asp Asp Gly Met Thr Pro Ala Ser Met Glu Gln Phe Asn
            340                 345                 350

Lys Ala Lys Gly Met Ile Lys Arg Pro Met Ala Gly Asp Thr Gly Asn
        355                 360                 365

Gly Asn Leu Gln Ala Arg Gly Ala Gly Gly Ser Ser Leu Gly Ile Asp
    370                 375                 380

Ala Met Met Ala Gly Asp Ala Ile Asn Asn Met Ala Leu Gly Lys Leu
385                 390                 395                 400

Gly Ala Ala


<210> SEQ ID NO 24
<211> LENGTH: 1288
<212> TYPE: DNA
<213> ORGANISM: Erwinia amylovora

<400> SEQUENCE: 24

aagcttcggc atggcacgtt tgaccgttgg gtcggcaggg tacgtttgaa ttattcataa     60

gaggaatacg ttatgagtct gaatacaagt gggctgggag cgtcaacgat gcaaatttct    120

atcggcggtg cgggcggaaa taacgggttg ctgggtacca gtcgccagaa tgctgggttg    180

ggtggcaatt ctgcactggg gctgggcggc ggtaatcaaa atgataccgt caatcagctg    240

gctggcttac tcaccggcat gatgatgatg atgagcatga tgggcggtgg tgggctgatg    300

ggcggtggct taggcggtgg cttaggtaat ggcttgggtg gctcaggtgg cctgggcgaa    360

ggactgtcga acgcgctgaa cgatatgtta ggcggttcgc tgaacacgct gggctcgaaa    420

ggcggcaaca ataccacttc aacaacaaat tccccgctgg accaggcgct gggtattaac    480

tcaacgtccc aaaacgacga ttccacctcc ggcacagatt ccacctcaga ctccagcgac    540

ccgatgcagc agctgctgaa gatgttcagc gagataatgc aaagcctgtt tggtgatggg    600

caagatggca cccagggcag ttcctctggg ggcaagcagc cgaccgaagg cgagcagaac    660

gcctataaaa aaggagtcac tgatgcgctg tcgggcctga tgggtaatgg tctgagccag    720

ctccttggca acgggggact gggaggtggt cagggcggta atgctggcac gggtcttgac    780

ggttcgtcgc tgggcggcaa agggctgcaa aacctgagcg ggccggtgga ctaccagcag    840

ttaggtaacg ccgtgggtac cggtatcggt atgaaagcgg gcattcaggc gctgaatgat    900

atcggtacgc acaggcacag ttcaacccgt tctttcgtca ataaaggcga tcgggcgatg    960

gcgaaggaaa tcggtcagtt catggaccag tatcctgagg tgtttggcaa gccgcagtac   1020

cagaaaggcc cgggtcagga ggtgaaaacc gatgacaaat catgggcaaa agcactgagc   1080

aagccagatg acgacggaat gacaccagcc agtatggagc agttcaacaa agccaagggc   1140
```

-continued

```
atgatcaaaa ggcccatggc gggtgatacc ggcaacggca acctgcaggc acgcggtgcc   1200

ggtggttctt cgctgggtat tgatgccatg atggccggtg atgccattaa caatatggca   1260

cttggcaagc tgggcgcggc ttaagctt                                      1288


<210> SEQ ID NO 25
<211> LENGTH: 341
<212> TYPE: PRT
<213> ORGANISM: Pseudomonas syringae

<400> SEQUENCE: 25

Met Gln Ser Leu Ser Leu Asn Ser Ser Ser Leu Gln Thr Pro Ala Met
  1               5                  10                  15

Ala Leu Val Leu Val Arg Pro Glu Ala Glu Thr Thr Gly Ser Thr Ser
             20                  25                  30

Ser Lys Ala Leu Gln Glu Val Val Val Lys Leu Ala Glu Glu Leu Met
         35                  40                  45

Arg Asn Gly Gln Leu Asp Asp Ser Ser Pro Leu Gly Lys Leu Leu Ala
     50                  55                  60

Lys Ser Met Ala Ala Asp Gly Lys Ala Gly Gly Gly Ile Glu Asp Val
 65                  70                  75                  80

Ile Ala Ala Leu Asp Lys Leu Ile His Glu Lys Leu Gly Asp Asn Phe
                 85                  90                  95

Gly Ala Ser Ala Asp Ser Ala Ser Gly Thr Gly Gln Gln Asp Leu Met
            100                 105                 110

Thr Gln Val Leu Asn Gly Leu Ala Lys Ser Met Leu Asp Asp Leu Leu
        115                 120                 125

Thr Lys Gln Asp Gly Gly Thr Ser Phe Ser Glu Asp Asp Met Pro Met
    130                 135                 140

Leu Asn Lys Ile Ala Gln Phe Met Asp Asp Asn Pro Ala Gln Phe Pro
145                 150                 155                 160

Lys Pro Asp Ser Gly Ser Trp Val Asn Glu Leu Lys Glu Asp Asn Phe
                165                 170                 175

Leu Asp Gly Asp Glu Thr Ala Ala Phe Arg Ser Ala Leu Asp Ile Ile
            180                 185                 190

Gly Gln Gln Leu Gly Asn Gln Gln Ser Asp Ala Gly Ser Leu Ala Gly
        195                 200                 205

Thr Gly Gly Gly Leu Gly Thr Pro Ser Ser Phe Ser Asn Asn Ser Ser
    210                 215                 220

Val Met Gly Asp Pro Leu Ile Asp Ala Asn Thr Gly Pro Gly Asp Ser
225                 230                 235                 240

Gly Asn Thr Arg Gly Glu Ala Gly Gln Leu Ile Gly Glu Leu Ile Asp
                245                 250                 255

Arg Gly Leu Gln Ser Val Leu Ala Gly Gly Gly Leu Gly Thr Pro Val
            260                 265                 270

Asn Thr Pro Gln Thr Gly Thr Ser Ala Asn Gly Gly Gln Ser Ala Gln
        275                 280                 285

Asp Leu Asp Gln Leu Leu Gly Gly Leu Leu Leu Lys Gly Leu Glu Ala
    290                 295                 300

Thr Leu Lys Asp Ala Gly Gln Thr Gly Thr Asp Val Gln Ser Ser Ala
305                 310                 315                 320

Ala Gln Ile Ala Thr Leu Leu Val Ser Thr Leu Leu Gln Gly Thr Arg
                325                 330                 335

Asn Gln Ala Ala Ala
```

-continued

340

<210> SEQ ID NO 26
<211> LENGTH: 1026
<212> TYPE: DNA
<213> ORGANISM: Pseudomonas syringae

<400> SEQUENCE: 26
atgcagagtc tcagtcttaa cagcagctcg ctgcaaaccc cggcaatggc ccttgtcctg 60
gtacgtcctg aagccgagac gactggcagt acgtcgagca aggcgcttca ggaagttgtc 120
gtgaagctgg ccgaggaact gatgcgcaat ggtcaactcg acgacagctc gccattggga 180
aaactgttgg ccaagtcgat ggccgcagat ggcaaggcgg gcggcggtat tgaggatgtc 240
atcgctgcgc tggacaagct gatccatgaa aagctcggtg acaacttcgg cgcgtctgcg 300
gacagcgcct cgggtaccgg acagcaggac ctgatgactc aggtgctcaa tggcctggcc 360
aagtcgatgc tcgatgatct tctgaccaag caggatggcg ggacaagctt ctccgaagac 420
gatatgccga tgctgaacaa gatcgcgcag ttcatggatg acaatcccgc acagtttccc 480
aagccggact cgggctcctg ggtgaacgaa ctcaaggaag acaacttcct tgatggcgac 540
gaaacggctg cgttccgttc ggcactcgac atcattggcc agcaactggg taatcagcag 600
agtgacgctg gcagtctggc agggacgggt ggaggtctgg gcactccgag cagtttttcc 660
aacaactcgt ccgtgatggg tgatccgctg atcgacgcca ataccggtcc cggtgacagc 720
ggcaataccc gtggtgaagc ggggcaactg atcggcgagc ttatcgaccg tggcctgcaa 780
tcggtattgg ccggtggtgg actgggcaca cccgtaaaca ccccgcagac cggtacgtcg 840
gcgaatggcg gacagtccgc tcaggatctt gatcagttgc tgggcggctt gctgctcaag 900
ggcctggagg caacgctcaa ggatgccggg caaacaggca ccgacgtgca gtcgagcgct 960
gcgcaaatcg ccaccttgct ggtcagtacg ctgctgcaag gcacccgcaa tcaggctgca 1020
gcctga 1026

<210> SEQ ID NO 27
<211> LENGTH: 344
<212> TYPE: PRT
<213> ORGANISM: Pseudomonas solanacearum

<400> SEQUENCE: 27

Met Ser Val Gly Asn Ile Gln Ser Pro Ser Asn Leu Pro Gly Leu Gln
1 5 10 15

Asn Leu Asn Leu Asn Thr Asn Thr Asn Ser Gln Gln Ser Gly Gln Ser
20 25 30

Val Gln Asp Leu Ile Lys Gln Val Glu Lys Asp Ile Leu Asn Ile Ile
35 40 45

Ala Ala Leu Val Gln Lys Ala Ala Gln Ser Ala Gly Gly Asn Thr Gly
50 55 60

Asn Thr Gly Asn Ala Pro Ala Lys Asp Gly Asn Ala Asn Ala Gly Ala
65 70 75 80

Asn Asp Pro Ser Lys Asn Asp Pro Ser Lys Ser Gln Ala Pro Gln Ser
85 90 95

Ala Asn Lys Thr Gly Asn Val Asp Asp Ala Asn Asn Gln Asp Pro Met
100 105 110

Gln Ala Leu Met Gln Leu Leu Glu Asp Leu Val Lys Leu Leu Lys Ala
115 120 125

Ala Leu His Met Gln Gln Pro Gly Gly Asn Asp Lys Gly Asn Gly Val

-continued

```
    130                 135                 140

Gly Gly Ala Asn Gly Ala Lys Gly Ala Gly Gly Gln Gly Gly Leu Ala
145                 150                 155                 160

Glu Ala Leu Gln Glu Ile Glu Gln Ile Leu Ala Gln Leu Gly Gly Gly
                165                 170                 175

Gly Ala Gly Ala Gly Gly Ala Gly Gly Gly Val Gly Gly Ala Gly Gly
            180                 185                 190

Ala Asp Gly Gly Ser Gly Ala Gly Gly Ala Gly Gly Ala Asn Gly Ala
        195                 200                 205

Asp Gly Gly Asn Gly Val Asn Gly Asn Gln Ala Asn Gly Pro Gln Asn
    210                 215                 220

Ala Gly Asp Val Asn Gly Ala Asn Gly Ala Asp Asp Gly Ser Glu Asp
225                 230                 235                 240

Gln Gly Gly Leu Thr Gly Val Leu Gln Lys Leu Met Lys Ile Leu Asn
                245                 250                 255

Ala Leu Val Gln Met Met Gln Gln Gly Gly Leu Gly Gly Gly Asn Gln
            260                 265                 270

Ala Gln Gly Gly Ser Lys Gly Ala Gly Asn Ala Ser Pro Ala Ser Gly
        275                 280                 285

Ala Asn Pro Gly Ala Asn Gln Pro Gly Ser Ala Asp Asp Gln Ser Ser
    290                 295                 300

Gly Gln Asn Asn Leu Gln Ser Gln Ile Met Asp Val Val Lys Glu Val
305                 310                 315                 320

Val Gln Ile Leu Gln Gln Met Leu Ala Ala Gln Asn Gly Gly Ser Gln
                325                 330                 335

Gln Ser Thr Ser Thr Gln Pro Met
            340
```

<210> SEQ ID NO 28
<211> LENGTH: 1035
<212> TYPE: DNA
<213> ORGANISM: Pseudomonas solanacearum

<400> SEQUENCE: 28

```
atgtcagtcg gaaacatcca gagcccgtcg aacctcccgg gtctgcagaa cctgaacctc      60
aacaccaaca ccaacagcca gcaatcgggc cagtccgtgc aagacctgat caagcaggtc     120
gagaaggaca tcctcaacat catcgcagcc ctcgtgcaga aggccgcaca gtcggcgggc     180
ggcaacaccg gtaacaccgg caacgcgccg gcgaaggacg gcaatgccaa cgcgggcgcc     240
aacgacccga gcaagaacga cccgagcaag agccaggctc cgcagtcggc caacaagacc     300
ggcaacgtcg acgacgccaa caaccaggat ccgatgcaag cgctgatgca gctgctggaa     360
gacctggtga agctgctgaa ggcggccctg cacatgcagc agcccggcgg caatgacaag     420
ggcaacggcg tgggcggtgc caacggcgcc aagggtgccg gcggccaggg cggcctggcc     480
gaagcgctgc aggagatcga gcagatcctc gcccagctcg gcggcggcgg tgctggcgcc     540
ggcggcgcgg gtggcggtgt cggcggtgct ggtggcgcgg atggcggctc cggtgcgggt     600
ggcgcaggcg gtgcgaacgg cgccgacggc ggcaatggcg tgaacggcaa ccaggcgaac     660
ggcccgcaga acgcaggcga tgtcaacggt gccaacggcg cggatgacgg cagcgaagac     720
cagggcggcc tcaccggcgt gctgcaaaag ctgatgaaga tcctgaacgc gctggtgcag     780
atgatgcagc aaggcggcct cggcggcggc aaccaggcgc agggcggctc gaagggtgcc     840
ggcaacgcct cgccggcttc cggcgcgaac ccgggcgcga accagcccgg ttcggcggat     900
```

-continued

```
gatcaatcgt ccggccagaa caatctgcaa tcccagatca tggatgtggt gaaggaggtc    960

gtccagatcc tgcagcagat gctggcggcg cagaacggcg gcagccagca gtccacctcg   1020

acgcagccga tgtaa                                                    1035


<210> SEQ ID NO 29
<211> LENGTH: 26
<212> TYPE: PRT
<213> ORGANISM: Xanthomonas campestris pv. glycines

<400> SEQUENCE: 29

Thr Leu Ile Glu Leu Met Ile Val Val Ala Ile Ile Ala Ile Leu Ala
  1               5                  10                  15

Ala Ile Ala Leu Pro Ala Tyr Gln Asp Tyr
             20                  25


<210> SEQ ID NO 30
<211> LENGTH: 20
<212> TYPE: PRT
<213> ORGANISM: Xanthomonas campestris pv. pelargonii

<400> SEQUENCE: 30

Ser Ser Gln Gln Ser Pro Ser Ala Gly Ser Glu Gln Gln Leu Asp Gln
  1               5                  10                  15

Leu Leu Ala Met
             20
```

HYPERSENSITIVE RESPONSE ELICITOR FRAGMENTS ELICITING A HYPERSENSITIVE RESPONSE AND USES THEREOF

This application is a division of U.S. patent application Ser. No. 09/086,118, filed May 28, 1998, now U.S. Pat. No. 6,583,107, issued Jun. 24, 2003, which claims benefit of U.S. Provisional Patent Application Ser. No. 60/048,109, filed May 30, 1997.

FIELD OF THE INVENTION

The present invention relates to fragments of a hypersensitive response elicitor which fragments elicit a hypersensitive response and uses thereof.

BACKGROUND OF THE INVENTION

Interactions between bacterial pathogens and their plant hosts generally fall into two categories: (1) compatible (pathogen-host), leading to intercellular bacterial growth, symptom development, and disease development in the host plant; and (2) incompatible (pathogen-nonhost), resulting in the hypersensitive response, a particular type of incompatible interaction occurring, without progressive disease symptoms. During compatible interactions on host plants, bacterial populations increase dramatically and progressive symptoms occur. During incompatible interactions, bacterial populations do not increase, and progressive symptoms do not occur.

The hypersensitive response is a rapid, localized necrosis that is associated with the active defense of plants against many pathogens (Kiraly, Z., "Defenses Triggered by the Invader: Hypersensitivity," pages 201–224 in: *Plant Disease: An Advanced Treatise,* Vol. 5, J. G. Horsfall and E. B. Cowling, ed. Academic Press New York (1980); Klement, Z., "Hypersensitivity," pages 149–177 in: *Phytopathogenic Prokaryotes,* Vol. 2, M. S. Mount and G. H. Lacy, ed. Academic Press, New York (1982)). The hypersensitive response elicited by bacteria is readily observed as a tissue collapse if high concentrations ($\geqq 10^7$ cells/ml) of a limited host-range pathogen like *Pseudomonas syringae* or *Erwinia amylovora* are infiltrated into the leaves of nonhost plants (necrosis occurs only in isolated plant cells at lower levels of inoculum) (Klement, Z., "Rapid Detection of Pathogenicity of Phytopathogenic Pseudomonads," *Nature* 199: 299–300; Klement, et al., "Hypersensitive Reaction Induced by Phytopathogenic Bacteria in the Tobacco Leaf," *Phytopathology* 54:474–477 (1963); Turner, et al., "The Quantitative Relation Between Plant and Bacterial Cells Involved in the Hypersensitive Reaction," *Phytopathology* 64:885–890 (1974); Klement, Z., "Hypersensitivity," pages 149–177 in *Phytopathogenic Prokaryotes,* Vol. 2., M. S. Mount and G. H. Lacy, ed. Academic Press, New York (1982)). The capacities to elicit the hypersensitive response in a nonhost and be pathogenic in a host appear linked. As noted by Klement, Z., "Hypersensitivity," pages 149–177 in *Phytopathogenic Prokaryotes,* Vol. 2., M. S. Mount and G. H. Lacy, ed. Academic Press, New York, these pathogens also cause physiologically similar, albeit delayed, necroses in their interactions with compatible hosts. Furthermore, the ability to produce the hypersensitive response or pathogenesis is dependent on a common set of genes, denoted hrp (Lindgren, P. B., et al., "Gene Cluster of *Pseudomonas syringae* pv. 'phaseolicola' Controls Pathogenicity of Bean Plants and Hypersensitivity on Nonhost Plants," *J. Bacteriol.* 168:512–22 (1986); Willis, D. K., et al., "hrp Genes of Phytopathogenic Bacteria," *Mol. Plant-Microbe Interact.* 4:132–138 (1991)). Consequently, the hypersensitive response may hold clues to both the nature of plant defense and the basis for bacterial pathogenicity.

The hrp genes are widespread in gram-negative plant pathogens, where they are clustered, conserved, and in some cases interchangeable (Willis, D. K., et al., "hrp Genes of Phytopathogenic Bacteria," *Mol. Plant-Microbe Interact.* 4:132–138 (1991); Bonas, U., "hrp Genes of Phytopathogenic Bacteria," pages 79–98 in: *Current Topics in Microbiology and Immunology: Bacterial Pathogenesis of Plants and Animals—Molecular and Cellular Mechanisms,* J. L. Dangl, ed. Springer-Verlag, Berlin (1994)). Several hrp genes encode components of a protein secretion pathway similar to one used by *Yersinia, Shigella,* and *Salmonella* spp. to secrete proteins essential in animal diseases (Van Gijsegem, et al., "Evolutionary Conservation of Pathogenicity Determinants Among Plant and Animal Pathogenic Bacteria," *Trends Microbiol.* 1:175–180 (1993)). In *E. amylovora, P. syringae,* and *P. solanacearum,* hrp genes have been shown to control the production and secretion of glycine-rich, protein elicitors of the hypersensitive response (He, S. Y., et al. "*Pseudomonas syringae* pv. Syringae $Harpin_{Pss}$: a Protein that is Secreted via the Hrp Pathway and Elicits the Hypersensitive Response in Plants," *Cell* 73:1255–1266 (1993), Wei, Z.-H., et al., "HrpI of *Erwinia amylovora* Functions in Secretion of Harpin and is a Member of a New Protein Family," *J. Bacteriol.* 175:7958–7967 (1993); Arlat, M. et al. "PopA1, a Protein Which Induces a Hypersensitive-like Response on Specific Petunia Genotypes, is Secreted via the Hrp Pathway of *Pseudomonas solanacearum,*" *EMBO J.* 13:543–553 (1994)).

The first of these proteins was discovered in *E. amylovora* Ea321, a bacterium that causes fire blight of rosaceous plants, and was designated harpin (Wei, Z.-M., et al, "Harpin, Elicitor of the Hypersensitive Response Produced by the Plant Pathogen *Erwinia amylovora,*" *Science* 257: 85–88 (1992)). Mutations in the encoding hrpN gene revealed that harpin is required for *E. amylovora* to elicit a hypersensitive response in nonhost tobacco leaves and incite disease symptoms in highly susceptible pear fruit. The *P. solanacearum* GMI1000 PopA1 protein has similar physical properties and also elicits the hypersensitive response in leaves of tobacco, which is not a host of that strain (Arlat, et al. "PopA1, a Protein Which Induces a Hypersensitive-like Response on Specific Petunia Genotypes, is Secreted via the Hrp Pathway of *Pseudomonas solanacearum,*" *EMBO J.* 13:543–53 (1994)). However, *P. solanacearum* popA mutants still elicit the hypersensitive response in tobacco and incite disease in tomato. Thus, the role of these glycine-rich hypersensitive response elicitors can vary widely among gram-negative plant pathogens.

Other plant pathogenic hypersensitive response elicitors have been isolated, cloned, and sequenced. These include: *Erwinia chrysanthemi* (Bauer, et. al., "*Erwinia chrysanthemi* $Harpin_{Ech}$: Soft-Rot Pathogenesis," *MPMI* 8(4): 484–91 (1995)); *Erwinia carotovora* (Cui, et. al., "The RsmA⁻ Mutants of *Erwinia carotovora* subsp. *carotovora* Strain Ecc71 Overexpress $hrpN_{Ecc}$ and Elicit a Hypersensitive Reaction-like Response in Tobacco Leaves," *MPMI* 9(7): 565–73 (1966)); *Erwinia stewartii* (Ahmad, et. al., "Harpin is not Necessary for the Pathogenicity of *Erwinia stewartii* on Maize," *8th Int'l. Cong. Molec. Plant-Microb. Inter.* Jul. 14–19, 1996 and Ahmad, et. al., "Harpin is not Necessary for the Pathogenicity of *Erwinia stewartii* on Maize," *Ann. Mtg.*

*Am. Phytopath. Soc.* Jul. 27–31, 1996); and *Pseudomonas syringae* pv. *syringae* (WO 94/26782 to Cornell Research Foundation, Inc.).

The present invention seeks to identify fragments of hypersensitive response elicitor proteins or polypeptides, which fragments elicit a hypersensitive response, and uses of such fragments.

SUMMARY OF THE INVENTION

The present invention is directed to an isolated fragment of an *Erwinia* hypersensitive response elicitor protein or polypeptide where the fragment elicits a hypersensitive response in plants. Also disclosed are isolated DNA molecules which encode such fragments.

The fragments of hypersensitive response elicitors can be used to impart disease resistance to plants, to enhance plant growth, and/or to control insects. This involves applying the fragments in a non-infectious form to plants or plant seeds under conditions effective to impart disease resistance, to enhance plant growth, and/or to control insects on plants or plants grown from the plant seeds.

As an alternative to applying the fragments to plants or plant seeds in order to impart disease resistance, to enhance plant growth, and/or to control insects on plants, transgenic plants or plant seeds can be utilized. When utilizing transgenic plants, this involves providing a transgenic plant transformed with a DNA molecule encoding a fragment of a hypersensitive response elicitor protein or polypeptide which fragments elicit a hypersensitive response in plants and growing the plant under conditions effective to impart disease resistance, to enhance plant growth, and/or to control insects in the plants or plants grown from the plant seeds. Alternatively, a transgenic plant seed transformed with the DNA molecule encoding such a fragment can be provided and planted in soil. A plant is then propagated under conditions effective to impart disease resistance, to enhance plant growth, and/or to control insects on plants or plants grown from the plant seeds.

BRIEF DESCRIPTION OF THE DRAWINGS

FIG. 8 shows the similarities near N-termini among harpins of *Erwinia* spp. Underlined residues are present (identical or similar) in at least four out of the five proteins examined. Nine out of the first 26 residues are conserved in this manner.

FIG. 11 shows a list of synthesized oligonucleotide primers for construction of truncated harpin proteins. N represents the N-terminus (5' region), and C represents the C-terminus (3' region). The primers correspond to the indicated sequence identification numbers for the present application: N1 (SEQ. ID. No. 1), N76 (SEQ. ID. No. 2), N99 (SEQ. ID. No. 3), N105 (SEQ. ID. No. 4), N110 (SEQ. ID. No. 5), N137 (SEQ. ID. No. 6), N150 (SEQ. ID. No. 7), N169 (SEQ. ID. No. 8), N210 (SEQ. ID. No. 9), N267 (SEQ. ID. No. 10), N343 (SEQ. ID. No. 11), C75 (SEQ. ID. No. 12), C104 (SEQ. ID. No. 13), C168 (SEQ. ID. No. 14), C180 (SEQ. ID. No. 15), C204 (SEQ. ID. No. 16), C209 (SEQ. ID. No. 17), C266 (SEQ. ID. No. 18), C342 (SEQ. ID. No. 19), and C403 (SEQ. ID. No. 20).

DETAILED DESCRIPTION OF THE INVENTION

Figure 1:
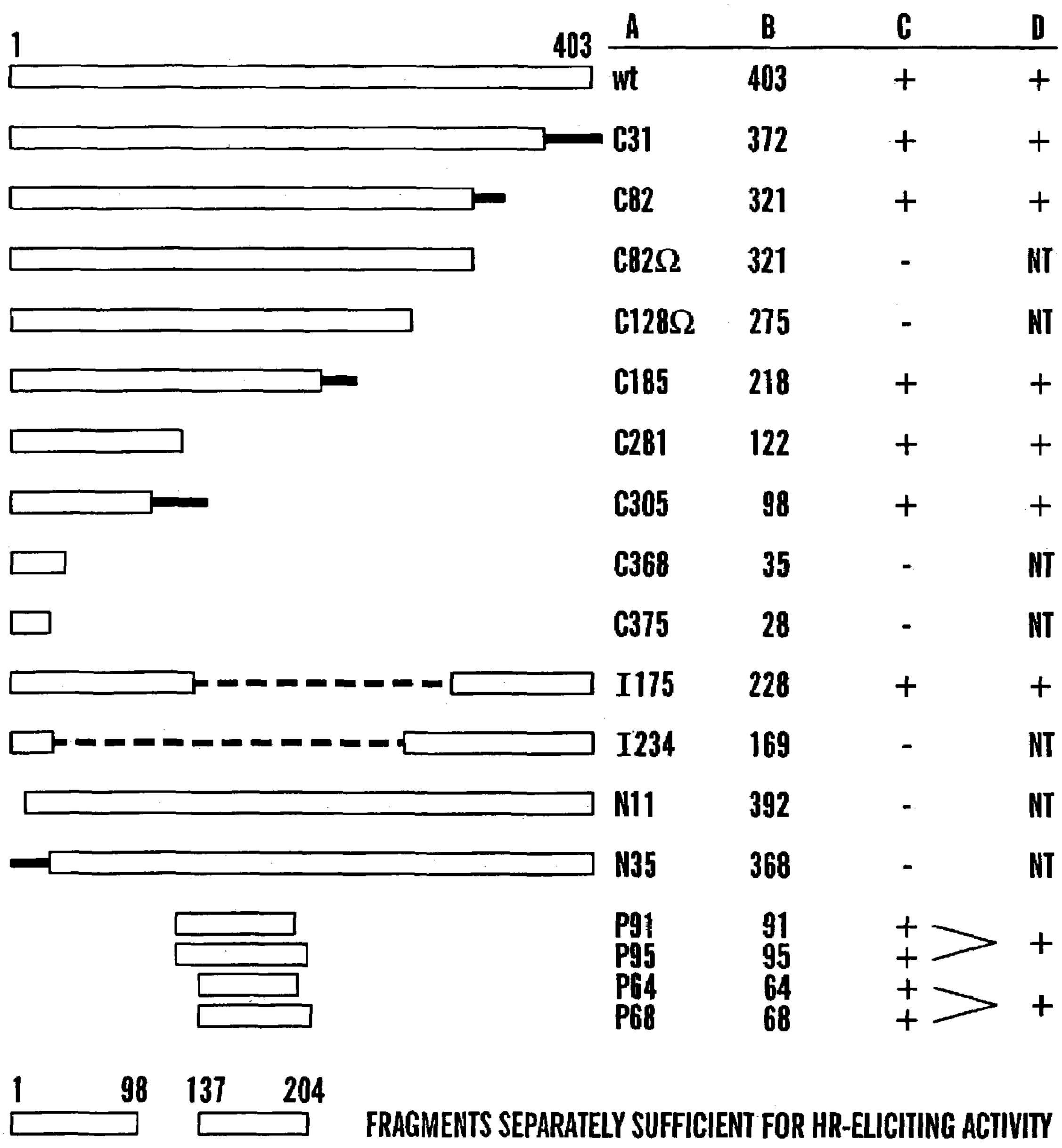
FIG. 1 shows a deletion and proteolysis analysis for the *Erwinia amylovora* hypersensitive response elicitor (i.e. harpin). A is the name of the harpin fragment. B is the length of the fragment in amino acid residues. C indicates whether detectable protein is produced. D states whether there is hypersensitive response (i.e., HR) eliciting activity. The solid line indicates that there are additional amino acids which are not harpin encoded, while the dashed line indicates the portion of the harpin that is deleted. The numbers above the fragments in the box represent the amino acid residue present at the end of a given fragment; residue #1 is the N-terminus, and residue #403 is the C-terminus.

The present invention is directed to isolated fragments of a hypersensitive response elicitor protein or polypeptide where the fragments elicit a hypersensitive response in plants. Also disclosed are DNA molecules encoding such fragments as well as expression systems, host cells, and plants containing such molecules. Uses of the fragments themselves and the DNA molecules encoding them are disclosed.

The fragments of hypersensitive response elicitor polypeptides or proteins according to the present invention are derived from hypersensitive response elicitor polypeptides or proteins of a wide variety of fungal and bacterial pathogens. Such polypeptides or proteins are able to elicit local necrosis in plant tissue contacted by the elicitor. Examples of suitable bacterial sources of polypeptide or protein elicitors include *Erwinia, Pseudomonas,* and *Xanthamonas* species (e.g., the following bacteria: *Erwinia amylovora, Erwinia chrysanthemi, Erwinia stewartii, Erwinia carotovora, Pseudomonas syringae, Pseudomonas solancearum, Xanthomonas campestris,* and mixtures thereof).

An example of a fungal source of a hypersensitive response elicitor protein or polypeptide is *Phytophthora.* Suitable species of *Phytophthora* include *Phytophthora parasitica, Phytophthora cryptogea, Phytophthora cinnamomi, Phytophthora capsici, Phytophthora megasperma,* and *Phytophthora citrophthora.*

The hypersensitive response elicitor polypeptide or protein from *Erwinia chrysanthemi* has an amino acid sequence corresponding to SEQ. ID. No. 21 as follows:

```
Met Gln Ile Thr Ile Lys Ala His Ile Gly Gly Asp Leu Gly Val Ser
1               5                   10                  15

Gly Leu Gly Ala GLn Gly Leu Lys Gly Leu Asn Ser Ala Ala Ser Ser
            20                  25                  30

Leu Gly Ser Ser Val Asp Lys Leu Ser Ser Thr Ile Asp Lys Leu Thr
        35                  40                  45

Ser Ala Leu Thr Ser Met Met Phe Gly Gly Ala Leu Ala Gln Gly Leu
    50                  55                  60

Gly Ala Ser Ser Lys Gly Leu Gly Met Ser Asn Gln Leu Gly Gln Ser
65                  70                  75                  80

Phe Gly Asn Gly Ala Gln Gly Ala Ser Asn Leu Leu Ser Val Pro Lys
                85                  90                  95

Ser Gly Gly Asp Ala Leu Ser Lys Met Phe Asp Lys Ala Leu Asp Asp
            100                 105                 110

Leu Leu Gly His Asp Thr Val Thr Lys Leu Thr Asn Gln Ser Asn Gln
        115                 120                 125

Leu Ala Asn Ser Met Leu Asn Ala Ser Gln Met Thr Gln Gly Asn Met
    130                 135                 140

Asn Ala Phe Gly Ser Gly Val Asn Asn Ala Leu Ser Ser Ile Leu Gly
145                 150                 155                 160

Asn Gly Leu Gly Gln Ser Met Ser Gly Phe Ser Gln Pro Ser Leu Gly
                165                 170                 175

Ala Gly Gly Leu Gln Gly Leu Ser Gly Ala Gly Ala Phe Asn Gln Leu
            180                 185                 190

Gly Asn Ala Ile Gly Met Gly Val Gly Gln Asn Ala Ala Leu Ser Ala
        195                 200                 205

Leu Ser Asn Val Ser Thr His Val Asp Gly Asn Asn Arg His Phe Val
    210                 215                 220

Asp Lys Glu Asp Arg Gly Met Ala Lys Gln Ile Gly Gln Phe Met Asp
225                 230                 235                 240

Gln Tyr Pro Gln Ile Phe Gly Lys Pro Gln Tyr Gln Lys Asp Gly Trp
                245                 250                 255

Ser Ser Pro Lys Thr Asp Asp Lys Ser Trp Ala Lys Ala Leu Ser Lys
            260                 265                 270

Pro Asp Asp Asp Gly Met Thr Gly Ala Ser Met Asp Lys Phe Arg Gln
        275                 280                 285

Ala Met Gly Met Ile Lys Ser Ala Val Ala Gly Asp Thr Gly Asn Thr
    290                 295                 300
```

-continued

Asn Leu Asn Leu Arg Gly Ala Gly Gly Ala Ser Len Gly Ile Asp Ala
305 310 315 320

Ala Val Val Gly Asp Lys Ile Ala Asn Met Ser Leu Gly Lys Leu Ala
325 330 335

Asn Ala

This hypersensitive response elicitor polypeptide or protein has a molecular weight of 34 kDa, is heat stable, has a glycine content of greater than 16%, and contains substantially no cysteine. The *Erwinia chrysanthemi* hypersensitive response elicitor polypeptide or protein is encoded by a DNA molecule having a nucleotide sequence corresponding to SEQ. ID. No. 22 as follows:

```
CGATTTTACC CGGGTGAACG TCCTATGACC GACAGCATCA CGGTATTCGA CACCGTTACG   60
GCGTTTATGG CCGCGATGAA CCGGCATCAG GCGGCGCGCT GGTCGCCGCA ATCCGGCGTC  120
GATCTGGTAT TTCAGTTTGG GGACACCGGG CGTGAACTCA TGATGCAGAT TCAGCCCGGG  180
CAGCAATATC CCGGCATGTT GCGCACGCTC CTCGCTCGTC GTTATCAGCA GGCGGCAGAG  240
TGCGATGGCT GCCATCTGTG CCTGAACGGC AGCGATGTAT TGATCCTCTG GTGGCCGCTG  300
CCGTCGGATC CCGGCAGTTA TCCGCAGGTG ATCGAACGTT TGTTTGAACT GGCGGGAATG  360
ACGTTGCCGT CGCTATCCAT AGCACCGACG GCGCGTCCGC AGACAGGGAA CGCACGCGCC  420
CGATCATTAA GATAAAGGCG GCTTTTTTTA TTCCAAAACG GTAACGGTGA GGAACCGTTT  480
CACCGTCGGC GTCACTCACT AACAAGTATC CATCATGATG CCTACATCGC GATCGGCGTG  540
GGCATCCGTT GCAGATACTT TTCCGAACAC CTGACATGAA TGAGGAAACG AAATTATGCA  600
AATTACCATC AAAGCGCACA TCGGCGGTGA TTTGGGCGTC TCCGGTCTGG GGCTGGGTCC  660
TCAGGGACTG AAAGGACTGA ATTCCGCCGC TTCATCGCTG GGTTCCAGCG TGGATAAACT  720
GAGCAGCACC ATCGATAAGT TGACCTCCGC CCTGACTTCC ATGATGTTTG GCGGCCCGCT  780
GGCGCAGCGG CTGGGCGCCA GCTCGAAGGG GCTGGGGATG AGCAATCAAC TGGGCCAGTC  840
TTTCCGCAAT GGCGCGCAGG GTGCGAGCAA CCTGCTATCC GTACCGAAAT CCGGCGGCGA  900
TGCGTTGTCA AAAATGTTTG ATAAAGCGCT GGACGATCTG CTGGGTCATG ACACCGTGAC  960
CAAGCTGACT AACCACAGCA ACCAACTGGC TAATTCAATG CTCAACGCCA GCCAGATOAC 1020
CCAGGGTAAT ATGAATGCGT TCGGCAGCGG TGTGAACAAC GCACTGTCGT CCATTCTCGG 1080
CAACGGTCTC GGCCAGTCGA TGAGTGGCTT CTCTCAGCCT TCTCTGGGGG CAGGCGGCTT 1140
GCAGGGCCTG AGCGGCGCGG GTGCATTCAA CCAGTTGGGT AATGCCATCG GCATGGGCGT 1200
GGCGCAGAAT GCTGCGCTGA GTGCGTTGAG TAACGTCAGC ACCCACGTAG ACGGTAACAA 1260
CCGCCACTTT GTAGATAAAG AAGATCGCGG CATGGCGAAA GAGATCGGCC AGTTTATGGA 1320
TCAGTATCCG GAAATATTCG GTAAACCGGA ATACCAGAAA GATGGCTGGA GTTCGCCGAA 1380
GACGGACGAC AAATCCTGGG CTAAAGCGCT GAGTAAACCG GATGATGACG GTATGACCGG 1440
CGCCAGCATG GACAAATTCC GTCAGGCGAT GGGTATGATC AAAAGCGCGG TGGCGGGTGA 1500
TACCGGCAAT ACCAACCTGA ACCTGCGTGG CGCGGGCGGT GCATCGCTGG GTATCGATGC 1560
GGCTGTCGTC GGCGATAAAA TAGCCAACAT GTCGCTGGGT AAGCTGGCCA ACGCCTGATA 1620
ATCTGTGCTG GCCTGATAAA GCGGAAACGA AAAAAGAGAC GGGGAAGCCT GTCTCTTTTC 1680
TTATTATGCG GTTTATGCGG TTACCTGGAC CGGTTAATCA TCGTCATCGA TCTGGTACAA 1740
```

-continued

```
ACGCACATTT TCCCCTTCAT TCGCGTCGTT ACGCGCCACA ATCGCGATGG CATCTTCCTC  1800

GTCGCTCAGA TTGCGCGGCT GATGGGGAAC GCCGGGTGGA ATATAGAGAA ACTCGCCGGC  1860

CAGATGGAGA CACGTCTGCG ATAAATCTGT GCCGTAACGT GTTTCTATCC GCCCCTTTAG  1920

CAGATAGATT GCGGTTTCGT AATCAACATG GTAATGCGGT TCCGCCTGTG CGCCGGCCGG  1980

GATCACCACA ATATTCATAG AAAGCTGTCT TGCACCTACC GTATCGCGGG AGATACCGAC  2040

AAAATAGGGC AGTTTTTGCG TGGTATCCGT GGGGTGTTCC GGCCTGACAA TCTTGAGTTG  2100

GTTCCTCATC ATCTTTCTCC ATCTGGGCGA CCTGATCCGT T                      2141
```

The hypersensitive response elicitor polypeptide or protein derived from *Erwinia amylovora* has an amino acid sequence corresponding to SEQ. ID. No. 23 as follows:

```
Met Ser Leu Asn Thr Ser Gly Leu Gly Ala Ser Thr Met Gln Ile Ser
1               5                   10                  15

Ile Gly Gly Ala Gly Gly Asn Asn Gly Leu Leu Gly Thr Ser Arg Gln
            20                  25                  30

Asn Ala Gly Leu Gly Gly Asn Ser Ala Leu Gly Leu Gly Gly Gly Asn
        35                  40                  45

Gln Asn Asp Thr Val Asn Gln Leu Ala Gly Leu Leu Thr Gly Met Met
    50                  55                  60

Met Met Met Ser Met Met Gly Gly Gly Gly Leu Met Gly Gly Gly Leu
65                  70                  75                  80

Gly Gly Gly Leu Gly Asn Gly Leu Gly Gly Ser Gly Gly Leu Gly Glu
                85                  90                  95

Gly Leu Ser Asn Ala Leu Asn Asp Met Leu Gly Gly Ser Leu Asn Thr
            100                 105                 110

Leu Gly Ser Lys Gly Gly Asn Asn Thr Thr Ser Thr Thr Asn Ser Pro
        115                 120                 125

Leu Asp Gln Ala Leu Gly Ile Asn Ser Thr Ser Gln Asn Asp Asp Ser
    130                 135                 140

Thr Ser Gly Thr Asp Ser Thr Ser Asp Ser Ser Asp Pro Met Gln Gln
145                 150                 155                 160

Leu Leu Lys Met Phe Ser Glu Ile Met Gln Ser Leu Phe Gly Asp Gly
                165                 170                 175

Gln Asp Gly Thr Gln Gly Ser Ser Ser Gly Gly Lys Gln Pro Thr Glu
            180                 185                 190

Gly Glu Gln Asn Ala Tyr Lys Lys Gly Val Thr Asp Ala Leu Ser Gly
        195                 200                 205

Leu Met Gly Asn Gly Leu Ser Gln Leu Leu Gly Asn Gly Gly Leu Gly
    210                 215                 220

Gly Gly Gln Gly Gly Asn Ala Gly Thr Gly Leu Asp Gly Ser Ser Leu
225                 230                 235                 240

Gly Gly Lys Gly Leu Gln Asn Leu Ser Gly Pro Val Asp Tyr Gln Gln
                245                 250                 255

Leu Gly Asn Ala Val Gly Thr Gly Ile Gly Met Lys Ala Gly Ile Gln
            260                 265                 270

Ala Leu Asn Asp Ile Gly Thr His Arg His Ser Ser Thr Arg Ser Phe
        275                 280                 285

Val Asn Lys Gly Asp Arg Ala Met Ala Lys Glu Ile Gly Gln Phe Met
    290                 295                 300
```

-continued

```
Asp Gln Tyr Pro Glu Val Phe Gly Lys Pro Gln Tyr Gln Lys Gly Pro
305                 310                 315                 320

Gly Gln Glu Val Lys Thr Asp Asp Lys Ser Trp Ala Lys Ala Leu Ser
                325                 330                 335

Lys Pro Asp Asp Asp Gly Met Thr Pro Ala Ser Met Glu Gln Phe Asn
            340                 345                 350

Lys Ala Lys Gly Met Ile Lys Arg Pro Met Ala Gly Asp Thr Gly Asn
        355                 360                 365

Gly Asn Leu Gln Ala Arg Gly Ala Gly Gly Ser Ser Leu Gly Ile Asp
    370                 375                 380

Ala Met Met Ala Gly Asp Ala Ile Asn Asn Met Ala Leu Gly Lys Leu
385                 390                 395                 400

Gly Ala Ala
```

This hypersensitive response elicitor polypeptide or protein has a molecular weight of about 39 kDa, has a pI of approximately 4.3, and is heat stable at 100° C. for at least 10 minutes. This hypersensitive response elicitor polypeptide or protein has substantially no cysteine. The hypersensitive response elicitor polypeptide or protein derived from *Erwinia amylovora* is more fully described in Wei, Z.-M., R. J. Laby, C. H. Zumoff, D. W. Bauer, S.-Y. He, A. Collmer, and S. V. Beer, "Harpin, Elicitor of the Hypersensitive Response Produced by the Plant Pathogen *Erwinia amylovora*," *Science* 257:85–88 (1992), which is hereby incorporated by reference. The DNA molecule encoding this polypeptide or protein has a nucleotide sequence corresponding to SEQ. ID. No. 24 as follows:

```
AAGCTTCGGC ATGGCACGTT TGACCGTTGG GTCGGCAGGG TACGTTTGAA TTATTCATAA   60

GAGGAATACG TTATCAGTCT GAATACAAGT GGGCTGGGAG CGTCAACGAT GCAAATTTCT  120

ATCGGCGGTG CCGGCGGAAA TAACGGGTTG CTGGGTACCA GTCCCCAGAA TGCTGGGTTG  180

GGTCGCAATT CTGCACTGGG GCTGGGCGGC GGTAATCAAA ATGATACCGT CAATCAGCTG  240

GCTGGCTTAC TCACCGGCAT GATGATCATG ATCAGCATGA TGGGCGGTGG TGGGCTGATG  300

GGCGGTGGCT TAGGCGGTGG CTTAGGTAAT GGCTTGGGTG GCTCAGGTGG CCTGGGCGAA  360

GGACTGTCGA ACGCGCTGAA CGATATGTTA GGCGGTTCGC TGAACACGCT GGGCTCGAAA  420

GGCGGCAACA ATACCACTTC AACAACAAAT TCCCCGCTGG ACCAGGCGCT GGGTATTAAC  480

TCAACGTCCC AAAACGACGA TTCCACCTCC GGCACAGATT CCACCTCAGA CTCCAGCGAC  540

CCGATGCAGC AGCTGCTGAA GATGTTCAGC GAGATAATGC AAAGCCTGTT TGGTGATGGG  600

CAAGATGGCA CCCAGGGCAG TTCCTCTGGG GGCAAGCAGC CCACCGAAGG CGAGCAGAAC  660

GCCTATAAAA AAGGAGTCAC TGATGCGCTG TCGGGCCTGA TGGGTAATGG TCTGAGCCAG  720

CTCCTTGGCA ACGGGGGACT GGCAGCTCGT CACCCCCGTA ATGCTGGCAC GGGTCTTGAC  780

GGTTCGTCGC TGGGCGGCAA AGGGCTGCAA AACCTGAGCG GGCCGGTGGA CTACCAGCAC  840

TTAGCTAACG CCGTGGGTAC CGGTATCGGT ATGAAAGCGG GCATTCAGGC GCTGAATGAT  900

ATCGGTACGC ACAGGCACAG TTCAACCCGT TCTTTCGTCA ATAAAGGCGA TCGGGCGATG  960

GCGAAGGAAA TCGGTCAGTT CATGGACCAG TATCCTGAGG TGTTTGGCAA GCCGCAGTAC 1020

CAGAAAGGCC CGGGTCAGGA GGTGAAAACC GATGACAAAT CATGGGCAAA AGCACTGAGC 1080

AAGCCAGATG ACCACGGAAT GACACCAGCC AGTATGGAGC AGTTCAACAA AGCCAAGGGC 1140

ATGATCAAAA GGCCCATGCC CGGTGATACC GGCAACGGCA ACCTGCAGGC ACGCGGTGCC 1200

GGTGTTTCTT CGCTGGGTAT TGATGCCATG ATGGCCGGTG ATGCCATTAA CAATATGGCA 1260

CTTGGCAAGC TGGGCGCGGC TTAAGCTT                                     1288
```

The hypersensitive response elicitor polypeptide or protein derived from *Pseudomonas syringae* has an amino acid sequence corresponding to SEQ. ID. No. 25 as follows:

```
Met Gln Ser Leu Ser Leu Asn Ser Ser Ser Leu Gln Thr Pro Ala Met
1           5                   10                  15

Ala Leu Val Leu Val Arg Pro Glu Ala Glu Thr Thr Gly Ser Thr Ser
            20                  25                  30

Ser Lys Ala Leu Gln Glu Val Val Val Lys Leu Ala Gln Glu Leu Met
        35                  40                  45

Arg Asn Gly Gln Leu Asp Asp Ser Ser Pro Leu Gly Lys Leu Leu Ala
    50                  55                  60

Lys Ser Met Ala Ala Asp Gly Lys Ala Gly Gly Gly Ile Glu Asp Val
65                  70                  75                  80

Ile Ala Ala Leu Asp Lys Leu Ile His Gln Lys Leu Gly Asp Asn Phe
                85                  90                  95

Gly Ala Ser Ala Asp Ser Ala Ser Gly Thr Gly Gln Gn Asp Leu Met
                100                 105                 110

Thr Gln Val Leu Asn Gly Leu Ala Lys Ser Met Leu Asp Asp Leu Leu
        115                 120                 125

Thr Lys Gln Asp Gly Gly Thr Ser Phe Ser Glu Asp Asp Met Pro Met
    130                 135                 140

Leu Asn Lys Ile Ala Gln Phe Met Asp Asp Asn Pro Ala Gln Phe Pro
145                 150                 155                 160

Lys Pro Asp Ser Gly Ser Trp Val Asn Gln Len Lys Gln Asp Asn Phe
                165                 170                 175

Leu Asp Gly Asp Gln Thr Ala Ala Phe Arg Ser Ala Len Asp Ile Ile
            180                 185                 190

Gly Gln Gln Leu Gly Asn Gln Gln Ser Asp Ala Gly Ser Leu Ala Gly
        195                 200                 205

Thr Gly Gly Gly Leu Gly Thr Pro Ser Ser Phe Ser Asn Asn Ser Ser
    210                 215                 220

Val Met Gly Asp Pro Leu Ile Asp Ala Asn Thr Gly Pro Gly Asp Ser
225                 230                 235                 240

Gly Asn Thr Arg Gly Gln Ala Gly Gln Leu Ile Gly Gln Leu Ile Asp
                245                 250                 255

Arg Gly Leu Gln Ser Val Leu Ala Gly Gly Gly Leu Gly Thr Pro Val
            260                 265                 270

Asn Thr Pro Gln Thr Gly Thr Ser Ala Asn Gly Gly Gln Ser Ala Gln
        275                 280                 285

Asp Leu Asp Gln Leu Leu Gly Gly Leu Leu Leu Lys Gly Leu Glu Ala
    290                 295                 300

Thr Leu Lys Asp Ala Gly Gln Thr Gly Thr Asp Val Gln Ser Ser Ala
305                 310                 315                 320

Ala Gln Ile Ala Thr Leu Leu Val Ser Thr Leu Leu Gln Gly Thr Arg
                325                 330                 335

Asn Gln Ala Ala Ala
            340
```

This hypersensitive response elicitor polypeptide or protein has a molecular weight of 34–35 kDa. It is rich in glycine (about 13.5%) and lacks cysteine and tyrosine. Further information about the hypersensitive response elicitor derived from *Pseudomonas syringae* is found in He, S. Y., H. C. Huang, and A. Collmer, "*Pseudomonas syringae* pv. *syringae* Harpin$_{Pss}$: a Protein that is Secreted via the Hrp Pathway and Elicits the Hypersensitive Response in Plants," *Cell* 73:1255–1266 (1993), which is hereby incorporated by reference. The DNA molecule encoding the hypersensitive response elicitor from *Pseudomonas syringae* has a nucleotide sequence corresponding to SEQ. ID. No. 26 as follows:

```
ATGCAGAGTC TCAGTCTTAA CAGCAGCTCG CTGCAAACCC CGGCAATGGC CCTTGTCCTG  60
GTACGTCCTG AAGCCGAGAC GACTCGCAGT ACGTCGAGCA AGGCGCTTCA GGAAGTTGTC  120
GTGAAGCTGG CCGAGGAACT GATGCGCAAT GGTCAACTCG ACGACAGCTC GCCATTGGGA  180
AAACTGTTCG CCAACTCGAT GGCCGCAGAT GGCAAGGCGG GCGGCGGTAT TGAGGATGTC  240
ATCCCTGCGC TGGACAAGCT GATCCATCAA AAGCTCGGTC ACAACTTCGG CGCGTCTGCG  300
GACAGCGCCT CGGGTACCGG ACAGCAGGAC CTGATGACTC AGGTGCTCAA TGGCCTCGCC  360
AAGTCGATGC TCGATGATCT TCTGACCAAG CAGGATGGCG GGACAAGCTT CTCCGAAGAC  420
GATATGCCGA TGCTGAACAA GATCGCGCAG TTCATGGATG ACAATCCCGC ACAGTTTCCC  480
AAGCCGGACT CCGCCTCCTC GGTGAACGAA CTCAAGGAAG ACAACTTCCT TGATGGCGAC  540
GAAACGGCTG CGTTCCGTTC GCCACTCGAC ATCATTGGCC AGCAACTGGG TAATCACCAG  600
AGTGACGCTG GCAGTCTGGC AGGGACGGGT GGAGGTCTGG GCACTCCGAG CAGTTTTTCC  660
GGCAATACCC GTGGTGAAGC GGGGCAACTG ATCGGCGAGC TTATCGACCG TGGCCTGCAA  780
TCGGTATTGG CCGGTGGTGG ACTGGGCACA CCCGTAAACA CCCCGCAGAC CGGTACGTCG  840
GCGAATGGCG GACAGTCCGC TCAGGATCTT GATCAGTTGC TGGGCGGCTT GCTGCTCAAG  900
GGCCTGGAGG CAACGCTCAA GGATGCCGGG CAAACAGCCA CCGACGTGCA GTCGAGCGCT  960
GCGCAAATCG CCACCTTGCT GGTCAGTACG CTGCTGCAAG GCACCCGCAA TCAGGCTGCA  1020
GCCTGA                                                             1026
```

The hypersensitive response elicitor polypeptide or protein derived from *Pseudomonas solanacearum* has an amino acid sequence corresponding to SEQ. ID. No. 27 as follows:

```
Met Ser Val Gly Asn Ile Gln Ser Pro Ser Asn Leu Pro Gly Leu Gln
1               5                   10                  15

Asn Leu Asn Leu Asn Thr Asn Thr Asn Ser Gln Gln Ser Gly Gln Ser
            20                  25                  30

Val Gln Asp Leu Ile Lys Gln Val Glu Lys Asp Ile Leu Asn Ile Ile
        35                  40                  45

Ala Ala Leu Val Gln Lys Ala Ala Gln Ser Ala Gly Gly Asn Thr Gly
    50                  55                  60

Asn Thr Gly Asn Ala Pro Ala Lys Asp Gly Asn Ala Asn Ala Gly Ala
65                  70                  75                  80

Asn Asp Pro Ser Lys Asn Asp Pro Ser Lys Ser Gln Ala Pro Gln Ser
                85                  90                  95

Ala Asn Lys Thr Gly Asn Val Asp Asp Ala Asn Asn Gln Asp Pro Met
            100                 105                 110

Gln Ala Leu Met Gln Leu Leu Gln Asp Leu Val Lys Leu Leu Lys Ala
        115                 120                 125

Ala Leu His Met Gln Gln Pro Gly Gly Asn Asp Lys Gly Asn Gly Val
    130                 135                 140

Gly Gly Ala Asn Gly Ala Lys Gly Ala Gly Gly Gln Gly Gly Leu Ala
145                 150                 155                 160

Glu Ala Leu Gln Gln Ile Gln Gln Ile Leu Ala Gln Leu Gly Gly Gly
                165                 170                 175

Gly Ala Gly Ala Gly Gly Ala Gly Gly Gly Val Gly Gly Ala Gly Gly
            180                 185                 190

Ala Asp Gly Gly Ser Gly Ala Gly Gly Ala Gly Gly Ala Asn Gly Ala
        195                 200                 205
```

-continued

```
Asp Gly Gly Asn Gly Val Asn Gly Asn Gln Ala Asn Gly Pro Gln Asn
    210                 215                 220

Ala Gly Asp Val Asn Gly Ala Asn Gly Ala Asp Asp Gly Ser Glu Asp
225                 230                 235                 240

Gln Gly Gly Leu Thr Gly Val Leu Gln Lys Leu Met Lys Ile Leu Asn
                245                 250                 255

Ala Leu Val Gln Met Met Gln Gln Gly Gly Leu Gly Gly Gly Asn Gln
            260                 265                 270

Ala Gln Gly Gly Ser Lys Gly Ala Gly Asn Ala Ser Pro Ala Ser Gly
        275                 280                 285

Ala Asn Pro Gly Ala Asn Gln Pro Gly Ser Ala Asp Asp Gln Ser Ser
    290                 295                 300

Gly Gln Asn Asn Leu Gln Ser Gln Ile Met Asp Val Val Lys Glu Val
305                 310                 315                 320

Val Gln Ile Leu Gln Gln Met Leu Ala Ala Gln Asn Gly Gly Ser Gln
                325                 330                  335

Gln Ser Thr Ser Thr Gln Pro Met
            340
```

It is encoded by a DNA molecule having a nucleotide sequence corresponding SEQ. ID. No. 28 as follows:

```
ATGTCAGTCG GAAACATCCA GAGCCCGTCG AACCTCCCGG GTCTGCAGAA CCTGAACCTC  60

AACACCAACA CCAACAGCCA GCAATCGGGC CAGTCCGTGC AAGACCTGAT CAAGCAGGTC  120

GAGAAGGACA TCCTCAACAT CATCGCAGCC CTCGTGCAGA AGGCCGCACA GTCGGCGGGC  180

GGCAACACCG GTAACACCGG CAACGCGCCG GCGAAGGACG GCAATGCCAA CGCGGGCGCC  240

AACGACCCGA GCAAGAACGA CCCGAGCAAG AGCCAGGCTC CGCAGTCGGC CAACAACACC  300

GGCAACGTCG ACGACGCCAA CAACCAGGAT CCGATGCAAG CGCTGATGCA GCTCCTGGAA  360

GACCTGGTGA AGCTGCTGAA GGCGGCCCTG CACATGCAGC AGCCCGGCGG CAATGACAAG  420

GGCAACGGCG TGGGCGGTGC CAACGGCCCC AAGGGTGCCG GCGGCCAGGG CGGCCTGGCC  480

GAAGCGCTGC AGGAGATCGA GCAGATCCTC GCCCAGCTCG GCGGCGGCGG TGCTGGCGCC  540

GGCGGCGCGG GTGGCGGTGT CGGCGGTCCT CGTGGCGCGG ATGGCGGCTC CGGTGCGGGT  600

GGCGCAGGCG GTGCGAACGG CGCCGACGGC GGCAATGGCG TGAACGGCAA CCAGGCGAAC  660

GGCCCGCAGA ACGCAGGCGA TGTCAACGGT GCCAACGGCG CGGATGACGG CAGCGAAGAC  720

CAGGGCGGCC TCACCGGCGT GCTGCAAAAG CTGATGAAGA TCCTGAACGC GCTGGTGCAG  780

ATGATGCAGC AAGGCGGCCT CGGCGGCGGC AACCAGGCGC AGGGCGGCTC GAAGGGTGCC  840

GGCAACGCCT CCCCGGCTTC CGGCGCGAAC CCGGGCGCGA ACCAGCCCGG TTCGGCGGAT  900

GATCAATCGT CCGGCCAGAA CAATCTGCAA TCCCAGATCA TGGATCTGGT GAAGGAGGTC  960

GTCCAGATCC TGCAGCAGAT GCTGGCGGCG CAGAACGGCG GCAGCCAGCA GTCCACCTCG  1020

ACGCAGCCGA TGTAA                                                   1035
```

Further information regarding the hypersensitive response elicitor polypeptide or protein derived from *Pseudomonas solanacearum* is set forth in Arlat, M., F. Van Gijsegem, J. C. Huet, J. C. Pemollet, and C. A. Boucher, "PopA1, a Protein which Induces a Hypersensitive-like Response in Specific Petunia Genotypes, is Secreted via the Hrp Pathway of *Pseudomonas solanacearum*," *EMBO J.* 13:543–533 (1994), which is hereby incorporated by reference.

The hypersensitive response elicitor polypeptide or protein from *Xanthomonas campestris* pv. glycines has an amino acid sequence corresponding to SEQ. ID. No. 29 as follows:

```
Thr Leu Ile Glu Leu Met Ile Val Val Ala Ile Ile
1               5                   10

Ala Ile Leu Ala Ala Ile Ala Leu Pro Ala Tyr Gln
        15                  20

Asp Tyr
25
```

This sequence is an amino terminal sequence having only 26 residues from the hypersensitive response elicitor polypeptide or protein of *Xanthomonas campestris* pv. glycines. It matches with fimbrial subunit proteins determined in other *Xanthomonas campestris* pathovars.

The hypersensitive response elicitor polypeptide or protein from *Xanthomonas campestris* pv. pelargonii is heat stable, protease sensitive, and has a molecular weight of 20 kDa. It includes an amino acid sequence corresponding to SEQ. ID. No. 30 as follows:

```
Ser Ser Gln Gln Ser Pro Ser Ala Gly Ser Glu Gln
1               5                   10

Gln Leu Asp Gln Leu Leu Ala Met
        15                  20
```

Isolation of *Erwinia carotovora* hypersensitive response elictor protein or polypeptide is described in Cui et al., "The RsmA Mutants of *Erwinia carotovora* subsp. *carotovora* Strain Ecc71 Overexpress hrp $N_{Ecc}$ and Elicit a Hypersensitive Reaction-like Response in Tobacco Leaves," *MPMI,* 9(7):565–73 (1996), which is hereby incorporated by reference. The hypersensitive response elicitor protein or polypeptide of *Erwinia stewartii* is set forth in Ahmad et al., "Harpin is Not Necessary for the Pathogenicity of *Erwinia stewartii* on Maize," *8th Int'l. Cong. Molec. Plant-Microbe Interact.,* Jul. 14–19, 1996 and Ahmad, et al., "Harpin is Not Necessary for the Pathogenicity of *Erwinia stewartii* on Maize," *Ann. Mtg. Am. Phytopath. Soc.,* Jul. 27–31, 1996, which are hereby incorporated by reference.

Hypersensitive response elicitor proteins or polypeptides from *Phytophthora parasitica, Phytophthora cryptogea, Phytophthora cinnamoni, Phytophthora capsici, Phytophthora megasperma,* and *Phytophora citrophthora* are described in Kaman, et al., "Extracellular Protein Elicitors from *Phytophthora:* Most Specificity and Induction of Resistance to Bacterial and Fungal Phytopathogens," *Molec. Plant-Microbe Interact.,* 6(1):15–25 (1993), Ricci et al., "Structure and Activity of Proteins from Pathogenic Fungi *Phytophthora* Eliciting Necrosis and Acquired Resistance in Tobacco," *Eur. J. Biochem.,* 183:555–63 (1989), Ricci et al., "Differential Production of Parasiticein, and Elicitor of Necrosis and Resistance in Tobacco, by Isolates of *Phytophthora parasitica," Plant Path.* 41:298–307 (1992), Baillreul et al, "A New Elicitor of the Hypersensitive Response in Tobacco: A Fungal Glycoprotein Elicits Cell Death, Expression of Defence Genes, Production of Salicylic Acid, and Induction of Systemic Acquired Resistance," *Plant J.,* 8(4): 551–60 (1995), and Bonnet et al., "Acquired Resistance Triggered by Elicitors in Tobacco and Other Plants," *Eur. J. Plant Path.,* 102:181–92 (1996), which are hereby incorporated by reference.

The above elicitors are exemplary. Other elicitors can be identified by growing fungi or bacteria that elicit a hypersensitive response under which genes encoding an elicitor are expressed. Cell-free preparations from culture supernatants can be tested for elicitor activity (i.e. local necrosis) by using them to infiltrate appropriate plant tissues.

Fragments of the above hypersensitive response elicitor polypeptides or proteins as well as fragments of full length elicitors from other pathogens are encompassed by the method of the present invention.

Suitable fragments can be produced by several means. In the first, subclones of the gene encoding a known elicitor protein are produced by conventional molecular genetic manipulation by subcloning gene fragments. The subclones then are expressed in vitro or in vivo in bacterial cells to yield a smaller protein or peptide that can be tested for elicitor activity according to the procedure described below.

As an alternative, fragments of an elicitor protein can be produced by digestion of a full-length elicitor protein with proteolytic enzymes like chymotrypsin or *Staphylococcus* proteinase A, or trypsin. Different proteolytic enzymes are likely to cleave elicitor proteins at different sites based on the amino acid sequence of the elicitor protein. Some of the fragments that result from proteolysis may be active elicitors of resistance.

In another approach, based on knowledge of the primary structure of the protein, fragments of the elicitor protein gene may be synthesized by using the PCR technique together with specific sets of primers chosen to represent particular portions of the protein. These then would be cloned into an appropriate vector for expression of a truncated peptide or protein.

Chemical synthesis can also be used to make suitable fragments. Such a synthesis is carried out using known amino acid sequences for the elicitor being produced. Alternatively, subjecting a full length elicitor to high temperatures and pressures will produce fragments. These fragments can then be separated by conventional procedures (e.g., chromatography, SDS-PAGE).

An example of suitable fragments of an *Erwinia* hypersensitive response elicitor which fragments elicit a hypersensitive response are fragments of the *Erwinia amylovora* hypersensitive response elicitor. Suitable fragments include a C-terminal fragment of the amino acid sequence of SEQ. ID. No. 23, an N-terminal fragment of the amino acid sequence of SEQ. ID. No. 23, or an internal fragment of the amino acid sequence of SEQ. ID. No. 23. The C-terminal fragment of the amino acid sequence of SEQ. ID. No. 23 can span amino acids 105 and 403 of SEQ. ID. No. 23. The N-terminal fragment of the amino acid sequence of SEQ. ID. No. 23 can span the following amino acids of SEQ. ID. No. 23: 1 and 98, 1 and 104, 1 and 122, 1 and 168, 1 and 218, 1 and 266, 1 and 342, 1 and 321, and 1 and 372. The internal fragment of the amino acid sequence of SEQ. ID. No. 23 can span the following amino acids of SEQ. ID. No. 23: 76 and 209, 105 and 209, 99 and 209, 137 and 204, 137 and 200, 109 and 204, 109 and 200, 137 and 180, and 105 and 180. Other suitable fragments can be identified in accordance with the present invention.

Variants may be made by, for example, the deletion or addition of amino acids that have minimal influence on the properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

The fragment of the present invention is preferably produced in purified form (preferably at least about 60%, more preferably 80%, pure) by conventional techniques. Typically, the fragment of the present invention is produced but not secreted into the growth medium of recombinant host cells. Alternatively, the protein or polypeptide of the present invention is secreted into growth medium. In the case of unsecreted protein, to isolate the protein fragment, the host cell (e.g., *E. coli*) carrying a recombinant plasmid is propagated, lysed by sonication, heat, or chemical treatment, and the homogenate is centrifuged to remove bacterial debris. The supernatant is then subjected to heat treatment and the fragment is separated by centrifugation. The supernatant fraction containing the fragment is subjected to gel filtration in an appropriately sized dextran or polyacrylamide column to separate the fragment. If necessary, the protein fraction may be further purified by ion exchange or HPLC.

The DNA molecule encoding the fragment of the hypersensitive response elicitor polypeptide or protein can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccina virus. Recombinant viruses can be generated by transection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK+/−or KS+/−(see "Stratagene Cloning Systems" Catalog (1993) from Stratagene, La Jolla, Calif, which is hereby incorporated by reference), pQE, pIH821, pGEX, pET series (see F. W. Studier et. al., "Use of T7 RNA Polymerase to Direct Expression of Cloned Genes," *Gene Expression Technology* vol. 185 (1990), which is hereby incorporated by reference), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual,* Cold Springs Laboratory, Cold Springs Harbor, N.Y. (1989), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promotor which is a DNA sequence that directs the binding of RNA polymerase and thereby promotes mRNA synthesis. The DNA sequences of eucaryotic promoters differ from those of procaryotic promoters. Furthermore, eucaryotic promoters and accompanying genetic signals may not be recognized in or may not function in a procaryotic system, and, further, procaryotic promoters are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosome binding site called the Shine-Dalgamo ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology,* 68:473 (1979), which is hereby incorporated by reference.

Promotors vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promotors may be used. For instance, when cloning in *E. coli*, its bacteriophages, or plasmids, promoters such as the T7 phage promoter, lac promotor, trp promotor, recA promotor, ribosomal RNA promotor, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promotor or other *E. coli* promoters produced by recombinant DNA or other synthetic DNA techniques may be used to provide for transcription of the inserted gene.

Bacterial host cell strains and expression vectors may be chosen which inhibit the action of the promotor unless specifically induced. In certain operations, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcrip tion and/or translation initiation signals. For instance, efficient translation in *E. coli* requires an SD sequence about 7–9 bases 5' to the initiation codon ("ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecule encoding the fragment of a hypersensitive response elicitor polypeptide or protein has been cloned into an expression system, it is ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

The present invention further relates to methods of imparting disease resistance to plants, enhancing plant growth, and/or effecting insect control for plants. These methods involve applying the fragment of a hypersensitive response elicitor polypeptide or protein, which fragment itself elicits a hypersensitive response, in a non-infectious form to all or part of a plant or a plant seed under conditions effective for the fragment to impart disease resistance, enhance growth, and/or control insects. Alternatively, these fragments of a hypersensitive response elicitor protein or polypeptide can be applied to plants such that seeds recovered from such plants themselves are able to impart disease resistance in plants, to enhance plant growth, and/or to effect insect control.

As an alternative to applying a fragment of a hypersensitive response elicitor polypeptide or protein to plants or plant seeds in order to impart disease resistance in plants, to effect plant growth, and/or to control insects on the plants or plants grown from the seeds, transgenic plants or plant seeds can be utilized. When utilizing transgenic plants, this involves providing a transgenic plant transformed with a DNA molecule encoding a fragment of a hypersensitive response elicitor polypeptide or protein, which fragment elicits a hypersensitive response, and growing the plant under conditions effective to permit that DNA molecule to impart disease resistance to plants, to enhance plant growth, and/or to control insects. Alternatively, a transgenic plant seed transformed with a DNA molecule encoding a fragment of a hypersensitive response elicitor polypeptide or protein which fragment elicits a hypersensitive response can be provided and planted in soil. A plant is then propagated from the planted seed under conditions effective to permit that DNA molecule to impart disease resistance to plants, to enhance plant growth, and/or to control insects.

The embodiment of the present invention where the hypersensitive response elicitor polypeptide or protein is applied to the plant or plant seed can be carried out in a number of ways, including: 1) application of an isolated fragment or 2) application of bacteria which do not cause disease and are transformed with a genes encoding the fragment. In the latter embodiment, the fragment can be applied to plants or plant seeds by applying bacteria containing the DNA molecule encoding the fragment of the hypersensitive response elicitor polypeptide or protein which fragment elicits a hypersensitive response. Such bacteria must be capable of secreting or exporting the fragment so that the fragment can contact plant or plant seeds cells. In these embodiments, the fragment is produced by the bacteria in planta or on seeds or just prior to introduction of the bacteria to the plants or plant seeds.

The methods of the present invention can be utilized to treat a wide variety of plants or their seeds to impart disease resistance, enhance growth, and/or control insects. Suitable plants include dicots and monocots. More particularly, useful crop plants can include: alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, and sugarcane. Examples of suitable ornamental plants are: *Arabidopsis thaliana, Saintpaulia,* petunia, pelargonium, poinsettia, chrysanthemum, carnation, and zinnia.

With regard to the use of the fragments of the hypersensitive response elicitor protein or polypeptide of the present invention in imparting disease resistance, absolute immunity against infection may not be conferred, but the severity of the disease is reduced and symptom development is delayed. Lesion number, lesion size, and extent of sporulation of fungal pathogens are all decreased. This method of imparting disease resistance has the potential for treating previously untreatable diseases, treating diseases systemically which might not be treated separately due to cost, and avoiding the use of infectious agents or environmentally harmful materials.

The method of imparting pathogen resistance to plants in accordance with the present invention is useful in imparting resistance to a wide variety of pathogens including viruses, bacteria, and fungi. Resistance, inter alia, to the following viruses can be achieved by the method of the present invention: Tobacco mosaic virus and Tomato mosaic virus. Resistance, inter alia, to the following bacteria can also be imparted to plants in accordance with present invention: *Pseudomonas solancearum, Pseudomonas syringae* pv. *tabaci,* and *Xanthamonas campestris* pv. *pelargonii.* Plants can be made resistant, inter alia, to the following fungi by use of the method of the present invention: *Fusarium oxysporum* and *Phytophthora infestans.*

With regard to the use of the fragments of the hypersensitive response elicitor protein or polypeptide of the present invention to enhance plant growth, various forms of plant growth enhancement or promotion can be achieved. This can occur as early as when plant growth begins from seeds or later in the life of a plant. For example, plant growth according to the present invention encompasses greater yield, increased quantity of seeds produced, increased percentage of seeds germinated, increased plant size, greater biomass, more and bigger fruit, earlier fruit coloration, and earlier fruit and plant maturation. As a result, the present invention provides significant economic benefit to growers. For example, early germination and early maturation permit crops to be grown in areas where short growing seasons would otherwise preclude their growth in that locale. Increased percentage of seed germination results in improved crop stands and more efficient seed use. Greater yield, increased size, and enhanced biomass production allow greater revenue generation from a given plot of land.

Another aspect of the present invention is directed to effecting any form of insect control for plants. For example, insect control according to the present invention encompasses preventing insects from contacting plants to which the hypersensitive response elicitor has been applied, preventing direct insect damage to plants by feeding injury, causing insects to depart from such plants, killing insects proximate to such plants, interfering with insect larval feeding on such plants, preventing insects from colonizing host plants, preventing colonizing insects from releasing phytotoxins, etc. The present invention also prevents subsequent disease damage to plants resulting from insect infection. The present invention is effective against a wide variety of insects. European corn borer is a major pest of corn (dent and sweet corn) but also feeds on over 200 plant species including green, wax, and lima beans and edible soybeans, peppers, potato, and tomato plus many weed species. Additional insect larval feeding pests which damage a wide variety of vegetable crops include the following: beet armyworm, cabbage looper, corn ear worm, fall armyworm, diamondback moth, cabbage root maggot, onion maggot, seed corn maggot, pickleworm (melonworm), pepper maggot, tomato pinworm, and maggots. Collectively, this group of insect pests represents the most economically important group of pests for vegetable production worldwide.

The method of the present invention involving application of the fragment of a hypersensitive response elicitor polypeptide or protein, which fragment elicits a hypersensitive response, can be carried out through a variety of procedures when all or part of the plant is treated, including leaves, stems, roots, etc. This may (but need not) involve infiltration of the hypersensitive response elicitor polypeptide or protein into the plant. Suitable application methods include high or low pressure spraying, injection, and leaf abrasion proximate to when elicitor application takes place. When treating plant seeds or propagules (e.g., cuttings), in accordance with the application embodiment of the present invention, the fragment of the hypersensitive response elicitor protein or polypeptide, in accordance with present invention, can be applied by low or high pressure spraying, coating, immersion, or injection. Other suitable application procedures can be envisioned by those skilled in the art provided they are able to effect contact of the fragment with cells of the plant or plant seed. Once treated with the fragment of the hypersensitive response elicitor of the present invention, the seeds can be planted in natural or artificial soil and cultivated using conventional procedures to produce plants. After plants have been propagated from seeds treated in accordance with the present invention, the plants may be treated with one or more applications of the fragment of the hypersensitive response elicitor protein or polypeptide or whole elicitors to impart disease resistance to plants, to enhance plant growth, and/or to control insects on the plants.

The fragment of the hypersensitive response elicitor polypeptide or protein, in accordance with the present invention, can be applied to plants or plant seeds alone or in a mixture with other materials. Alternatively, the fragment can be applied separately to plants with other materials being applied at different times.

A composition suitable for treating plants or plant seeds in accordance with the application embodiment of the present invention contains a fragment of a hypersensitive response elicitor polypeptide or protein which fragment elicits a hypersensitive response in a carrier. Suitable carriers include water, aqueous solutions, slurries, or dry powders. In this embodiment, the composition contains greater than 500 nM of the fragment.

Although not required, this composition may contain additional additives including fertilizer, insecticide, fungicide, nematacide, and mixtures thereof. Suitable fertilizers include $(NH_4)_2NO_3$. An example of a suitable insecticide is Malathion. Useful fungicides include Captan.

Other suitable additives include buffering agents, wetting agents, coating agents, and abrading agents. These materials can be used to facilitate the process of the present invention. In addition, the hypersensitive response eliciting fragment can be applied to plant seeds with other conventional seed formulation and treatment materials, including clays and polysaccharides.

In the alternative embodiment of the present invention involving the use of transgenic plants and transgenic seeds, a hypersensitive response eliciting fragment need not be applied topically to the plants or seeds. Instead, transgenic plants transformed with a DNA molecule encoding such a fragment are produced according to procedures well known in the art.

The vector described above can be microinjected directly into plant cells by use of micropipettes to transfer mechanically the recombinant DNA. Crossway, *Mol. Gen. Genetics,* 202:179–85 (1985), which is hereby incorporated by reference. The genetic material may also be transferred into the plant cell using polyethylene glycol. Krens, et al., *Nature,* 296:72–74 (1982), which is hereby incorporated by reference.

Another approach to transforming plant cells with a gene which imparts resistance to pathogens is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford et al., which are hereby incorporated by reference. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells.

Yet another method of introduction is fusion of protoplasts with other entities, either minicells, cells, lysosomes, or other fusible lipid-surfaced bodies. Fraley, et al., *Proc. Natl. Acad. Sci. USA,* 79:1859–63 (1982), which is hereby incorporated by reference.

The DNA molecule may also be introduced into the plant cells by electroporation. Fromm et al., *Proc. Natl. Acad. Sci. USA,* 82:5824 (1985), which is hereby incorporated by reference. In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate.

Another method of introducing the DNA molecule into plant cells is to infect a plant cell with *Agrobacterium tumefaciens* or *A. rhizogenes* previously transformed with the gene. Under appropriate conditions known in the art, the transformed plant cells are grown to form shoots or roots, and develop further into plants. Generally, this procedure involves inoculating the plant tissue with a suspension of bacteria and incubating the tissue for 48 to 72 hours on regeneration medium without antibiotics at 25–28° C.

*Agrobacterium* is a representative genus of the gram-negative family Rhizobiaceae. Its species are responsible for crown gall (*A. tumefaciens*) and hairy root disease (*A.

*rhizogenes*). The plant cells in crown gall tumors and hairy roots are induced to produce amino acid derivatives known as opines, which are catabolized only by the bacteria. The bacterial genes responsible for expression of opines are a convenient source of control elements for chimeric expression cassettes. In addition, assaying for the presence of opines can be used to identify transformed tissue.

Heterologous genetic sequences can be introduced into appropriate plant cells, by means of the Ti plasmid of *A. tumefaciens* or the R1 plasmid of *A. rhizogenes*. The Ti or R1 plasmid is transmitted to plant cells on infection by *Agrobacterium* and is stably integrated into the plant genome. J. Schell, *Science,* 237:1176–83 (1987), which is hereby incorporated by reference.

After transformation, the transformed plant cells must be regenerated.

Plant regeneration from cultured protoplasts is described in Evans et al., *Handbook of Plant Cell Cultures, Vol.* 1: (MacMillan Publishing Co., New York, 1983); and Vasil I. R. (ed.), *Cell Culture and Somatic Cell Genetics of Plants,* Acad. Press, Orlando, Vol. 1, 1984, and Vol. III (1986), which are hereby incorporated by reference.

It is known that practically all plants can be regenerated from cultured cells or tissues, including but not limited to, all major species of sugarcane, sugar beets, cotton, fruit trees, and legumes.

Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

After the expression cassette is stably incorporated in transgenic plants, it can be transferred to other plants by sexual crossing. Any of a number of standard breeding techniques can be used, depending upon the species to be crossed.

Once transgenic plants of this type are produced, the plants themselves can be cultivated in accordance with conventional procedure with the presence of the gene encoding the hypersensitive response eliciting fragment resulting in disease resistance, enhanced plant growth, and/or control of insects on the plant. Alternatively, transgenic seeds or propagules (e.g., cuttings) are recovered from the transgenic plants. The seeds can then be planted in the soil and cultivated using conventional procedures to produce transgenic plants. The transgenic plants are propagated from the planted transgenic seeds under conditions effective to impart disease resistance to plants, to enhance plant growth, and/or to control insects. While not wishing to be bound by theory, such disease resistance, growth enhancement, and/or insect control may be RNA mediated or may result from expression of the polypeptide or protein fragment.

When transgenic plants and plant seeds are used in accordance with the present invention, they additionally can be treated with the same materials as are used to treat the plants and seeds to which a hypersensitive response eliciting fragment is applied. These other materials, including hypersensitive response eliciting fragments, can be applied to the transgenic plants and plant seeds by the above-noted procedures, including high or low pressure spraying, injection, coating, and immersion. Similarly, after plants have been propagated from the transgenic plant seeds, the plants may be treated with one or more applications of the hypersensitive response eliciting fragment to impart disease resistance, enhance growth, and/or control insects. Such plants may also be treated with conventional plant treatment agents (e.g., insecticides, fertilizers, etc.).

EXAMPLES

Example 1

Strains and Plasmids used

The strains and plasmids used are set forth in Table 1 below

TABLE 1

| Plasmid name | *E. amylovora* source strain | Brief Description, Relevant Phenotype, Reference | Harpin, fragment (or NA) |
|---|---|---|---|
| pBCKS | — | $Cm^r$ derivative of pBluescript KS. Stratagene, La Jolla, CA | |
| pBCSK | — | $Cm^r$ derivative of pBluescript SK. Stratagene, La Jolla, CA | |
| pBSKS | — | pBluescript KS; $Ap^r$. Stratagene, La Jolla, CA | |
| pBSSK II | — | pBluescript II SK; $Ap^r$. Stratagene, La Jolla, CA | |
| pBW7 | — | Mob + $Tc^r$ helper plasmid. (Rella, et al., "Transposon Insertion Mutagenesis of *Pseudomonas aeruginosa* With a Tn5 Derivative: Application to Physical Mapping of the arc Gene Cluster," Gene 33:293–303 (1985), which is hereby incorporated by reference) | NA |
| pCPP51 | — | Broad host range derivative of pBSSK II containing ori from pRO1614. | NA |
| PCPP430 | 321 | Functional hrp gene cluster of *E. amylovora* Ea321 cloned into pCPP9. Beer, S.V., et al., "The hrp Gene Cluster of Erwinia Amylovora," In Hennecke, H., and D.P.S. Verma, (eds.), Advances in Molecular Genetics of Plant-Microbe Interactions Kluwer Academic Publishers, Dordrecht, Netherlands, 53–60 (1991), which is hereby incorporated by reference. | |

TABLE 1-continued

| | | | |
|---|---|---|---|
| pCPP460 | 246 | Functional hrp gene cluster of *E. amylovora* Ea246 cloned into pCPP9. | |
| pCPP1104 | 321 | 1.2 kb PstI fragment of pCPP1084 in pBCKS | Ea C31 |
| pCPP1105 | 321 | 1.1 kb SmaI fragment of pCPP1084 in pBCSK | Ea C82 |
| pCPp1107 | 321 | 1.3 kb HindIII fragment of pCPP1084 in pBCSK | Ea wt |
| pCPp1108 | 321 | 1.2 kb HincII-HindIII of pCPP1084 in pBCSK | Ea N11 |
| pCPP1109 | 321 | pCPP1107 with internal AvaII fragment deleted | Ea 1175 |
| pCPP1110 | 321 | As pCPP1108, but cloned into pBCKS | Ea N9 |
| pCPP1111 | 321 | 367 bp TaqI fragment of pCPP1107 in pBCSK | Ea C305 |
| pCPP1113 | 246 | As pCPP1109, but 425 bp AvaII fragment of pCPP1098 deleted | Ear 1175 |
| pCPP1119 | 246 | Site specific mutation in pCPP1098; stop codon inserted at L36 | Ear C368 |
| pCPP1120 | 246 | Site specific mutation in pCPP1098; stop codon inserted at T123 | Ear C281 |
| pCPP1121 | 321 | 702 bp KpnI fragment internal to hrpN deleted | Ea C375 |
| pCPP1127 | 246 | 3.1 kb BamH1 fragment of pCPP1098 in pSU21 | Ear wt |
| pCPP1128 | 246 | Tn10 minikan in pCPP1127 | Ear undef |
| pCPP1136 | 246 | 4.4 kb EcoRI fragment of pCPP1120, religated | EAR N122 |
| pCPP1146 | 246 | 4.2 kb EcoRI fragment of pCPP11119, religated | Ear N35 |
| pCPP1147 | 321 | 1.2 kb BamH1 fragment of pCPP1084, PCR amplified, cloned into pSU23 | Ea wt |
| pCPP1148 | 246 | As pCPp 1147, but from pCPP1098 | Ear wt |
| pCPP1150 | 246 | As pCPp1148, but in pCPP51 vector | Ear wt |
| pCPP1163 | 246 | 3.1 kb BamH1 fragment of pCPP1098 in pCPP51 | Ear wt |
| pCPP1164 | 321 | 1.3 kb HindIII of pCPp1084 in pCPP51 | Ea wt |
| pCPP1165 | | Derivative of pCPP5 1 w/KpnI, SacII sites removed | NA |
| pCPP1167 | 321 | 1.3 kb HindII fragment of pCPp1107 in pCPP1165 | Ea wt |
| pCPP1169 | 246 | As pCPP 1167, but 3.1 kB BamHI insert from pCPp1098 | Ear wt |
| pCPP1170 | 246 | PCPP1098; ΣX-Sp ligated into EcoRV site | Ear C128Σ |
| pCPP1171 | 246 | KpnI fragment internal to hrpN deleted; shifted reading frame | Ea C375 |
| pCPPL172 | 321 | Derivative of pCPP1167 with in-frame deletion of KpnI fragment internal to hrpN | Ea 1235 |
| pCPP1173 | 246 | AspCPP1172, but from pCPP1169 | Ear 1235 |
| pCPP217 | 321 | PCPP1084 with 2 StyI fragments deleted, blunted, and religated | Ea C185 |
| pCPP1252 | 321 | PCPP1105 with Σ-Sp ligated at SmaI site | Ea C82Σ |
| pGP1-2 | | P15a ori.T7 RNA polymerase-encoding plasmid; for protein expression (labor, S., et al., "A Bacteriophage T7 DNA Polymerase/Promoter System for Controlled Exclusive Expression of Specific Genes," Proc. Natl. Acad. Sci. USA 82:1074–1078 (1985), which is hereby incorporated by reference). | N/A |
| pHP45Σ Ω | | $Ap^r$; $Sp^r$; source off Ω-Sp fragment; (Fellay, R., et al., "Interposon Mutagenesis of Soil and Water Bacteria a Family of DNA Fragments Designed for in vitro Insertional Mutagenesis of Gram-Negative Bacteria," Gene 52:147–154 (1987), which is hereby incorporated by reference). | N/A |
| pSU21 | | P15a ori $Km^t$ (Bartolomé, B.Y., et al., "Construction and properties of a Family of pACYC184-Derived Cloning Vectors Compatible With pBR322 and its Derivatives," Gene 102:75–78 (1991) , which is hereby incorporated by reference). | N/A |
| PSU23 | | P15a ori $Km^t$ (Bartolomé, B.Y., et al., "Construction and properties of a Family of pACYC184-Derived Cloning Vectors Compatible With pBR322 and its Derivatives," Gene 102:75–78 (1991) , which is hereby incorporated by reference). | N/A |

| Strains used | |
|---|---|
| *E. amylovora* | Ea273Nx; Nalidixic acid resistant ($Nx^r$) derivative of Ea273. CUCPB 2348 |
| *E. amylovora* | Rifampin resistant derivative of Ea32. CUCPB 2545 |
| *E. coli* | GM272; dam-, dcm-. CUCPB 3047; (Blumenthal, R.M., Ct al., "*E. coli* Can Restrict Methylated DNA and May Skew Genomic Libraries," Trends in Biotech. 4:302–305 (1986), which is hereby incorporated by reference) |
| *E. coli* | BL21(DE3); CUCPB 4277; (Studier, F.W., and B.A. Moffatt, "Use of Bacteriophage T7 RNA Polymerase to Direct Selective High-level Expression of Cloned Genes," J. Mol. Biol., 189:113–130(1986), which is hereby incorporated by reference) |
| *E. coli* | DH5α; ($NX^r$). CUCPB 2475; Stratagene, La Jolla, CA. |

Example 2

Molecular Biology Techniques

Several approaches were employed to obtain truncated or otherwise altered versions of both *E. amylovora* harpins. These techniques included: (i) subcloning of restriction fragments containing portions of the gene encoding the hypersensitive response elicitor protein or polypeptide from *Erwinia amylovora* (i.e. hrpN) into expression vectors, by standard techniques (Sambrook, et al., *Molecular Cloning: a Laboratory Manual,* 2nd ed. ed. Cold Spring Harbor, Laboratory," Cold Spring Harbor, N.Y. (1989), which is hereby incorporated by reference); (ii) insertion of an Ω-fragment (Fellay, et al., "Interposon Mutagenesis of Soil and Water Bacteria a Family of DNA Fragments Designed for in vitro Insertional Mutagenesis of Gram-Negative Bacteria," *Gene* 52:147–154 (1987), which is hereby incorporated by reference) into hrpN; (iii) site-specific mutagenesis approaches (Innis, et al., *PCR Protocols. A Guide to Methods and Applications,* Academic Press San Diego, Calif. (1990); Kunkel, et al., "Rapid and Efficient Site-Specific Mutagenesis Without Phenotypic Selection," *Proc. Nat. Acad. Sci.* USA 82:488–492 (1985), which are hereby incorporated by reference); and (iv) creation of nested deletions (Erase-a-Base™ kit; Promega, Madison, Wis.). C-terminal deletion analysis of the hypersensitive response elicitor protein or polypeptide from *Erwinia amylovora* (i.e. $harpin_{Ea}$) in pCPP1084 could not be performed because of the location of restriction enzyme cleavage sites in pCPP 1084. For N-terminal deletions, pCPP 1084 DNA was prepared using a Qiagen midiprep column (Qiagen, Chatsworth, Calif.) and digested with sst I followed by EcoRI. Subsequently, the digested DNA was subjected to exonuclease III digestion, ligation, and transformation into *E. coli* BL21(DE3). Deletion sizes were estimated by agarose gel electrophoresis. Harpin fragments were named with respect to the portion of harpin deleted (e.g., $harpin_{Ea}$ C82 lacks the C-terminal 82 amino acid residues of full-length $harpin_{Ea}$).

Example 3

Protein Expression

For expression from T7 promoters, T7 RNA polymerase-dependent systems were used. These systems utilized either strain *E. coli* BL21(DE3) (Studier, et al., "Use of Bacteriophage T7 RNA Polymerase to Direct Selective High-Level Expression of Cloned Gene," *J. Mol. Biol.* 189: 113–130 (1986), which is hereby incorporated by reference), or plasmid pGP1-2 (Tabor, et al., "A Bacteriophage T7 DNA Polymerase/Promoter System for Controlled Exclusive Expression of Specific Genes," *Proc. Natl. Acad. Sci.,* USA 82:1074–1078 (1985), which is hereby incorporated by reference) in *E. coli* DH5α. Expression of hrpN from the T7 promoter was induced by addition of IPTG to a final concentration of 0.4 mM. For expression in *E. amylovora* Ea321 (i.e. $harpin_{Ea}$) or Ea273, pGP1-2 was introduced by transformation with a 42° C. heat shock for 10 minutes, or by electroporation (Biorad Gene Pulser™). Hypersensitive response (i.e. HR)-eliciting activity was screened in tobacco cv. Xanthi leaves by in planta lysis (He, et al., "*Pseudomonas syringae* pv. *syringae* $harpin_{Pss}$: a Protein That is Secreted via the Hrp Pathway and Elicits the Hypersensitive Response in Plants," *Cell* 73:1255–1266 (1993), which is hereby incorporated by reference) or by preparation of boiled and unboiled "CFEPs" (Wei, et al., "Harpin, Elicitor of the Hypersensitive Response Produced by the Plant Pathogen *Erwinia amylovora,*" *Science* 257:85–88 (1992), which is hereby incorporated by reference).

Example 4

In vitro Proteolysis of Harpin

In vitro proteolysis of $harpin_{Ea}$ with *Staphylococcus* V8 proteinase (also termed endoproteinase Glu-C), trypsin, pepsin, and papain was performed as recommended (Scopes, et al., *Protein Purification: Principles and Practice,* 2nd ed. Springer-Verlag. New York (1987), which is hereby incorporated by reference), for 2–16 hrs. at 20–37°. Endoproteinase Glu-C digestion was performed either in 50 mM ammonium bicarbonate, pH 7.8 (in which cleavage occurs only after glutamic acid), or in 50 mM potassium phosphate, pH 7.8 (in which cleavage after both glutamic acid and aspartic acid occurs).

Example 5

Plant-derived Proteinases

Intercellular fluids (IF) were obtained from tobacco, tomato, apple, raspberry, and cotoneaster, as described (Hammond-Kosack, et al., "Preparation and Analysis of Intercellular Fluid," p. 15–21. In S. J. Gurr, M. J. McPherson, and D. J. Bowles (ed.), *Molecular Plant Pathology A Practical Approach,* 2nd ed., The Practical Approach Series, IRL Publishers, Oxford (1992), which is hereby incorporated by reference), by vacuum infiltration of intercellular spaces with high-purity water. Proteolytic digestion of PAGE-purified $harpin_{Ea}$ was performed for 2–16 hrs. at 20–37° C., pH, by mixing equal volumes of IF with $harpin_{Ea}$. A total leaf extract was obtained by grinding tobacco leaf panels with mortar and pestle in 5 mM potassium phosphate. The extract was centrifuged and filtered, and the clarified ground leaf extract used identically as was the IF. Proteinase inhibitors were employed as follows: Pepstatin A (final concentration 1 μM), E-64 (1 μM), Aprotinin (2 μg/ml), o-phenanthroline (1 mM), and p-mercuribenzoate (PCMB) (Sigma, St. Louis, Mo.).

Example 6

Peptide Purification

Peptide fragments of harpin obtained following digestion with tobacco IF were fractionated by reverse-phase HPLC on a Vydac C 18 column using a 2–60% acetonitrile gradient in 0.1% trifluoroacetic acid. Fractions were lyophilized, resuspended in 5 mM potassium phosphate and infiltrated into tobacco leaf panels. The fraction with greatest HR-eliciting activity was refractionated as above with a 35–70% acetonitrile gradient, and the purity of each fraction was assayed via gas chromatography-mass spectroscopy (GC-MS) and by N-terminal protein sequencing at the Cornell Biotechnology Program Core Facility.

Example 7

Proteinase Activity-stained Gels

Proteinase activity of IF was assayed in activity-stained polyacrylamide gels (Laemmli, "Cleavage of Structural Proteins During the Assembly of the Head of Bacteriophage T4," *Nature* 227:680–685 (1970), which is hereby incorporated by reference) copolymerized with 0.1% gelatin (Heussen, et al., "Electrophoretic Analysis of Plasminogen Activators in Polyacrylamide Gels Containing Sodium Dodecyl Sulfate and Copolymerized Substrates," *Anal. Biochem.* 102:196–202 (1980), which is hereby incorporated by reference). After electrophoresis, each gel was rinsed extensively to remove SDS and allow refolding of proteinases in the gel. Following additional incubation to allow proteolysis to occur, the gels were stained with 0.1% Amido Black in 30% methanol/10% acetic acid. Each gel stained darkly (due to the presence of copolymerized gelatin) except where proteinases had digested the gelatin, resulting in colorless bands representing the sites of proteinase activity.

Example 8

Truncated Harpins Retain HR-eliciting Activity

The stability and the HR-eliciting activity of proteins encoded by various DNA constructs is shown in FIG. 1. Many DNA constructs encoding portions of harpin$_{Ea}$ or harpin$_{Ear}$ did not yield detectable protein products following induction of expression in the T7 promoter-polymerase system (Tabor, et al., "A Bacteriophage T7 DNA Polymerase/Promoter System for Controlled Exclusive Expression of Specific Genes," *Proc. Natl. Acad. Sci.* USA 82:1074–1078 (1985), which is hereby incorporated by reference) and analysis of cell extracts by PAGE, possibly due to instability of the encoded proteins. No DNA constructs (e.g., those obtained via Erase-a-Base™ protocol) yielded detectable protein products displaying N-terminal deletions relative to the full-length protein. No stable but inactive proteins were identified. Several constructs encoding proteins truncated at their C-terminus and often including additional vector-encoded amino acids yielded detectable products (e.g. harpin$_{Ea}$ C82). In contrast, a construct encoding the same 321 N-terminal amino acid residues of harpin$_{Ea}$, but yielding a protein truncated by the presence of an Ω-fragment (harpin$_{Ea}$ C82 Ω) was unstable (i.e. no product was detected). A construct encoding a harpin$_{Ea}$ fragment with a large internal deletion (harpin$_{Ea}$ I175) was also successfully used to express protein. These various truncated proteins were tested for HR-eliciting activity. A 98 residue N-terminal harpin$_{Ea}$ fragment (harpin$_{Ea}$ C305) was the smallest bacterially-produced peptide that displayed HR-eliciting activity.

Example 9

Secretion of Harpin$_{Ea}$ with an Altered C-terminus

Figure 2:
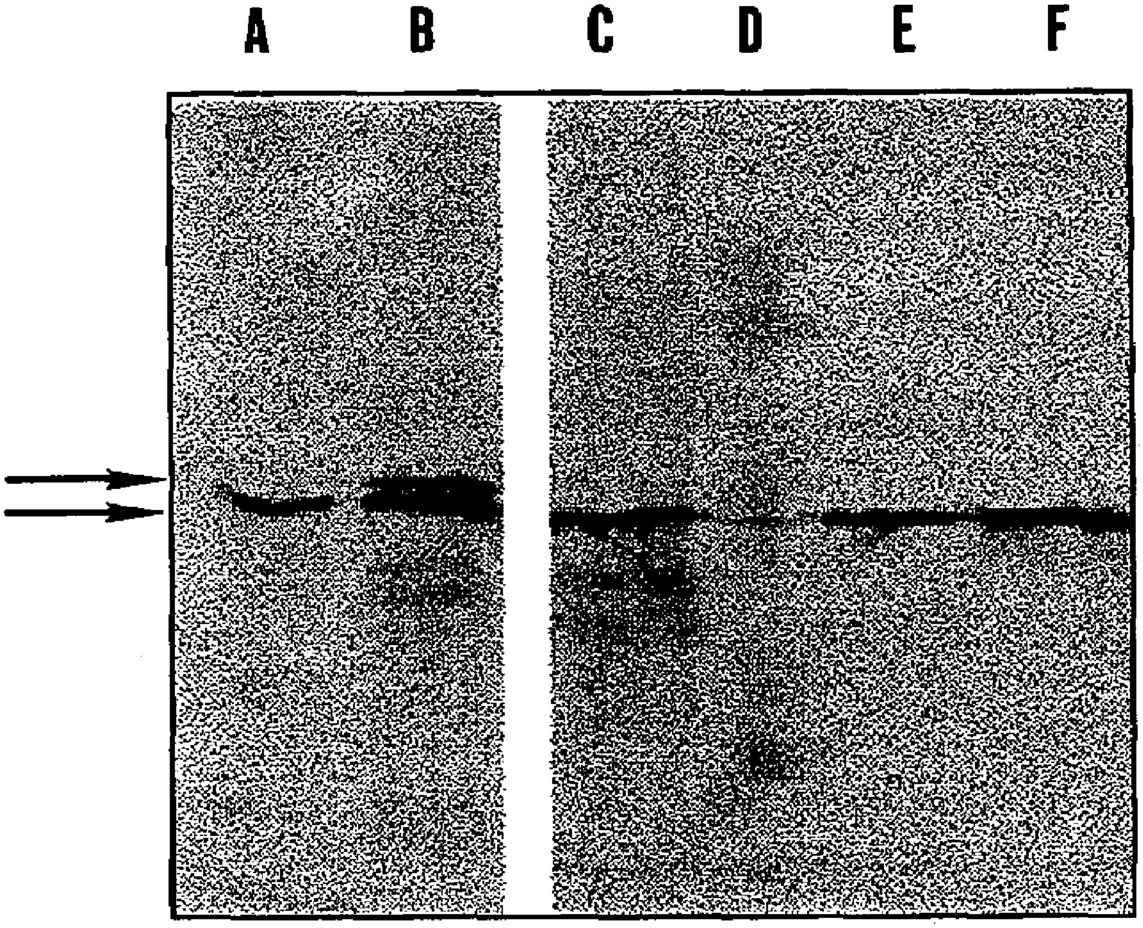
FIG. 2 is a Western blot illustrating specific secretion of harpin$_{Ea}$, but not harpin$_{Ea}$C31. Lane A, Ea273(pGP1-2) CFEP; lane B, Ea273(pGP1-2)(pCPP1104) CFEP; lane C, *E. coli* DH5α (pCPP1107) CFEP harpin size standard; lane D, BioRad low range molecular weight markers; lane E, Ea273 (pGP1-2) supernatant; lane F, Ea273(pGP1 2)(pCPP1104) supernatant. The blot was probed with an anti-harpin$_{Ea}$ polyclonal antibody.

The effect of alteration at the harpin C-terminus on its secretion was examined. Harpin C31 contains the N-terminal 372 amino acids of harpin, but lacks the C-terminal 31 residues, which are replaced by 47 residues encoded by the vector, resulting in a protein slightly larger than the wild type harpin$_{Ea}$. The C31 protein retains HR-eliciting activity and is stable and easily expressed and detected by western analysis or PAGE but it is no longer secreted into the culture supernatant as is the wild type protein (FIG. 2). The presence of harpin$_{Ea}$ C31 does not interfere with secretion of the wild type harpin, which is found in both the CFEP and the culture supernatant. However, harpin$_{Ea}$ C31 is found only in the CFEP.

Example 10

Effect of Proteolysis on Harpin$_{Ea}$'s HR Eliciting Activity

Figure 3:
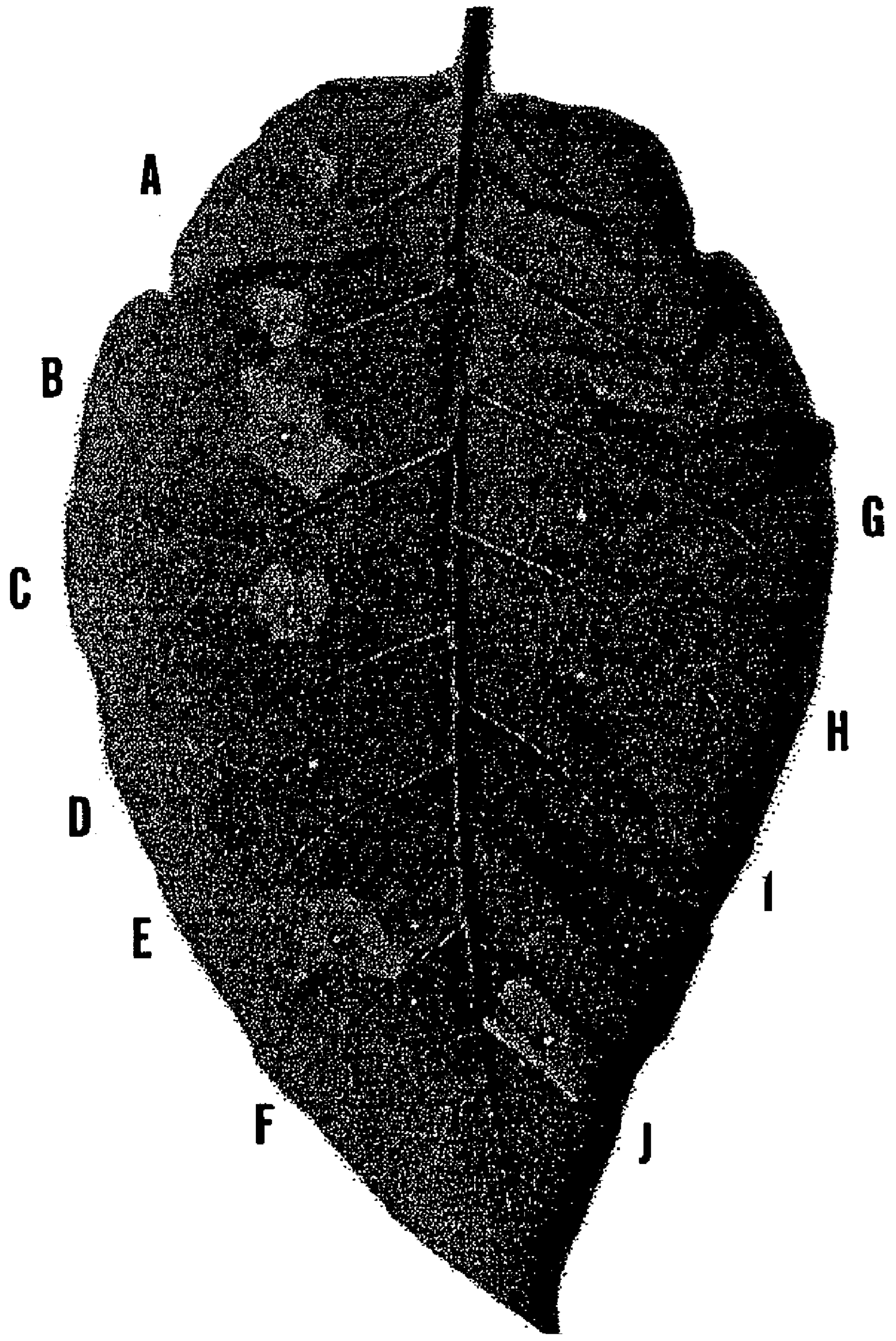
FIG. 3 is an HR assay on tobacco leaf infiltrated as follows: (1) A, harpin$_{Ea}$+raspberry IF; (2) B, harpin$_{Ea}$+apple IF; (3) C, harpin$_{Ea}$+tobacco IF; (4) D, harpin$_{Ea}$+endoproteinase Glu-C; (5) E, harpin$_{Ea}$+trypsin; (6) F, harpin$_{Ea}$; (7) G, tobacco IF; (8) H, endoproteinase Glu-C; (9) I, trypsin; and (10) J, harpin$_{Ea}$. IF refers to intracelluar fluids.
Figure 4:
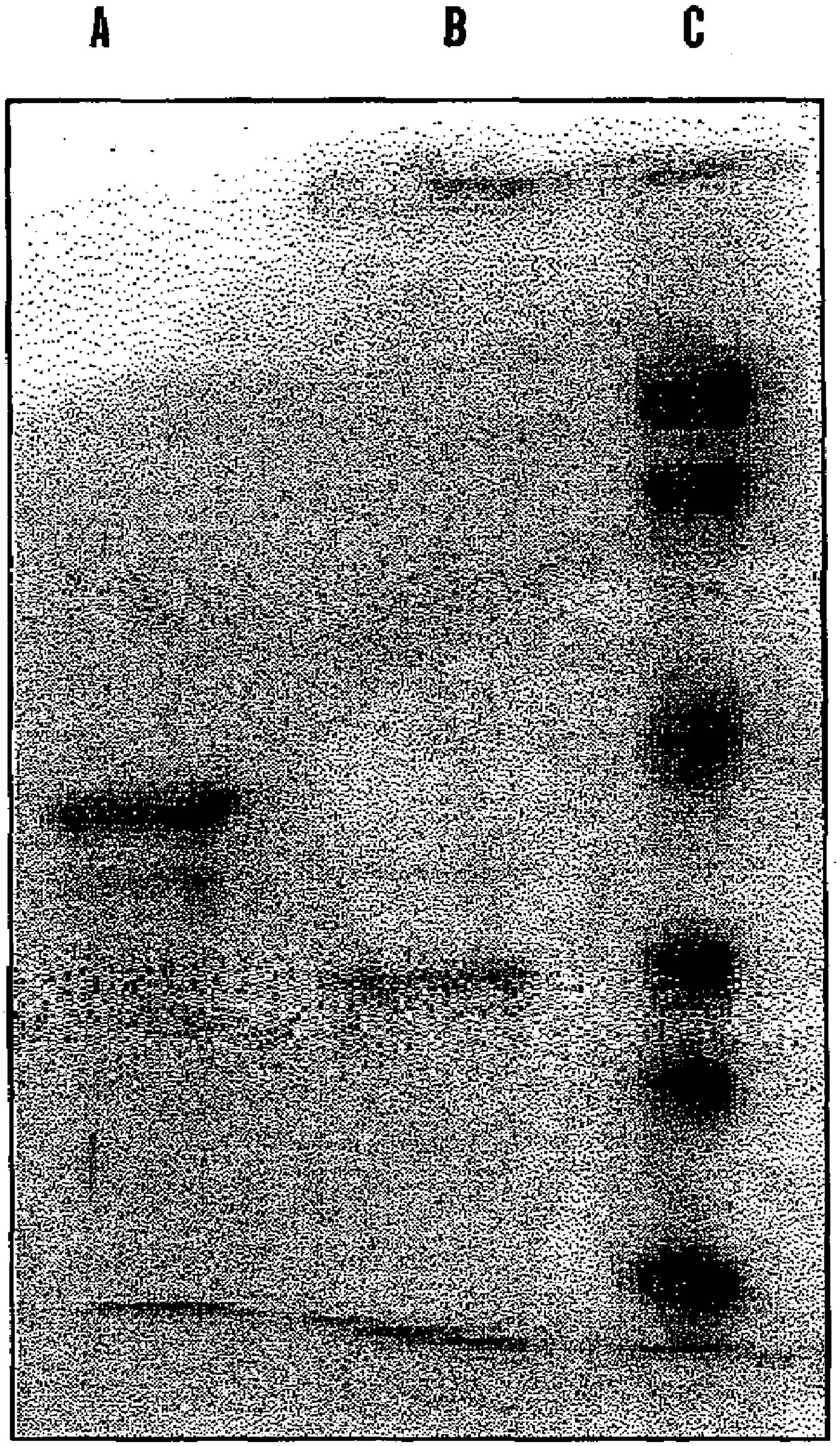
FIG. 4 shows the digestion of harpin with endoproteinase Glu-C. Lane A is harpin; Lane B is harpin+endoproteinase Glu-C; Lane C is BioRad low range molecular weight markers.

In order to generate additional harpin$_{Ea}$ fragments, purified full length protein was proteolyzed in vitro by several proteinases, including endoproteinase Glu-C, trypsin, pepsin, and papain (e.g., FIGS. 3 and 4). Harpin solutions digested with trypsin or with papain lost all activity. In contrast, following digestion with endoproteinase Glu-C, HR-eliciting activity was retained. No peptides larger than 6 kD were evident by PAGE following trypsin digestion. Endoproteinase Glu-C digestion yielded an approximately 20 kD fragment, larger than expected if all cleavage sites were cut, indicating that digestion was not complete (FIG. 4).

Example 11

Apoplastic Fluids (IF) Contain Harpin-degrading Proteolytic Activity

Figure 5A:
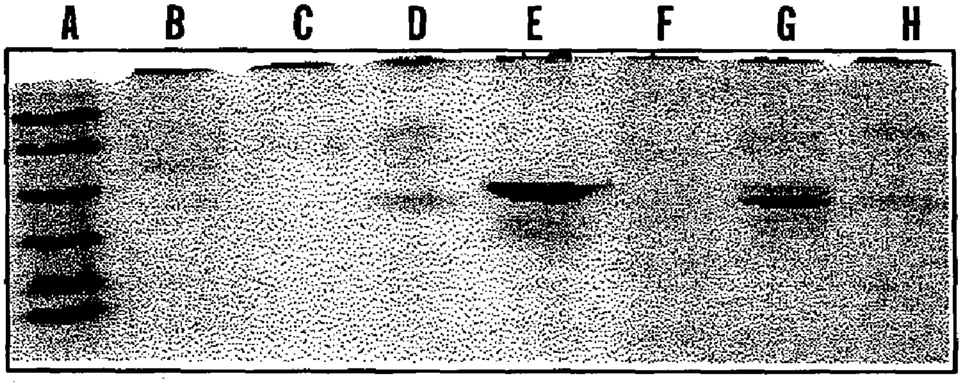
FIG. 5A shows the proteolysis of harpin. Coomáassie blue stained polyacrylamide gel was loaded as follows: A, BioRad low range molecular weight markers; B, IF-apple; C, IF-raspberry; D, IF-tobacco; E, harpin$_{Ea}$; F, harpin$_{Ea}$+IF-apple; G, harpin$_{Ea}$+IF-raspberry; H, harpin$_{Ea}$+IF-tobacco.
Figure 5B:
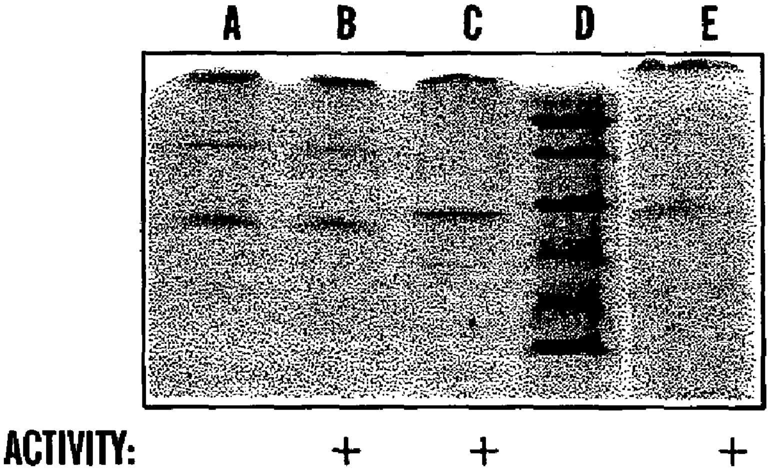
FIG. 5B shows a Coomassie Blue stained polyacrylamide gel loaded as follows: A, IF-tobacco; B, IF-tobacco+harpin$_{Ea}$; C, harpin$_{Ea}$; D, BioRad low range molecular weight markers; E, IF-tobacco+harpin$_{Ea}$+PMSF. HR-eliciting activity of the sample following proteolysis is denoted below the gel.
Figure 5C:
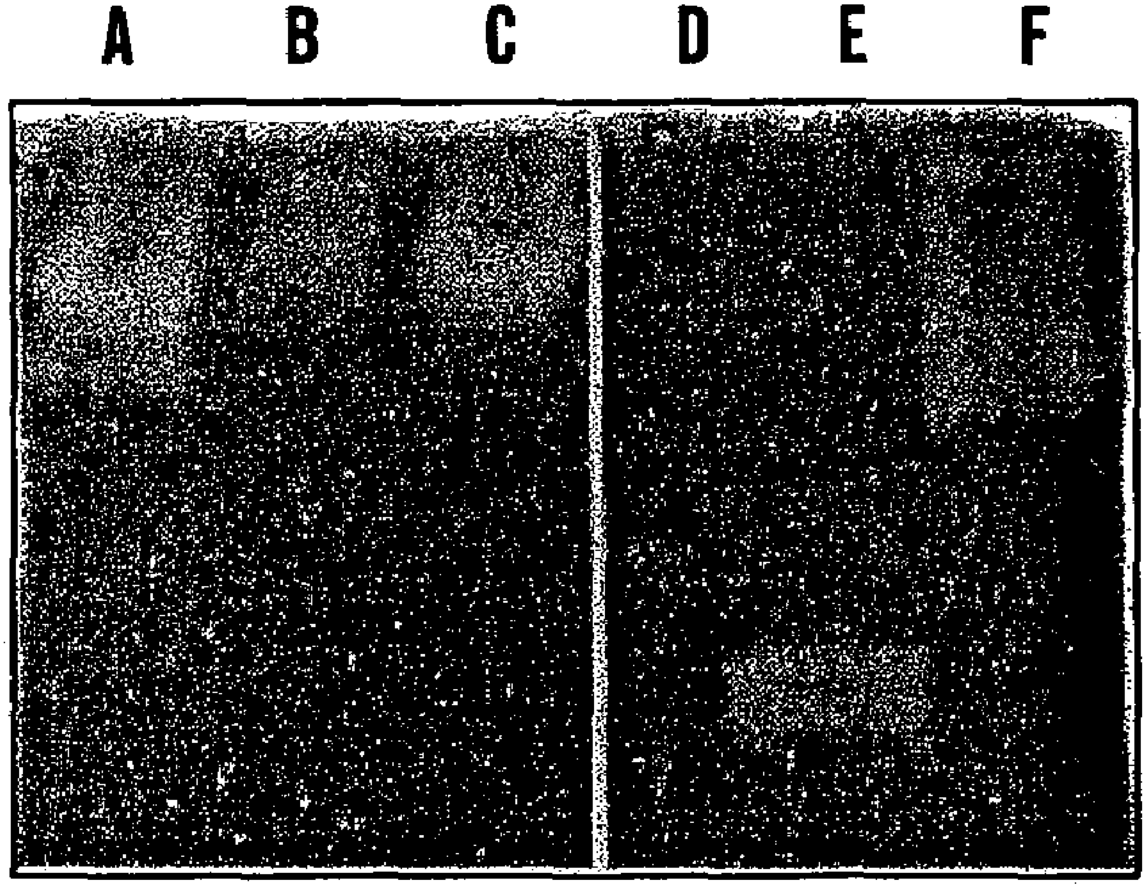
FIG. 5C depicts whether proteolytic activity is present in IF from all plants tested. Intercellular fluid harvested from several plants was analyzed by PAGE in a gel containing 0.1% copolymerized gelatin. After washing to remove SDS and incubation to allow proteolysis of gelatin, the gels were stained to demonstrate the presence of gelatinolytic activity. A, IF-apple; B, IF-tobacco; C, IF-cotoneaster; D, BioRad mw; E, endoproteinase Glu-C; and F, ground leaf extract-tobacco.

Apoplastic fluids (intercellular fluids; IF) from tobacco and other plants were also employed to proteolyze harpin. Each IF tested possessed proteinase activity(s), as indicated by the presence of multiple activity-stained bands in polyacrylamide gels containing co-polymerized gelatin (FIGS. 5A to 5C), as well as by the disappearance of detectable harpin$_{Ea}$ (Schägger, et al., "Tricine-Sodium Dodecyl Sulfate Gel Electrophoresis for the Separation of Proteins in the Range From 1 to 100 kDa," *Anal. Biochem.* 166:368–379 (1987), which is hereby incorporated by reference) following overnight digestion of purified harpin$_{Ea}$ with IF. Proteinase activity was substantially greater at 37° C. than at 20° C., and activity was higher at pH 8.5 than at pH 7. Several inhibitors were employed in order to define the proteolytic activity(s) of the IF. No single proteinase inhibitor which was employed prevented degradation of harpin$_{Ea}$. However, a mixture of the inhibitors Pepstatin A (1 μM), E-64 (1 μM), Aprotinin (2 μg/ml), and o-phenanthroline (1 mM), targeted at acid proteinases, cysteine proteinases, serine proteinases, and metalloproteinases, respectively, partially inhibited proteolysis.

Harpin$_{Ea}$ degraded by proteolytic activities present in the plant apoplast retained HR-eliciting activity (FIG. 3). In contrast, harpin$_{Ea}$ proteolyzed by a clarified extract produced by grinding tobacco leaf tissue with mortar and pestle lost HR-eliciting activity. In order to study whether apoplastic degradation of harpin was a prerequisite to its HR-eliciting activity, the length of time required for leaf collapse when either intact harpin or harpin predigested with tobacco IF was infiltrated into tobacco leaf panels was compared. Both preparations elicited the HR in a similar time frame (12–18 hours, depending on the experiment).

Example 12

Characterization of HR-eliciting Peptide Fragments

Figure 6:
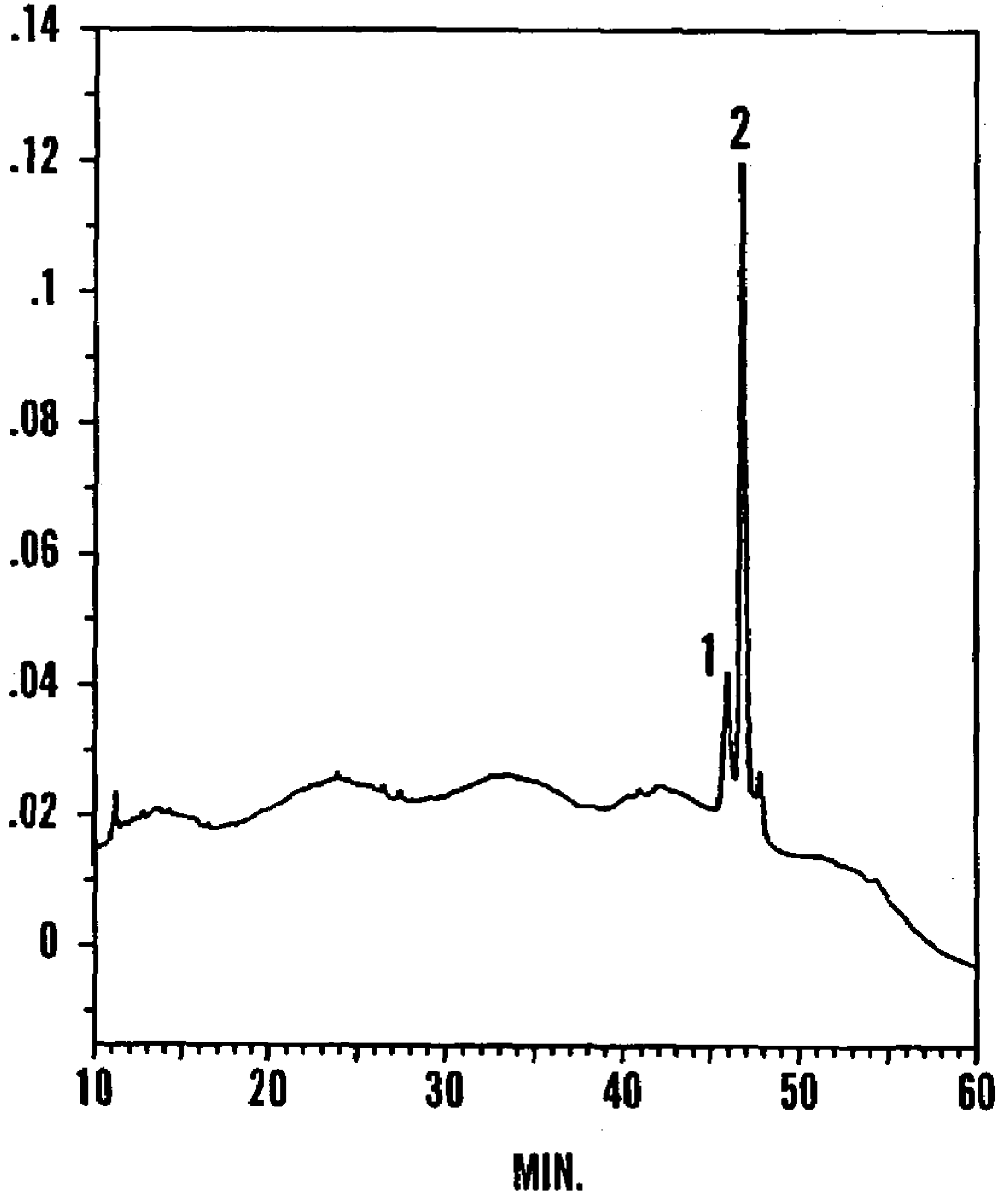
FIG. 6 shows the refractionation of elicitor-active peptides following proteolysis of harpin$_{Ea}$ by tobacco IF. Absorbance was measured at 210 nm. Peak 1 contains peptides P91 and P95; peak 2 contains peptides P65 and P69.
Figure 7:
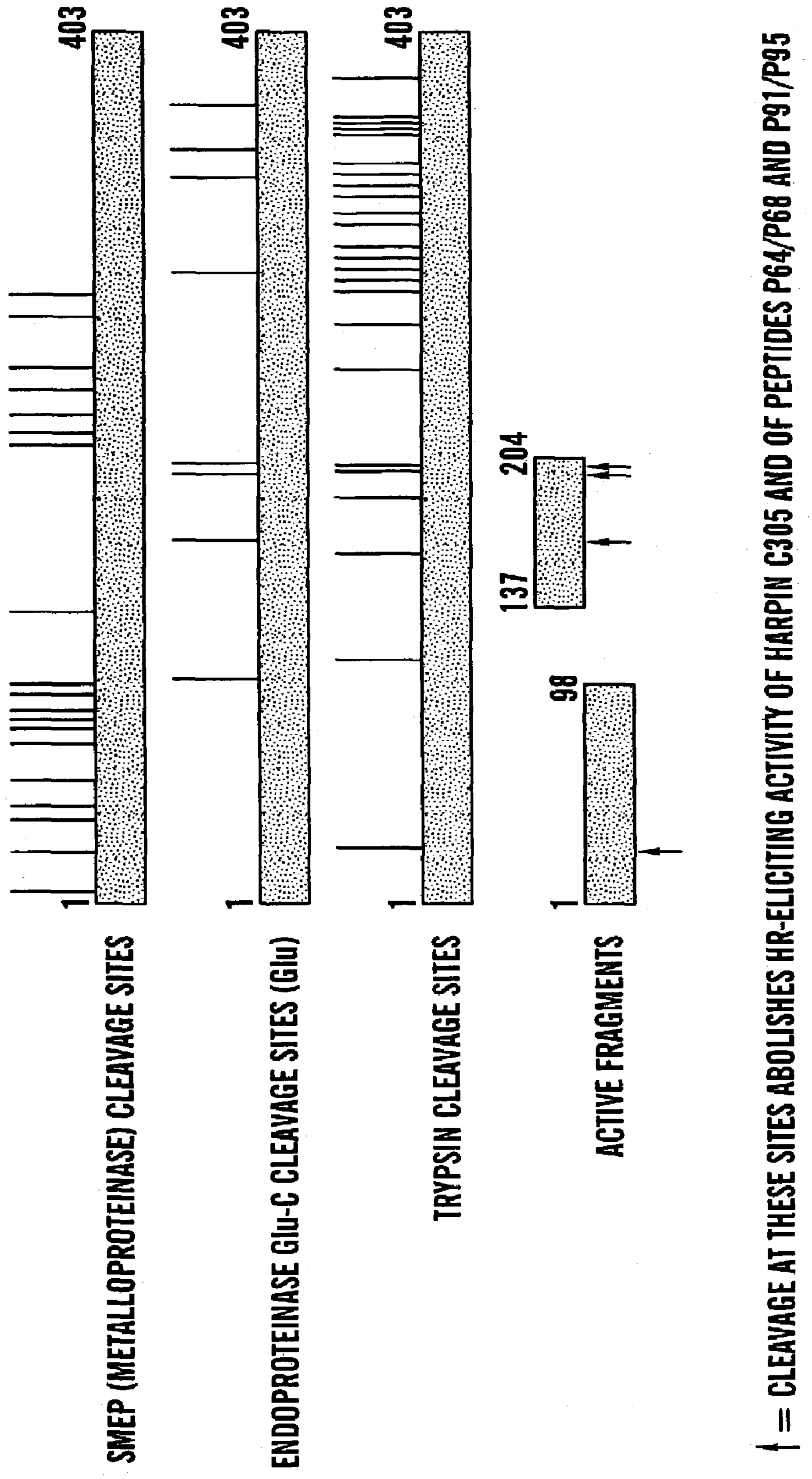
FIG. 7 shows the predicted proteolytic cleavage sites within harpin of several tested proteinases, and the effect of these cleavages on activity of active harpin fragments. Residues potentially important for HR-eliciting activity, based on the loss of activity following further cleavage, are indicated by upward-pointing arrows at bottom.
Figure 9A:
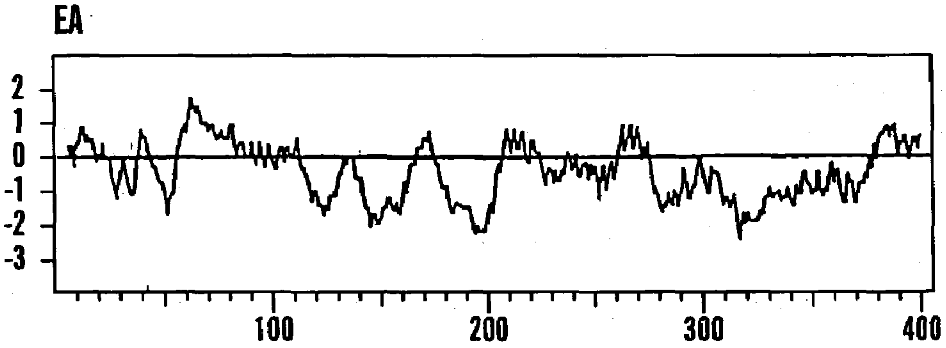
FIGS. 9A–F show Kyte-Doolittle hydropathy plots of bacterial HR-eliciting proteins. Ea, *E. amylovora* EA321 (9A); Est, *E. stewartii* DC283 (9B); Ech, *E. chrysanthemi* AC4150 (9C); Ecc, *E. cartovora* subsp. *Carotovora* (9D); Rs, *R, solanacearum* (9E); Pss, *P. syringae* pv. *syringae* (9F).
Figure 9B:
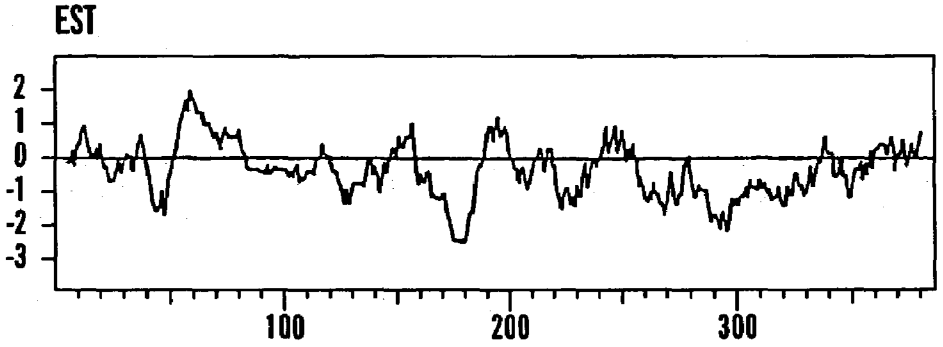
Figure 9C:
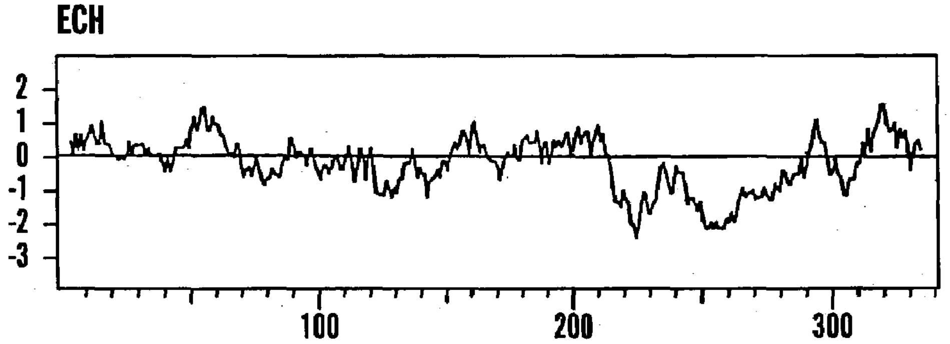
Figure 9D:
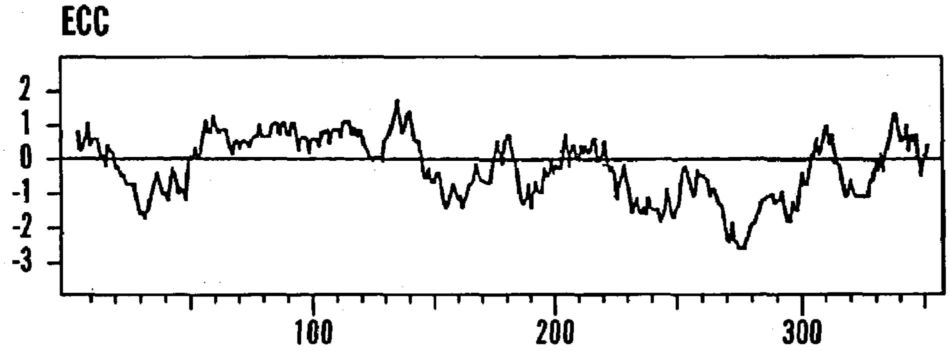
Figure 9E:
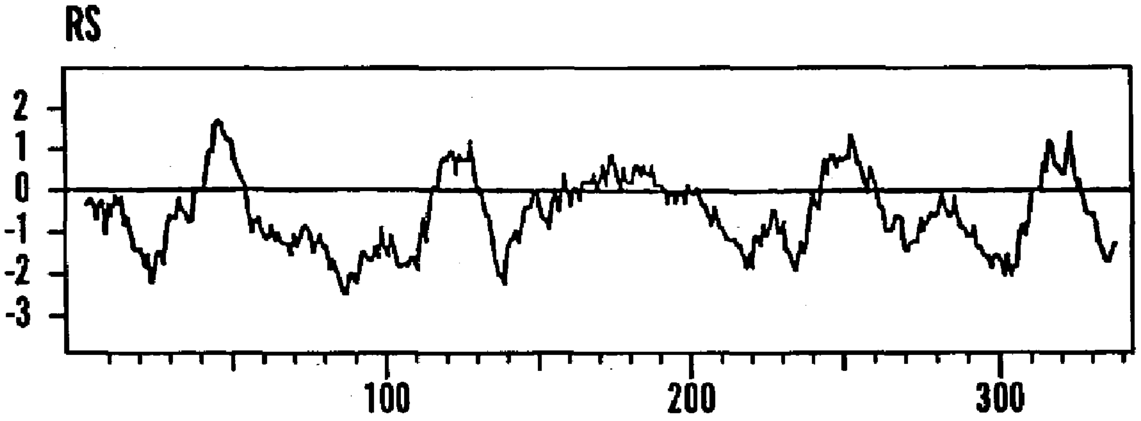
Figure 9F:
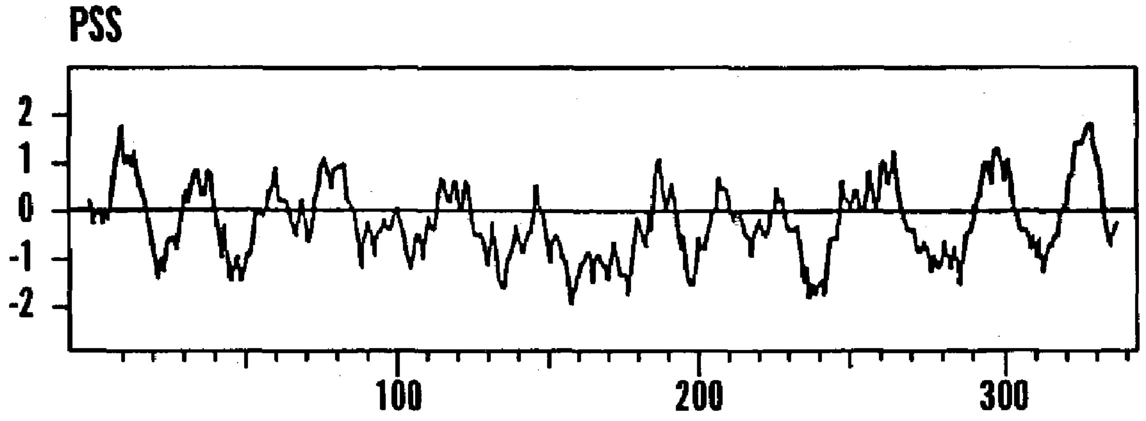

Peptides resulting from digestion by apoplastic plant proteinase(s) were fractionated by reverse phase HPLC (Vydac C18 column), and tested for activity. Following treatment of intact harpin$_{Ea}$ with tobacco IF, three fractions contained some HR-eliciting activity on tobacco. Two of the three demonstrated weak activity, and little protein was present. They were not further characterized. Fraction 19, which contained the strongest activity as well as the most protein, was refractionated using a more shallow elution gradient (FIG. 6). Refractionation, N-terminal protein sequencing, and molecular weight analysis by mass spectroscopy indicated that four largely overlapping peptides were present. Peak 19–1 contained peptides P91 and P95, corresponding to harpin$_{Ea}$ residues 110-200 and 110-204; peak 19-2 contained peptides P64 and P68, corresponding to harpin$_{Ea}$ residues 137-200 and 137-204. 19-1 and 19-2 each possessed HR-eliciting activity. The smallest peptide thus confirmed to retain activity consisted of residues 137-204. The two peptides in each peak were not separable under the conditions used. These active fragments are distinct from the smallest active N-terminal fragment (harpin$_{Ea}$C305), and indicate that more than one portion of harpin$_{Ea}$ displays activity in planta. Further digestion with trypsin abolished the HR-eliciting activity of 19-2. This proteinase cleaves P64 and P68 as shown in FIG. 7. Further digestion with endoproteinase Glu-C in ammonium bicarbonate buffer abolished the HR-eliciting activity of 19-1. Endoproteinase Glu-C is predicted to cleave P91 and P95 as shown in FIG. 7. Loss of elicitor-activity followed further digestion of these peptides with endoproteinase Glu-C or trypsin.

Example 13

E. amylovora Harpin's Similarity with Other Proteins

The predicted protein sequences of proteinaceous HR elicitors from several other bacterial plant pathogens, and of other proteins known to be, or thought to be, secreted by a type III secretion pathway were also compared with that of harpin$_{Ea}$. When harpin$_{Ea}$ was compared with elicitors from E. amylovora Ea246 (i.e. harpin$_{Ear}$), Erwinia chrysanthemi EC16 (harpin$_{Ech}$) (Bauer, et al., "Erwinia chrysanthemi harpin$_{Ech}$: An Elicitor of the Hypersensitive Response That Contributes to Soft-Rot Pathogenesis," Mol. Plant-Microbe Interact 8:484–491 (1995), which is hereby incorporated by reference), Erwinia carotovora subsp. carotovora (harpin$_{Ecc}$) (Mukherjee, et al., Presented at the 8$^{th}$ International Congress Molecular Plant-Microbe Interactions, Knoxville, Tenn. (1996), which is hereby incorporated by reference), Erwinia stewartii (Harpin$_{Es}$) (Frederick, et al., "The wts Water-Soaking Genes of Erwinia stewartii are Related to hrp genes," Presented at the Seventh International Symposium on Molecular Plant-Microbe Interactions, Edinburgh, Scotland (1994), which is hereby incorporated by reference), Ralstonia (Pseudomonas) solanacearum (PopA) (Arlat, et al., "PopA1, a Protein Which Induces a Hypersensitivity-Like Response on Specific Petunia Genotypes, is Secreted via the Hrp Pathway of Pseudomonas solanacearum," EMBO J. 13:543–553 (1994), which is hereby incorporated by reference), Pseudomonas syringae 61 (harpin$_{Pss}$) (He, et al., "Pseudomonas syringae pv. syringae harpin$_{Pss}$: a Protein That is Secreted via the Hrp Pathway and Elicits the Hypersensitive Response in Plants," Cell 73:1255–1266 (1993), which is hereby incorporated by reference), Pseudomonas syringae pv. tomato (harpin$_{Pst}$) (Preston, et al., "The HrpZ Proteins of Pseudomonas syringae pvs. syringae, glycinea, and tomato Are Encoded By An Operon Containing Yersinia ysc Homologs and Elicit the Hypersensitive Response in Tomato But Not Soybean," Mol. Plant-Microbe Interact 8:717–732 (1995), which is hereby incorporated by reference), the Erwinia-derived harpins contained significant regions of similarity at the C-terminus. In addition, all the elicitors are glycine-rich, secreted, and heat-stable. Limited similarity between harpin$_{Pss}$, and harpin$_{Ea}$ had been reported previously (He, et al., "Pseudomonas syringae pv. syringae harpin$_{Pss}$: a Protein That is Secreted via the Hrp Pathway and Elicits the Hypersensitive Response in Plants," Cell 73:1255–1266 (1993), which is hereby incorporated by reference), (Laby, et al., Presented at the Seventh International Symposium on Molecular Plant-Microbe Interactions, Edinburgh, Scotland (1994), which is hereby incorporated by reference). A limited region of similarity between harpin$_{Ea}$ and other harpins frm Erwinia spp. was also evident at the extreme N-terminus of each protein, where 9 out of the first 26 residues are conserved (FIG. 8). Kyte-Doolittle hydropathy plots for each of the harpins produced by different Erwinia spp. are illustrated in FIGS. 9A–F. Each of the Erwinia harpins examined displays a generally similar hydrophobicity profile along the full length of the protein. This profile is distinct from the profile demonstrated by PopA1 and by harpin$_{Pss}$, and does not possess the symmetry evident in the profile of those two proteins. The hydropathy profile of each Erwinia harpin is generally similar to that of the others, yet distinct from that reported for harpin$_{Pss}$ (Alfano, et al., "Analysis of the Role of the Pseudomonas Syringae HrpZ harpin in Elicitation of the Hypersensitive Response to Tobacco Using Functionally Nonpolar hrpZ Deletion Mutations, Truncated HrpZ Fragments, and hrmA Mutations," Mol. Microbiol. 19:715–728 (1996), which is hereby incorporated by reference). Harpin$_{Ecc}$ possesses a strikingly hydrophobic region around residues 54–143 (Mukherjee, et al., Presented at the 8$^{th}$ International Congress Molecular Plant-Microbe Interactions, Knoxville, Tenn. (1996), which is hereby incorporated by reference). This portion of the protein is also the most hydrophobic region of harpin$_{Ea}$ and harpin$_{Es}$. The rest of each protein is predominantly hydrophilic.

Truncated proteins and fragments of harpin obtained following proteolytic digestion of the full length protein indicate several surprising aspects of harpin$_{Ea}$ HR-eliciting activity. These harpin fragments demonstrate that HR-eliciting activity resides in distinct regions of the protein, and that relatively small fragments of the protein, as little as 68 residues and possibly less, are sufficient for this activity. Fragments of other plant pathogen-derived elicitor proteins also retain biological activity, including Avr9 from Caldosporium fulvum (Van den Ackervecken, et al., "The AVR9 Race-Specific Elicitor of Cladosporium fulvum is Processed by Endogenous and Plant Proteases," Pl. Physiol. 103:91–96 (1993), which is hereby incorporated by reference), Pep-13 of Phytophthora megasperma (Nürnburger, et al., "High Affinity Binding of a Fungal Oligopeptide Elicitor to the Parsley Plasma Membranes Triggers Multiple Defence Responses," Cell, 78:449–460 (1994), which is hereby incorporated by reference), and harpin$_{Pss}$ of P. syringae pv. syringae (Alfano, et al., "Analysis of the Role of the Pseudomonas syringae HrpZ harpin in Elicitation of the Hypersensitive Response in Tobacco Using Functionally Nonpolar hrpZ Deletion Mutations, Truncated HrpZ Fragments, and hrmA Mutations," Mol. Microbiol. 19:715–728 (1996), which is hereby incorporated by reference).

Expression of truncated harpin fragments and proteolysis of full-length harpins showed that two distinct fragments retain HR-eliciting activity. The primary sequence of each active fragment show no discernable similarity with each other, or with other elicitor-active peptides. However, the sites of cleavage by trypsin and endoproteinase Glu-C suggest portions of each fragment required for activity. It would be of interest to alter specifically the amino acid residues at or near these cleavage sites to determine whether HR-eliciting activity is altered or lost. Additionally, harpin$_{Ea}$ P64 and P68 demonstrate distinct hydrophobicity during reverse-phase HPLC (FIG. 6), and they correspond to a hydrophobic peak in a Kyte-Doolittle plot (FIG. 9). The role of this putative hydrophobic domain could be tested by mutagenesis, or by synthesis of altered peptides. However, the fact that multiple fragments independently possess HR-eliciting activity complicates analysis of full-length proteins.

This finding, that fragments of the protein retain HR-eliciting activity, also allowed (at least) two apoplastic proteinase activities, which are distinct from intracellular plant proteinases, to be defined. Two apoplastic plant proteinases (from soybean) have been studied in some detail. SMEP, a metalloproteinase (Huangpu, et al., "Purification and Developmental Analysis of an Extracellular Proteinase From Young Leaves of Soybean," *Plant Physiol* 108:969–974 (1995); McGeehan, et al., "Sequencing and Characterization of the Soybean Leaf Metalloproteinase," *Plant Physiol.* 99:1179–1183 (1992), which are hereby incorporated by reference) sensitive to EDTA, is thought to cleave at G/L and G/I. Interestingly, although there are 19 potential SMEP cleavage sites in the intact harpin$_{Ea}$, only one of them is located within fragments P91 and P95, and none are within fragments P64 and P68 (FIG. 7). P91 and P95 thus may represent partial digestion products of a SMEP-like proteinase in the tobacco apoplast. The other studies soybean apoplastic proteinase, SLAP, a sulfhydryl proteinase (Huangpu, et al., "Purification and Developmental Analysis of an Extracellular Proteinase From Young Leaves of Soybean," *Plant Physiol.* 108:969–974 (1995), which is hereby incorporated by reference) sensitive to p-chloromercuribenzoic acid (pCMB). Several lines of evidence suggest that multiple proteolytic activities in the IF are degrading harpin$_{Ea}$. PMSF, a serine protease inhibitor, decreases but does not entirely block harpin$_{Ea}$ degradation (FIG. 5C); no single proteinase inhibitor tested blocks harpin degradation, and the cleavage sites after residues 109, 136, 200, and 204 are dissimilar. Endoproteinase Glu-C does not abolish activity of full-length harpin, but does abolish activity of P91 and P95 (and presumably P64 and P68); trypsin abolishes the activity of P64 and P68 (and presumably P91 and P95). These final digests suggest specific portions of each distinct HR-eliciting peptide which are presumably necessary for its activity, as mentioned previously.

The apoplastic activities degrade harpin without destroying its HR-eliciting ability, in contrast to intracellular proteolytic activities present in a ground leaf-extract, which abolish activity. This raises a number of intriguing questions, e.g., does the plant use these harpin fragments as elicitor-signals? The timing of the HR was examined when full length harpin and harpin predigested by tobacco intercellular fluid were each infiltrated into tobacco leaves. The HR elicited by each preparation occurred 12–18 hours after infiltration. Co-infiltration of proteinase inhibitors into tobacco leaf panels along with harpin also had no effect on harpin's HR eliciting activity, although limited proteolytic degradation cannot be ruled out in this case, particularly since it seems that at least two, and perhaps more, apoplastic proteinases are present in tobacco. Because predigested harpin elicited the HR no faster than undigested protein, proteolytic digestion seems unlikely to be a rate-limiting step required for HR to occur. The role of these apoplastic proteinases which are able to hydrolyze harpin partially, yet unable to abolish harpin's HR-eliciting activity on tobacco, remains unclear. Salzer et al., "Rapid Reactions of Spruce-Cells to Elicitors Released From the Ectomycorrhizal Fungus *Hebeloma crustuliniforme* and Inactivation of These Elicitors by Extracellular Spruce Cell Enzymes," *Planta* 198:118–126 (1996), which is hereby incorporated by reference, have noted that spruce (*Picea abies* (L.) Karst.) modulates the level of fungal cell wall elicitors released by the ectomycorrhizal fungus *Hebeloma crustuliniforme* by inactivating these molecules in the apoplast. They propose that *Picea* controls the elicitor level as part of its symbiotic interaction with the fungus. Similarly, PGIP of *Phaseolus vulgaris* has been suggested to modulate the level of elicitor-active oligogalacturonides present during the plant-parasite interaction in bean (Desiderio, et al., "Polygalacturonase, PGIP, and Oligogalacturonides in Cell-Cell Communication," *Biochem. Sci. Trans.* 22:394–397 (1994), which is hereby incorporated by reference). Perhaps the retention of HR-eliciting activity by harpin fragments contributes to the ability of plants to recognize the presence of a pathogen. In this regard, it would be interesting to explore whether transgenic host and non-host plants, engineered for apoplastic expression of a harpin activity-degrading proteinase, would exhibit reduced or increased sensitivity to *E. amylovora,* compared to non-engineered plants.

Despite numerous attempts, only a handful of truncated derivatives of harpin$_{Ea}$ and harpin$_{Ear}$ were successfully expressed from portions of hrpN. Problems with protein stability were evident in that several truncated harpins were unstable and difficult to purify. Additionally, expression of truncated harpins may be deleterious to bacteria. Truncated harpin$_{Ea}$C31 was, however, stable and easily purified, but not secreted, suggesting that C-terminal sequences are involved in harpin secretion. Unfortunately, the presence of vector-encoded amino acids in this protein complicates this conclusion. All attempts to clone β-galactosidase-harpin fusion proteins have been unsuccessful, as were attempts to clone and express hrpN downstream of the lacZ promoter in several commonly used vectors such as pBluescript. Expression of such constructs is evidently deleterious to bacterial strains.

Wei, et al., "Harpin, Elicitor of the Hypersensitive Response Produced By the Plant Pathogen *Erwinia amylovora," Science,* 257:85–88 (1992), which is hereby incorporated by reference, reported previously that BLAST searches indicated harpin$_{Ea}$ possessed slight similarity to several other glycine-rich proteins, including keratins and glycine-rich cell wall proteins. However, this is thought to be due to the high glycine content of harpin$_{Ea}$, and as such does not suggest a role for harpin$_{Ea}$. Examination of N-terminal sequences from several HR-eliciting proteins produced by phytopathogenic bacteria (FIG. 8) yielded some potential similarities. However, the region in question is quite short. The region of putative primary sequence similarity is limited to the first 26 residues at the N-terminus, and its role remains unclear. Surprisingly, *E. carotovora* harpin$_{Ecc}$ appears more similar to the harpins from *E. amylovora* and *E. stewartii* than to that from *E. chrysanthemi,* to which it is more closely related with respect to its taxonomic position as well as its mechanism of pathogenicity (i.e. soft-rots). In addition, although primary sequence similarity is strongest only in the C-terminal third of each protein, the *Erwinia* harpins possess broadly similar hydrophobicity profiles along their entire lengths (FIG. 9). Based on its hydrophobicity profile, Alfano, et al., "Analysis of the Role of the *Pseudomonas syringae* HrpZ harpin in Elicitation of the Hypersensitive Response in Tobacco Using Functionally Nonpolar hrpZ Deletion Mutations, Truncated HrpZ Fragments, and hrmA Mutations," *Mol. Microbiol.* 19:715–728 (1996), which is hereby incorporated by reference, speculated that harpin$_{Pss}$ may have an amphiphilic nature. However, the *Erwinia* harpins' profiles do not match that of harpin$_{Pss}$.

Recently, a number of other secreted glycine-rich pathogenicity associated proteins, elicitors of the HR or other plant-defense responses, have been described from other plant pathogenic bacteria and fungi (Boller, "Chemoperception of Microbial Signals in Plant Cells," *Ann. Rev. Plant Physiol. Plant Molec. Biol.* 46:189–214 (1996), which is hereby incorporated by reference), including *Phytophthora megasperma* (Ballieul, et al., "A New Elicitor of the Hypersensitive Response in Tobacco: a Fungal Glycoprotein Elicits Cell Death, Expression of Defence Genes, Production of Salicylic Acid, and Induction of Systemic Acquired Resistance," *Plant Journal* 8:551–560 (1995); Nürnburger, et al., "High Affinity Binding of a Fungal Oligopeptide Elicitor to the Parsley Plasma Membranes Triggers Multiple Defence Responses," *Cell* 78:449–460 (1994), which are hereby incorporated by reference), and *Magnaporthe grisea* (Sweigard, et al., "Identification, Cloning, and Characterization of PWL2, a Gene For Host Species Specificity in the Rice Blast Fungus," *Plant Cell* 7:1221–1233 (1995), which is hereby incorporated by reference). Proteinaceous HR-elicitors have also now been described from *Phynchosporium secalis* (Rohe, et al., "The Race-Specific Elicitor, NIP 1, From the Barley Pathogen, *Rhynchosporium secalis*, Determines Avirulence on Host Plants of the Rrs1 Resistance Genotype," *EMBO Journal* 14:4168–4177 (1995) which is hereby incorporated by reference, while *P. infestans* (Pieterse, et al., "Structure and Genomic Organization of the ipiB and ipiO Gene Clusters of *Phytophthora infestans*," *Gene*, 138:67–77 (1994), which is hereby incorporated by reference) produces a glycine-rich pathogenicity-associated family of proteins of unknown function. Because the primary amino acid sequence of each elicitor protein or peptide fragment shows no obvious similarity to that of the others, it is unclear whether they interact with the same target on or in the plant cell, plasma membrane, or cell wall. In that regard, it might be of interest to test whether any one of these molecules inhibits the action of other(s). The increasing availability of peptides such as Pep13, Avr9, P68, and harpin$_{Ea}$ C305 with plant-defense response-eliciting activity (HR and otherwise) should enable precise probing of their targets on or in plant cells, as well as determination of whether their mechanisms of activity are similar, distinct, or overlapping.

Example 14

Bacterial Strains and Plasmids

*Escherichia coli* stains used in the following examples include DH5α and BL21(DE3) purchased from Gibco BRL and Stratagene, respectively. The pET28(b) vector was purchased from Novagen. Eco DH5α/2139 contained the complete hrpN gene. The 2139 construct was produced by D. Bauer at the Cornell University. The hrpN gene was cleaved from the 2139 plasmid by restriction enzyme digestion with HindIII, then purified from an agarose gel to serve as the DNA template for PCR synthesis of truncated hrpN clones. These clones were subsequently inserted into the (His)$_6$ vector pET28(b) which contained a Kan$^r$ gene for selection of transformants.

Example 15

DNA Manipulation

Restriction enzymes were obtained from Boehringer Mannheim or Gibco BRL. T4 DNA ligase, Calf Intestinal Alkaline Phosphatase (CIAP), and PCR Supermix™ were obtained from Gibco BRL. The QIAprep Spin Miniprep Kit, the Qiagen Plasmid Mini Kit, and the QIAquick PCR Purification Kit were purchased from Qiagen. The PCR primers were synthesized by Lofstrand Labs Limited (Gaithersburg, Md.). The oligopeptides were synthesized by Bio-Synthesis, Inc. (Lewisville, Tex.). All DNA manipulations such as plasmid isolation, restriction enzyme digestion, DNA ligation, and PCR were performed according to standard techniques (molecular cloning) or protocols provided by the manufacturer.

Example 16

Fragmentation of hrpN Gene

Figure 10:
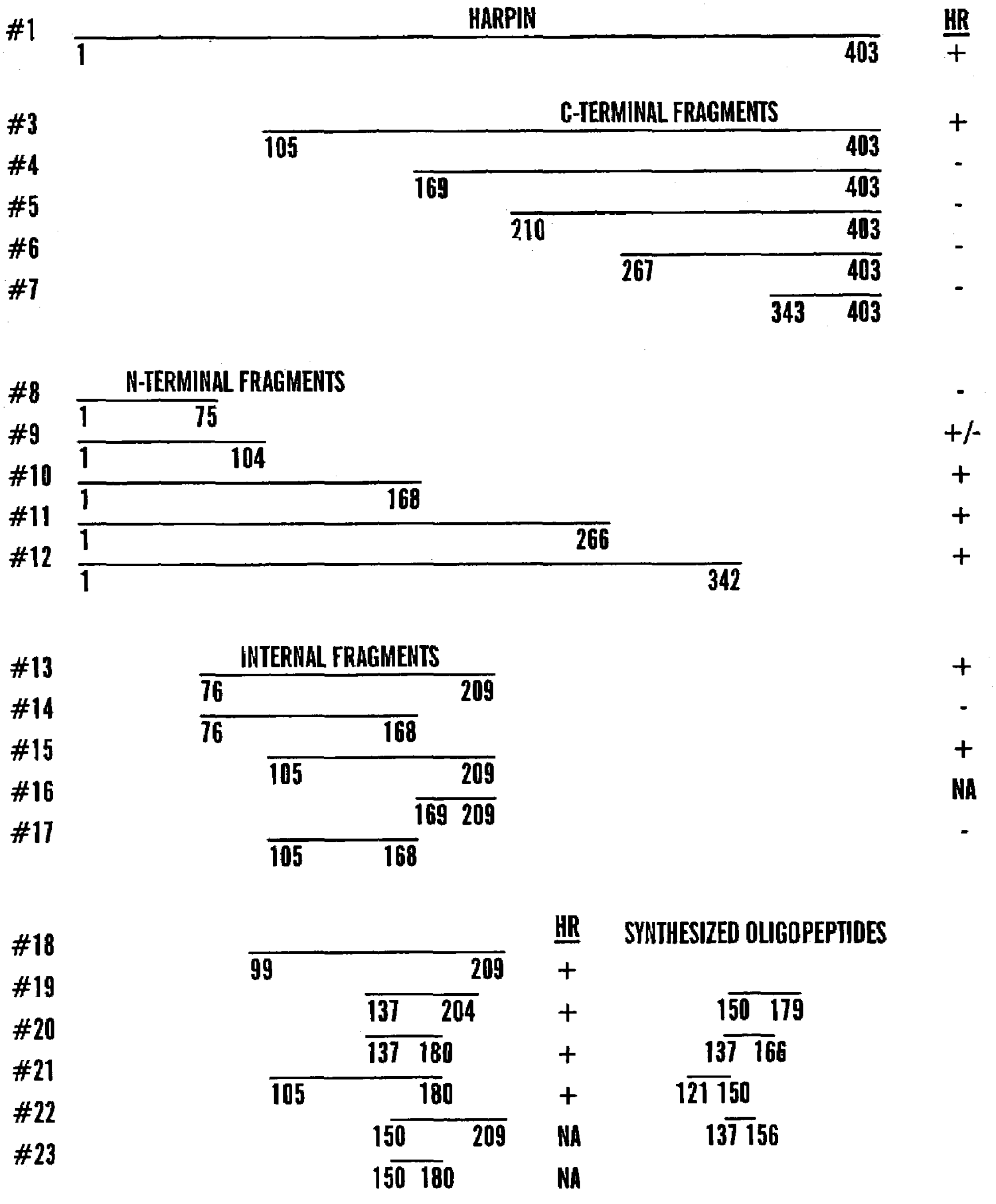
FIG. 10 shows truncated proteins of the hypersensitive response elicitor protein or polypeptide.

A series of N-terminal and C-terminal truncated hrpN genes and internal fragments were generated via PCR (FIG. 10). The full length hrpN gene was used as the DNA template and 3' and 5' primers were designed for each truncated clone (FIG. 11). The 3' primers contained in the NdeI enzyme cutting site which contained the start codon ATG (Methionine) and the 5' primers contained the stop codon TAA and a HindIII enzyme cutting site for ligation into the pET28(b) vector. PCR was carried out in 0.5 ml tubes in a GeneAmp™ 9600 or 9700. 45 μl of Supermix™ were mixed with 20 pmoles of each pair of DNA primers, 10 ng of full length harpin DNA, and di$H_2O$ to a final volume of 50 μl. After heating the mixture at 95° C. for 2 min, the PCR was performed for 30 cycles at 94° C. for 1 min, 58° C. for 1 min and 72° C. for 1.5 min. The PCR products were verified on a 6% TBE gel (Novex). Amplified DNA was purified with the QIAquick PCR purification kit, digested with Nde I and Hind III at 37° C. for 5 hours, extracted once with phenol:chloroform:isoamylalcohol (25:25:1) and precipitated with ethanol. 5 μg of pET28(b) vector DNA were digested with 15 units of Nde 1 and 20 units of Hind III at 37° C. for 3 hours followed with CIAP treatment to reduce the background resulting from incomplete single enzyme digestion. Digested vector DNA was purified with the QIAquick PCR purification kit and directly used for ligation. Ligation was carried out at 14–16° C. for 5–12 hours in a 15 μl mixture containing ca. 200 ng of digested pET28(b), 30 ng of targeted PCR fragment, and 1 unit T4 DNA ligase. 5–7.5 μl of ligation solution were added to 100 μl of DH5α competent cells in a 15 ml falcon tube and incubated on ice for 30 min. After a heat shock at 42° C. for 45 seconds, 0.9 ml SOC solution or 0.45 ml LB media were added to each tube and incubated at 37° C. for 1 hour. 20, 100, and 200 μl of transformed cells were placed onto LB agar with 30 μg/ml of kanamycin and incubated at 37° C. overnight. Single colonies were transferred to 3 ml LB-media and incubated overnight at 37° C. Plasmid DNA was prepared from 2 ml of culture with the QIAprep Miniprep kit. The DNA from the transformed cells was analyzed by restriction enzyme digestion or partial sequencing to verify the success of the transformations. Plasmids with the desired DNA sequence were transferred into the BL21 strain using the standard chemical transformation method as indicated above. A clone containing the full length harpin protein in the pet28(b)

vector was generated as a positive control, and a clone with only the pET28(b) vector was generated as a negative control.

Example 17

Expression of Harpin Truncated Proteins

*Escherichia coli* BL21 (DE3) strains containing the hrpN clones were grown in Luria broth medium (g/L Difco Yeast extract, 10 g/L Difco Tryptone, 5 g/L NaCl, and 1 mM NaOH) containing 30 μg/ml of kanamycin at 37° C. overnight. The bacteria were then inoculated into 100 volumes of the same medium and grown at 37° C. to an $OD_{620}$ of 0.6–0.8. The bacteria were then inoculated into 250 volumes of the same medium and grown at 37° C. to an $OD_{620}$ of ca. 0.3 or 0.6–0.8. One milli molar IPTG was then added and the cultures grown at 19° C. overnight (ca. 18 hours). Not all of the clones were successfully expressed using this strategy. Several of the clones had to be grown in Terrific broth (12 g/L Bacto Tryptone, 24 g/L Bacto yeast, 0.4% glycerol, 0.17 M $KH_2PO_4$, and 0.72 $K_2HPO_4$), and/or grown at 37° C. after IPTG induction, and/or harvested earlier than overnight (Table 2).

TABLE 2

Expression of harpin truncated proteins

| Fragment | amino acids (SEQ. ID. No. 23) | Growth medium | Induction O.D. | Expression temp. | Harvest time |
|---|---|---|---|---|---|
| 1 (+control) | 1–403 | LB | ca. 0.3 or 0.6–0.8 | 19° C. or 25° C. | 16–18 hr |
| 2 (+control) | — | LB and TB | ca. 0.3 or 0.6–0.8 | 19 C. and 37 C. | 16–18 hr |
| 3 | 105–403 | LB | 0.6–0.8 | 19° C. | 16–18 hr |
| 4 | 169–403 | TB | ca. 0.3 | 19° C. | 16–18 hr |
| 5 | 210–403 | LB or M9ZB | 0.6–0.8 | 19° C. | 16–18 hr |
| 6 | 257–403 | LB or M9ZB | 0.6–0.8 | 19° C. | 16–18 hr |
| 7 | 343–403 | LB | ca. 0.3 | 19° C. | 5 hr |
| 8 | 1–75 | TB | ca. 0.3 | 37° C. | 16–18 hr |
| 9 | 1–104 | TB | ca. 0.3 | 37° C. | 16–18 hr |
| 10 | 1–168 | TB | ca. 0.3 | 37° C. | 16–18 hr |
| 11 | 1–266 | LB | ca. 0.3 | 37° C. | 4 hr |
| 12 | 1–342 | LB | 0.6–0.8 | 19° C. | 16–18 hr |
| 13 | 76–209 | LB | ca. 0.3 | 37° C. | 5 hr |
| 14 | 76–168 | TB or LB | ca. 0.3 | 37° C. | 3 hr or 16–18 hr |
| 15 | 105–209 | M9ZB | ca. 0.3 | 37° C. | 3 hr |
| 16 | 169–209 | | no expression | | |
| 17 | 105–168 | LB | ca. 0.3 | 37° C. | 3–5 hr |
| 18 | 99–209 | LB | ca. 0.3 | 37° C. | 3 hr |
| 19 | 137–204 | LB | ca. 0.3 | 37° C. | 3 hr |
| 20 | 137–180 | LB | ca. 0.3 | 37° C. | 16–18 hr. |
| 21 | 105–180 | LB | ca. 0.3 | 37° C. | 3 hr |
| 22 | 150–209 | | no expression | | |
| 23 | 150–180 | | no expression | | |

General expression method: *Escherichia coli* BL21 (DE3) strains containing the hrpN subclones were grown in Luria broth medium (5 g/L Difco Yeast extract, 10 g/L Difco Tryptone, 5 g/L NaCl, and 1 mM NaOH) containing 30 μg/ml of kanamycin at 37° C. overnight. The bacteria were then inoculated into 100 volumes of the same medium and grown at 37° C. to an $OD_{620}$ of 0.6–0.8. The bacteria were then inoculated into 250 volumes of the growth medium and grown at 37° C. to a specific induction $OD_{620}$. One milli molar IPTG was then added and the cultures grown at an optimal temperature for protein expression, and harvested at a particular time for recovery of the highest level of protein.

Example 18

Small Scale Purification of Harpin Truncated Proteins (Verification of Expression)

A 50 ml culture of a hrpN clone was grown as above to induce expression of the truncated protein. Upon harvesting of the culture, 1.5 ml of the cell suspension were centrifuged at 14,000 rpm for 5 minutes, re-suspended in urea lysis buffer (8 M urea, 0.1 M $Na_2HPO_4$, and 0.01 M Tris—pH 8.0), incubated at room temperature for 10 minutes, then centrifuged again at 14,000 rpm for 10 minutes, and the supernatant saved. A 50 μl aliquot of a 50% slurry of an equilibrated $(His)_6$-binding nickel agarose resin was added to the supernatant and mixed at 4° C. for one hour. The nickel agarose was then washed three times with urea washing buffer (8 M urea, 0.1 M $Na_2HPO_4$, and 0.01 M Tris—pH 6.3), centrifuging at 5,000 rpm for five minutes between washings. The protein was eluted from the resin with 50 μl of urea elution buffer (8 M urea, 0.1 M $Na_2HPO_4$, 0.01 M Tris, and 0.1 M EDTA—pH 6.3). The eluate was run on a 4–20%, a 16%, or a 10–20% Tris-Glycine pre-cast gel depending upon the size of the truncated protein to verify the expression.

Example 19

Induction of HR in Tobacco

A 1.5 ml aliquot from the 50 ml cultures grown for small scale purification of the truncated proteins was centrifuged at 14,000 rpm for four minutes and re-suspended in an equal volume of 5 mM potassium phosphate buffer, pH 6.8. The cell suspension was sonicated for ca. 30 seconds then diluted 1:2 and 1:10 with phosphate buffer. Both dilutions plus the neat cell lysate were infiltrated into the fourth to ninth leaves of 10–15 leaf tobacco plants by making a hole in single leaf panes and infiltrating the bacterial lysate into the intercellular leaf space using a syringe without a needle. The HR response was recorded 24–48 hr post infiltration. Tobacco (*Nicotiana tabacum* v. Xanthi) seedlings were grown in an environmental chamber at 20–25° C. with a photoperiod of 12-h light/12-h dark and ca. 40% RH. Cell lysate was used for the initial HR assays (in order to screen the truncated proteins for HR activity) as the small scale urea purification yielded very little protein which was denatured due to the purification process.

Example 20

Large Scale Native Purification of Harpin Truncated Proteins for Comprehensive Biological Activity Assays Six 500 ml cultures of a hrpN clone were grown as described earlier to induce expression of the truncated protein. Upon harvesting of the culture the cells were centrifuged at 7,000 rpm for 5 minutes, re-suspended in imidazole lysis buffer (5 mM imidazole, 0.5 M NaCl, 20 mM Tris) plus Triton X-100 at 0.05% and lysozyme at 0.1 mg/ml, and incubated at 30° C. for 15 minutes, sonicated for two minutes, then centrifuged again at 15,000 rpm for 20 minutes, and the supernatant was saved. A 4 ml aliquot of a 50% slurry of an equilibrated $(His)_6$-binding nickel agarose resin was added to the supernatant and mixed at 4° C. for ca. four hours. The nickel agarose was then washed three times with imidazole washing buffer (20 mM imidazole, 0.5 M NaCl, and 20 mM Tris), centrifuging at 5,000 rpm for five minutes between washings, then placed in a disposable chromatography column. The column was centrifuged at 1100 rpm for one minute to remove any residual wash buffer and then the protein was eluted from the resin with 4 ml of imidazole elution buffer (1 M imidazole, 0.5 M NaCl, and 20 mM Tris) by incubating the column with the elution buffer for ten minutes at room temperature and then centrifuging the column at 1100 rpm for one minute. The eluate was run on a 4–20%, a 16%, or a 10–20% Tris-Glycine pre-cast gel depending upon the size of the truncated protein to verify the expression. The concentration of the proteins was determined by comparison of the protein bands with a standard protein in the Mark 12 molecular weight marker.

Example 21

Large Scale Urea Purification of Harpin Truncated Proteins for Comprehensive Biological Activity Assay The procedure was the same as the large scale native purification except that urea lysis buffer, washing buffer, and elution buffer were used, and the cells were not sonicated as in the native purification. After purification, the protein was renatured by dialyzing against lower and lower concentrations of urea over an eight hour period, then dialyzing overnight against 10 mM Tris/20 mM NaCl. The renaturing process caused the N-terminal proteins to precipitate. The precipitated 1–168 protein was solubilized by the addition of 100 mM Tris-HCl at pH 10.4 then heating the protein at 30° C. for ca. one hour. The concentration of the protein was determined by comparison of the protein bands with a standard protein in the Mark 12 molecular weight marker. The 1–75 and 1–104 protein fragments were not successfully solubilized using this strategy so they were sonicated in 100 mM Tris-HCl at pH 10.4 to solubilize as much of the protein as possible and expose the active sites of the protein for the biological activity assays.

Example 22

Expression of Harpin Truncated Proteins

The small scale expression and purification of the fragment proteins was done to screen for expression and HR activity (Table 3).

TABLE 3

Expression and HR activity of harpin truncated proteins (small scale screening)

| Fragment # | Amino Acids (SEQ. ID. No. 23) | Expression | HR activity |
|---|---|---|---|
| 1(+control) | 1–403 | + | + |
| 2(−control) | — | background protein only | − |
| 3 | 105–403 | + | + |
| 4 | 169–403 | + | − |
| 5 | 210–403 | + | − |
| 6 | 267–403 | + | − |
| 7 | 343–403 | +/− | − |
| 8 | 1–75 | + | − |
| 9 | 1–104 | + | +/− |
| 10 | 1–168 | + | + |
| 11 | 1–266 | + | + |
| 12 | 1–342 | + | + |
| 13 | 76–209 | + | + |
| 14 | 76–168 | + | − |
| 15 | 105–209 | + | + |
| 16 | 169–209 | − | − |
| 17 | 105–168 | + | − |
| 18 | 99–209 | + | + |
| 19 | 137–204 | + | + |
| 20 | 137–180 | + | + |
| 21 | 105–180 | + | + |
| 22 | 150–209 | − | − |
| 23 | 150–180 | − | − |

All of the cloned fragment proteins were expressed to a certain degree except for three small fragments (amino acids 169–209, 150–209, and 150–180). The fragments were expressed at varying levels. Fragments 210–403 and 267–403 were expressed very well, yielding a high concentration of protein from a small scale purification, resulting in a substantial protein band on SDS gel electrophoresis. Other fragments (such as a.a 1–168 and 1–104) produced much less protein, resulting in faint protein bands upon electrophoresis. It was difficult to determine whether fragment 343–403, the smallest C-terminal protein, was expressed, as there were several background proteins apparent on the gel, in addition to the suspected 343–403 protein. The positive and negative control proteins, consisting of the full length harpin protein and only background proteins, respectively, were tested for expression and HR activity as well.

The large scale expression and purification of the fragment proteins was done to determine the level of expression and titer of the HR activity (Table 4).

TABLE 4

Expression level and HR titer of harpin truncated proteins (large sale purification)

| Fragment # | Amino acids (SEQ. ID. No. 23) | Expression | HR titer |
|---|---|---|---|
| 1(+control) | 1–403 | 3.7 mg/ml | 5–7 µg/ml |
| 2(−control) | — | — | 1:2 dilution |
| 4 | 169–403 | 2 mg/ml | — |
| 5 | 210–403 | 5 mg/ml | — |
| 6 | 267–403 | 4 mg/ml | — |
| 7 | 343–402 | 200 µg/ml | — |
| 8 | 1–75 | 50 µg/ml | — |
| 9 | 1–104 | 50 µg/ml | 3 µg/ml (1:16 dilution) |
| 10 | 1–168 | 1 mg/ml | 1 µg/ml |
| 13 | 76–209 | 2.5 mg/ml | 5 µg/ml |
| 14 | 76–168 | 2 mg/ml | — |
| 15 | 105–209 | 5 mg/ml | 5–10 µg/ml |
| 17 | 105–168 | 250 µg/ml | — |
| 19 | 137–204 | 3.6 mg/ml | 3.5 µg/ml |
| 20 | 137–180 | 250 µg/mi | 16 g/ml |

Not all of the proteins were expressed in large scale due to time constraints. The truncated proteins deemed to be the most important in characterizing harpin were chosen. The positive control (full length harpin) was expressed in a relatively high level at 3.7 mg/ml. All of the C-terminal proteins were expressed at relatively high levels from 2–5 mg/ml, except for fragment 343–403 as discussed earlier. The N-terminal fragments were expressed very well also, however, during the purification process, the protein precipitated and very little was resolubilized. The concentrations in Table 3 reflect only the solubilized protein. The internal fragments were expressed in the range of 2–3.6 mg/ml. It was extremely difficult to determine the concentration of fragment 105–168 (it was suspected that the concentration was much higher than indicated), as the protein bands on the SDS gel were large, but poorly stained. The negative control contained several background proteins as expected, but no obviously induced dominant protein.

Example 23

Induction of HR in Tobacco

The full length positive control protein elicited HR down to only 5–7 µg/ml. The negative control (pET 28) imidazole purified "protein"—which contained only background proteins—elicited an HR response down to the 1:2 dilution, which lowered the sensitivity of the assay as the 1:1 and 1:2 dilutions could not be used. This false HR was likely due an affinity of the imidazole used in the purification process to bind to one or several of the background proteins, thereby not completely dialyzing out. Imidazole at a concentration of ca. 60 mM did elicit a false HR response.

One definitive domain encompassed a small internal region of the protein from a.a. 137–180 (SEQ. ID. No. 23), a mere 44 a.a, is identified as the smallest HR domain. The other potential HR domain is thought to be located in the N-terminus of the protein from a.a. 1–104 (possibly a.a. 1–75) (SEQ. ID. No. 23). It was difficult to confirm or narrow down the N-terminus HR domain due to the difficulties encountered in purifying these fragment proteins. The N-terminus fragment proteins had to be purified with urea as no protein was recovered when the native purification process was used. Consequently, these proteins precipitated during the renaturing process and were difficult or nearly impossible to get back into solution, thereby making it hard to run the proteins through the HR assay, as only soluble protein is able to elicit HR. Difficulty narrowing the N-terminus HR domain was only compounded by the fact that the negative control elicited false HR at the low dilution levels thereby reducing the sensitivity of the assay.

The internal domain proteins elicited an HR response between 5 and 10 µg/ml of protein like the positive control, and the N-terminus domain proteins elicited an HR response between 1 and 3 µg/ml, lower than the positive control.

Surprisingly, when the internal HR domain was cleaved between a.a. 168 and 169 (fragments 76–168 and 105–168) (SEQ. ID. No. 23) the fragment lost its HR activity. This suggests that the HR activity of fragment 1–168 (SEQ. ID. No. 23) should not be attributed to the internal HR domain, but rather to some other domain, leading to the assumption that there was likely a second HR domain to be found in the N-terminal region of the protein. However, as discussed earlier it was difficult to confirm this assumption.

The harpin C-terminus (a.a. 210–403 (SEQ. ID. No. 23)) did not contain an HR domain. It did not elicit HR at a detectable level using the current HR assay. Even the large C-terminal fragment from a.a. 169–403 (SEQ. ID. No. 23) did not elicit HR even though it contained part of the internal HR domain. As stated above, the protein between a.a. 168 and 169 (SEQ. ID. No. 23) causes a loss of HR activity.

Because some of the small cloned proteins with 61 a.a. or less were not expressed, several oligopeptides were synthesized with 30 a.a. to narrow down the functional region of the internal HR domain. The oligopeptides were synthesized within the range of a.a. 121–179 (SEQ. ID. No. 23). However, these oligos did not elicit the HR response. It was not expected that there would be an HR response from oligos 137–166, 121–150, and 137–156 (SEQ. ID. No. 23) as these fragments did not contain the imperative amino acids 168 and 169 (SEQ. ID. No. 23). It was expected that the oligo 150–179 (SEQ. ID. No. 23) would elicit an HR response. It is possible that 30 a.a. is too small for the protein to elicit any activity due to a lack of folding and, therefore, a lack of binding or that during the synthesis of the peptides important amino acids were missed (either in the process, or simply by the choice of which 30 amino acids to synthesize) and, therefore, the fragments would not be able to elicit HR. It is also possible, although unlikely, that these small proteins would have undergone some form of post-translational modification within the *E.coli* cell that they did not contain when synthesized and, therefore, were not able to elicit an HR response.

Example 24

Biological Activity of HR Inducing Fragments

The two N-terminal harpin fragments spanning amino acids 1–104 and amino acids 1–168 of the polypeptide of SEQ. ID. No. 23 were effective at inducing resistance of tobacco against TMV, in a similar manner as the full length harpin protein. The internal fragments spanning amino acids 76–209 and amino acids 105–209 of the polypeptide of SEQ. ID. No. 23 were also effective at inducing TMV resistance. In addition, these same four fragments conferred plant growth enhancement ("PGE") in tomato increasing the height of the plants from 4–19% taller than the buffer control plants. The full length harpin protein induced growth enhancement of 6% greater than the buffer. The negative control did not induce TMV resistance or growth enhancement.

TABLE 5

TMV resistance and PGE activity of HR inducing fragments derived from harpin

| Fragment # | Amino acids (SEQ. ID. No. 23) | HR activity | TMV resistance | PGE ht > buffer |
|---|---|---|---|---|
| 1(+control) | 1–403 | + | + | 6% |
| 2(−control) | — | − | − | −2% |
| 9 | 1–104 | + | + | 4–8% |
| 10 | 1–168 | + | + | 5–13% |
| 13 | 76–209 | + | + | 4–18% |
| 15 | 105–209 | + | + | 6–19% |

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. An isolated DNA molecule encoding only a fragment of an *Erwinia* hypersensitive response elicitor protein or polypeptide, wherein said fragment elicits a hypersensitive response in plants and is selected from the group consisting of:

(i) the C-terminal fragment of the amino acid sequence of SEQ ID NO:23 spanning amino acids 105 and 403 of SEQ ID NO:23, (ii) the N-terminal fragments of the amino acid sequence of SEQ ID NO:23 spanning the following amino acids of SEQ ID NO:23: 1 and 98, 1 and 104, 1 and 122, 1 and 168, 1 and 218, 1 and 266, 1 and 342, 1 and 321, and 1 and 372, and (iii) the internal fragments of the amino acid sequence of SEQ ID NO:23 spanning the following amino acids of SEQ ID NO:23: 76 and 209, 105 and 209, 99 and 209, 137 and 204, 137 and 200, 109 and 204, 109 and 200, 137 and 180, and 105 and 180.

2. The isolated DNA molecule according to claim 1, wherein the fragment is the C-terminal fragment of the amino acid sequence of SEQ ID NO:23 spanning amino acids 105 and 403 of SEQ ID NO:23.

3. The isolated DNA molecule according to claim 1, wherein the fragment is the N-terminal fragment of the amino acid sequence of SEQ ID NO:23 spanning the following amino acids of SEQ ID NO:23: 1 and 98, 1 and 104, 1 and 122, 1 and 168,1 and 218,1 and 266,1 and 342,1 and 321, or 1 and 372.

4. The isolated DNA molecule according to claim 1, wherein the fragment is the internal fragment of the amino acid sequence of SEQ ID NO:23 spanning the following amino acids of SEQ ID NO:23: 76 and 209, 105 and 209, 99 and 209, 137 and 204, 137 and 200, 109 and 204, 109 and 200, 137 and 180, or 105 and 180.

5. A vector consisting of the DNA molecule according to claim 1 and a heterologous nucleic acid sequence.

6. A vector according to claim 5, wherein said DNA molecule is in sense orientation and correct reading frame.

7. An isolated host cell transformed with the DNA molecule according to claim 1.

8. A host cell according to claim 7, wherein the host cell is selected from the group consisting of a plant cell and a bacterial cell.

9. A host cell according to claim 7, wherein the DNA molecule is present in a vector consisting of said DNA molecule and a heterologous nucleic acid sequence.

* * * * *